US007217709B2

(12) United States Patent
Jagtap et al.

(10) Patent No.: US 7,217,709 B2
(45) Date of Patent: May 15, 2007

(54) TETRACYCLIC BENZAMIDE DERIVATIVES AND METHODS OF USE THEREOF

(75) Inventors: Prakash Jagtap, Beverly, MA (US); Csaba Szabo, Gloucester, MA (US)

(73) Assignee: Inotek Pharmaceuticals Corporation, Beverly, MA (US)

( * ) Notice: Subject to any disclaimer, the term of this patent is extended or adjusted under 35 U.S.C. 154(b) by 0 days.

(21) Appl. No.: 10/788,228

(22) Filed: Feb. 26, 2004

(65) Prior Publication Data

US 2004/0229895 A1    Nov. 18, 2004

Related U.S. Application Data

(60) Provisional application No. 60/450,925, filed on Feb. 28, 2003.

(51) Int. Cl.
A61K 31/5377 (2006.01)
A61K 31/473 (2006.01)
C07D 413/12 (2006.01)
C07D 221/18 (2006.01)

(52) U.S. Cl. .................... 514/232.8; 544/125; 546/61; 514/284

(58) Field of Classification Search ................ 514/284, 514/232.8; 546/61; 544/125
See application file for complete search history.

(56) References Cited

U.S. PATENT DOCUMENTS

| 3,710,795 | A | 1/1973 | Higuchi et al. |
| 4,113,731 | A | 9/1978 | Winters et al. |
| 4,263,304 | A | 4/1981 | Ishizumi et al. |
| 4,623,304 | A | 11/1986 | Chikada |
| 5,079,246 | A | 1/1992 | Forbes et al. |
| 5,260,316 | A | 11/1993 | Van Duzer et al. |
| 5,262,564 | A | 11/1993 | Kun et al. |
| 5,597,831 | A | 1/1997 | Michalsky et al. |
| 5,710,162 | A | 1/1998 | Okazaki et al. |
| 5,733,918 | A | 3/1998 | Okazaki et al. |
| 6,028,079 | A | 2/2000 | Okazaki et al. |
| 6,346,535 | B1 | 2/2002 | Cotter et al. |
| 6,346,536 | B1 | 2/2002 | Li et al. |
| 6,498,194 | B2 | 12/2002 | Cotter et al. |
| 6,635,642 | B1 | 10/2003 | Jackson et al. |
| 6,828,319 | B2 | 12/2004 | Jagtap et al. |
| 2002/0099063 | A1 | 7/2002 | Cotter et al. |
| 2004/0039009 | A1 | 2/2004 | Jagtap et al. |
| 2005/0261288 | A1 | 11/2005 | Jagtap et al. |
| 2006/0019980 | A1 | 1/2006 | Szabo et al. |

FOREIGN PATENT DOCUMENTS

| CA | 2349227 | 5/2000 |
| GB | 2025932 B2 | 1/1980 |
| JP | 2003267888 | 9/2003 |
| WO | WO 93/05023 | 3/1993 |
| WO | WO 99/08680 | 2/1999 |
| WO | WO 99/11311 | 3/1999 |
| WO | WO 99/11623 | 3/1999 |
| WO | WO 99/11628 | 3/1999 |
| WO | WO 99/11644 | 3/1999 |
| WO | WO 99/11645 | 3/1999 |
| WO | WO 99/11649 | 3/1999 |
| WO | WO 99/59973 | 11/1999 |
| WO | WO 99/59975 | 11/1999 |
| WO | WO 00/21537 | 4/2000 |
| WO | WO 00/39070 | 7/2000 |
| WO | WO 00/39104 | 7/2000 |
| WO | WO 00/42040 | 7/2000 |
| WO | WO 01/12199 | 2/2001 |
| WO | WO-01/90077 | 11/2001 |
| WO | WO 02/06284 | 1/2002 |
| WO | WO-04/014862 A1 | 2/2004 |
| WO | WO 2004/043959 | 5/2004 |
| WO | WO 2005/012524 | 2/2005 |
| WO | WO 2005/053662 | 6/2005 |

OTHER PUBLICATIONS

Abdelkarim et al., Protective effects of PJ34, a novel, potent inibitor of poly(ADP-ribose) polymerase (PARP) in in vitro and in vivo models of stroke, Int. J. Mol. Med., 7:255-260, 2001.
Aldrich, p. 32, Aldrich Chemicl Company, 1992.
Ando et al., Cyclization reactions of 1,2-bis(2-cyanophenyl_propionitriles. II. Synthesis of 5-amino-4,7-dimethoxy-11H-indo[1,2-c]isoquinolin-11-one, Bull. Chem. Soc. Japan, 47:1014-17, 1974.
Bloch et al., The role of the 5'-hydroxyl group of adenosine in determining substrate specificity for adenosine deaminase, J. Med. Chem., 10(5):908-912, 1967.
Burger's Medicinal Chemistry and Drug Discovery, 5th ed., vol. 1: Principles and Practice, John Wiley and Sons, Inc., pp. 975-977, 1994.
Chatterjea et al., Cyclisation of alpha-benzythomophthalic acids, Experientia, 16:439-440, 1960.
Cushman et al., Synthesis of new indeno[1,2b]isoquinolines: Cytotoxic non-camptothecin topoisomerase I inhibitors, J. Med. Chem., 43(20):3688-3698, 2000.
Dusemund et al., 5-hydroxyisoindolo[2,1b]isoquinolin-7-one: Synthesis and isomerization, Arch. Pharm (Weinheim, Ger.), 317:381-2, 1984.
Grupp et al., Protection against hypoxia-reoxygenation in the absence of poly9ADP-ribose) synthetase in isolated working hearts, J. Mol. Cell Cardiol., 31:297-303, 1999.
Hakimelahi et al., Ring Open Analogues of Adenine Nucleoside, Aminoacyl Derivatives of Cyclo- and Acyclo-nucleosides, Helvetica Chemica Acta, 70:219-231, 1987.

(Continued)

Primary Examiner—Charanjit S. Aulakh
(74) Attorney, Agent, or Firm—Wilmer Cutler Pickering Hale and Dorr LLP

(57) ABSTRACT

The invention relates to Tetracyclic Benzamide Derivatives; compositions comprising a Tetracyclic Benzamide Derivative; and methods for treating or preventing an inflammatory disease, a reperfusion disease, an ischemic condition, renal failure, diabetes, a diabetic complication, a vascular disease, or cancer, comprising administering to a subject in need thereof an effective amount of a Tetracyclic Benzamide Derivative.

15 Claims, No Drawings

OTHER PUBLICATIONS

Hiremath et al., A New Method for the Synthesis of 6H, 11H-Indolo[3,2-c]-isoquinolin-5-ones/thiones and their Reactions, J. Heterocyc. Chem., 30(3):603-609, 1993.

Hiremath et al., Synthesis of substituted 2-(5-oxo/thioxo-1,3,4-oxadiazol-2-yl)-indoles & 2-(5-oxo/thioxo-1,3,4-oxadiazol-2-ylamino)indoles, Indian Journal of Chemistry, Section B 22B(6):571-576, 1983.

Jantzen and Robinson, Modern Pharmaceutics, 3rd ed., eds. Baker and Rhodes, p. 596, 1995.

Kawana et al., Nucleoside Peptides. III. The Synthesis of N-[1-(9-Adenyl)-β-D-ribofuranuronosyl] Derivatives of Certain Aminio Acids and Peptides, J. Org. Chem., 37(2):288-290, 1972.

Kirby et al., Hydride hyperconjugation in 1(3)-methylazulenes, Tetrahedron Lett., 27:1-4; 1960.

Kirby et al., 4,6,8-trimethylazulenium percholrate. Chemistry & Industry (London, UK), 1217-1218, 1960.

Lal et al., Applications of carbon-nitrogen bond cleavage reaction: A synthesis/derivisation of 11H-indeno[1,2-c]isoquinolones, Indian J. Chem., Sect. B, 38B:33-39, 1999.

Lamping et al., LPS_binding protein protects mice from septic shock caused by LPS or gram-negative bacteria, J. Clin. Invest., 101(10):2065-2071, 1998.

Mabley et al., Inhibition of poly(ADP-ribose) synthetase by gene disruption or inhibitin with 5-iodo-6-amino-1,2-benzopyrone protects mice from multiple-low-dose-streptozotocin-induced diabetes, Br. J. Pharmacol., 133(6):909-919, 2001.

Mandir et al., A novel in vivo post-translational modification of p53 by PARP-1 in MPTP-induced parkinsonism, J. Neurochem., 83(1):186-192, 2002.

Mandir et al., Poly(ADP-ribose) polymerase activation mediates 1-methyl-4-phenyl-1,2,3,6-tetrahydropyridine (MPTP)-induced parkinsonism, Proc. Natl. Acad. Sci. U.S. A., 96(10):5774-5779, 1999.

Morrison and Boyd, Organic Chemistry, 5th ed., Allyn and Bacon, Inc., p. 179, 1987.

Ojika et al, Ptaquiloside, a Potent Carcinogen Isolated From Bracken Fern Pteridium Aquilinum Var. Latiusculum: Structure Elucidation Based On Chemical and Spectral Evidence, and Reactions with Amino Acids, Nucleosides, and Nucleotides, Tetrahedron, 43(22):5261-5274, 1987.

Parrillo, Pathogenic mechanisms of septic shock, N. Eng. J. Med., 328:1471-1477, 1993.

Southan and Szabo, Poly(ADP-ribose) polymerase inhibitors, Curr. Med. Chem., 10:321, 2003.

Strumberg et al., Synthesis of cytotoxic indenosoquinoline topolsomerase I poisons, J. Med. Chem., 42(3):446-457, 1999.

Virag et al., Peroxynitrite-induced thymocyte apoptosis: the role of caspases and poly(ADP-ribose) synthetase (PARP) activation, immunol., 94(3):345-355, 1998.

Wang et al., Apoptosis inducing factor and PARP-mediated injury in the MPTP mouse model of Parkinson's disease, Ann N.Y. Acad. Sci., 991:132-139, 2003.

Wawzonek et al., Synthesis of 6-substituted-6H-indeno[1,2-c]isoquinoline-5,11-diones, Org. Prep. Proc. Int., 14:163-8, 1982.

Wawzonek et al., Preparation and reactions of 4b-acetoxy-4b,9b-dihydroindeno[2,1-a]indene-5,10-dione, Can. J. Chem., 59:2833, 1981.

Yamaguchi et al., The Synthesis of Benzofuroquinolines. IX. A Benzofuroisoquinolinone and a Benzofuroisocoumarin, J. Heterocycl. Chem., 32(2):419-423, 1995.

Yamaguchi et al., The synthesis of benzofuroquinolines. X. Some benzofuro[3,2-c]isoquinoline derivatives, J. Hetercycl. Chem., 32(5):1517-1520, 1995.

Banasik et al., Inhibitors and activators of ADP-ribosylation reactions. Mol Cell Biochem. Sep. 1994;138(1-2):185-97.

Banasik et al., Specific inhibitors of poly(ADP-ribose) synthetase and mono(ADP-ribosyl)transferase. J Biol Chem. Jan. 25, 1992;267(3):1569-75.

Chatterjea et al., On 4-Keto-3:4-Dihydroisocoumarin, J. Indian Chem. Society, 44(11):911-919, 1967.

Griffin et al., Resistance-modifying agents. 5. Synthesis and biological properties of quinazolinone inhibitors of the DNA repair enzyme poly(ADP-ribose) polymerase (PARP). J Med Chem. Dec. 17, 1998;41(26):5247-56.

Hiremath et al., 1997, "Synthesis and Biological Studies of Some New Bridgehead Nitrogen Heterocycles Containing Indoloisoquinoline Nucleus", Oriental J. of Chemistry 13 (2):173-6.

Hiremath et al., Synthesis of Substituted 7H-Indolo[2,3-c] isoquinolines, Indian J. Of Chemistry, Section B 24B(12):1235-1238, 1985.

Hiremath et al., Synthesis and Biological Evaluation of Some Substituted 5H, 6H, 7H,-Indolo[2,3-C] Isoquinolin-5-thiones and their Derivatives, Indian J. of Heterocyclic Chemistry, 3(1):37-42, 1993.

Hiremath et al., Synthesis of [10-substituted-6H,7H-indolo[2,3-c]iso-quinolin-5-one-6-yl]acetyl-3,5-disubstituted-pyrazoles/ pryazolones and 5-[10-substituted-6H,7H-indolo[2,3-c]iso-quinolin-5-one-6-yl]methyl-1,3,4-oxadiazol-2-thiones, J of the Indian Chemical Society, 72(10):735-738, 1995.

Jha et al., Synthesis of Indeno[2,1-c] isocoumarins and indeno[2,1-c]isoquinolones, Indian J. of Chemistry, Section B, 24B(4): Section B 24B(4):440-444, 1985.

Milam et al., Inhibitors of poly(adenosine diphosphate-ribose) synthesis: effect on other metabolic processes. Science. Feb. 10, 1984;223(4636):589-91.

Ohno et al., 2004, Modulation of adenosine receptor affinity and intrinsic efficacy in adenine nucleosides substituted at the 2 position, Biorganic and Medicinal Chemistry 12: 2995-3007.

Shinkwin et al., Synthesis of thiophenecarboxamides, thieno[3,4-c]pyridin-4(5H)-ones and thieno[3,4-d]pyrimidin-4(3H)-ones and preliminary evaluation as inhibitors of poly(ADP-ribose)polymerase (PARP), Bioorg Med Chem, Feb. 1999;7(2):297-308.

Soriano et al. Diabetic endothelial dysfunction: the role of poly (ADP-ribose) polymerase activation. Nat. Med. Jan. 2001;7(1):108-13.

Srivastava et al., Synthesis of Indeno[2,1-c] isocoumarins and indeno[2,1-c]isoquinolones, J. of the Indian Chemical Society, 66(4):276-81, 1989.

Szabo et al., Role of poly(ADP-ribose) synthetase in inflammation and ischaemia-reperfusion. Trends Pharmacol Sci. Jul. 1998;19(7):287-98. Review.

Szabo et al., The pathophysiological role of peroxynitrite in shock, inflammation, and ischemia-reperfusion injury. Shock. Aug. 1996;6(2):79-88.

White et al., Resistance-modifying agents. 9. Synthesis and biological properties of benzimidazole inhibitors of the DNA repair enzyme poly(ADP-ribose) polymerase.J Med Chem. Nov. 2, 2000;43(22):4084-97.

Winters et al., Synthesis and biological activities of some indolo[2,3-c]isoquinoline derivatives. Farmaco [Sci]. Jun. 1979;34(6):507-17.

Zhang et al., GPI 6150 prevents H(2)O(2) cytotoxicity by inhibiting poly(ADP-ribose) polymerase. Biochem Biophys Res Commun. Nov. 30, 2000;278(3):590-8.

Peukert and Schwhan, Expert Opin. Ther. Patents 14(11):1531-1551 (2004).

Mandir et al., Poly(ADP-ribose) Activation Mediates 1-methyl-4-phenyl-1,2,3,6-tetrahydropyridine (MPTP)-Induced Parkinsonism, Proc. Nat. Acad. Sci. USA 96:5774-5779 (1999).

Jijon et al., Inhibition of poly(ADP-ribose) Polymerase Attenuates Inflammation in a Model of Chronic Colitis, Am. J. Physiol. Gastrointest. Liver Physiol. 279:G641-G651 (2000).

Szabo et al., Role of poly(ADP-ribose) Synthetase in Inflammation and Ischaemia-reperfusion, Trends in Pharm. Sci. 19:287-298 (1998).

Virag et al., The Therapeutic Potential of Poly(ADP-Ribose) Polymerase Inhibitors, Pharmacol. Rev. 54:375-429 (2002).

Lohinai et al., Role of the Activation of the Nuclear Enzyme Poly(ADP-Ribose) Polymerase in the Pathogenesis of Periodontitis, J. Dent. Res. 82:987-992 (2003).

Virag et al., Effects of poly(ADP-Ribose) Polymerase Inhibition on Inflammatory Cell Migration in a Murine Model of Asthma, *Med. Sci. Monit. 10*:BR77-BR83 (2004).

Szabo et al., Roles of poly(ADP-ribose) Polymerase Activation in the Pathogenesis of Diabetes mellitus and its Complications, *Pharmacol. Res. 52*:60-71 (2005).

Szabo et al., Poly(ADP-Ribose) Polymerase Inhibition Reduces Reperfusion Injury After Heart Transplantation, *Circulation Research* 90:100-106 (2002).

Bryant et al., Specific killing of BRCA2-deficient tumours with inhibitors of poly(ADP-ribose)polymerase. *Nature* 434:913-917 (2005).

Martin et al., Inhibition of poly(ADP-ribose) polymerase attenuates ischemic renal injury in rats. *Am. J. Physiol. Regulatory Integrative Comp. Physiol. 279*:R1834-R1840 (2000).

Graziani et al., Clinical perspectives of PARP inhibitors. *Pharmacological Research*, 52:109-118 (2005).

Pacher et al., Role of Nitrosative Stress and Peroxynitrite in the Pathogenesis of Diabetic Complications. Emerging New Therapeutical Strategies, *Curr. Med. Chem. 12*:267-275 (2005).

Curtin et al., PARP inhibitors for cancer therapy. *Expert Reviews in Molecular Medicine* 7:1-20 (2005).

Wawzonek et al., The Synthesis and Reactions of 1-Carbamyl-11-ketoindeno[1,2-c]isoquinoline, *J. Org. Chem. 31*:1004-1006 (1966).

Dorland's Illustrated Medical Dicitionary 650 (29th ed. 2000).

Chatterjea et al., "The Course of Cyclisation of α-Benzylhomophthalic Acids. Part I. A New Route To 2:3-6:7-Dibenzotropones," Journal Indian Chem. Soc., (1960) vol. 37 (7): 379-391.

TETRACYCLIC BENZAMIDE DERIVATIVES AND METHODS OF USE THEREOF

This application claims benefit of U.S. provisional application No. 60/450,925, filed Feb. 28, 2003, the entire disclosure of which is hereby incorporated by reference.

This invention was made with government support under grant no. R44 DK54099-03 and grant no. 1R43 CA90016-01A1, which were awarded by the National Institutes of Health. The government has certain rights in the invention.

1. FIELD OF THE INVENTION

The invention relates to Tetracyclic Benzamide Derivatives; compositions comprising an effective amount of a Tetracyclic Benzamide Derivative; and methods for treating or preventing an inflammatory disease, a reperfusion disease, an ischemic condition, renal failure, diabetes, a diabetic complication, a vascular disease, or cancer, comprising administering to a subject in need thereof an effective amount of a Tetracyclic Benzamide Derivative.

2. BACKGROUND OF THE INVENTION

Inflammatory diseases, such as arthritis, colitis, and autoimmune diabetes, typically manifest themselves as disorders distinct from those associated with reperfusion diseases, e.g., stroke and heart attack, and can clinically manifest themselves as different entities. However, there can be common underlying mechanisms between these two types of disorders. In particular, inflammatory disease and reperfusion disease can induce proinflammatory cytokine and chemokine synthesis which can, in turn, result in production of cytotoxic free radicals such as nitric oxide and superoxide. NO and superoxide can react to form peroxynitrite (ONOO$^-$) (Szabó et al., Shock 6:79–88, 1996).

The ONOO$^-$-induced cell necrosis observed in inflammatory disease and in reperfusion disease involves the activation of the nuclear enzyme poly (ADP-ribose) synthetase (PARS), also known as poly (ADP-ribose) polymerase (PARP). Activation of PARP is thought to be an important step in the cell-mediated death observed in inflammation and reperfusion disease (Szabó et al., Trends Pharmacol. Sci. 19:287–98, 1998).

A number of PARP inhibitors have been described in the art. See, e.g., Banasik et al., J. Biol. Chem., 267:1569–75, 1992, and Banasik et al., Mol. Cell. Biochem., 138:185–97, 1994; WO 00/39104; WO 00/39070; WO 99/59975; WO 99/59973; WO 99/11649; WO 99/11645; WO 99/11644; WO 99/11628; WO 99/11623; WO 99/11311; WO 00/42040; Zhang et al., Biochem. Biophys. Res. Commun., 278:590–98, 2000; White et al., J. Med. Chem., 43:4084–4097, 2000; Griffin et al., J. Med. Chem., 41:5247–5256, 1998; Shinkwin et al., Bioorg. Med. Chem., 7:297–308, 1999; and Soriano et al., Nature Medicine, 7:108–113, 2001. Adverse effects associated with administration of PARP inhibitors have been discussed in Milan et al., Science, 223:589–591, 1984.

S. P. Hiremath et al., Oriental Journal of Chemistry 13(2):173–176 (1997) discloses isoquinoline compounds allegedly useful as antifungal, antibacterial or anthelmintic agents.

S. P. Hiremath et al., Journal of the Indian Chemical Society 72(10):735–738 (1995) discloses isoquinolinone compounds S. P. Hiremath et al., Indian Journal of Heterocyclic Chemistry 3(1):37–42 (1993) discloses isoquinolinethione compounds allegedly useful as antifungal, antibacterial, oxytocic or anthelmintic agents.

S. P. Hiremath et al., Indian Journal of Chemistry, Section B 24B(12):1235–1238 (1985) discloses indoloisoquinoline compounds.

U.S. Pat. No. 4,623,304 to Ishizumi et al. discloses indoloisoquinoline compounds allegedly having anti-tumor activity.

United Kingdom Patent No. GB 2025932 B2 by Sumitomo Chemical Co. discloses indoloisoquinoline compounds allegedly having bacteriacidal or fungicidal activity.

G. Winters et al., Farmaco. Ed. Sci. 34(6):507–517 (1979) discloses indoloisoquinolinones allegedly having antibacterial or fungicidal activity.

U.S. Pat. No. 4,113,731 to G. Winters et al. discloses indoloisoquinolines.

U.S. Pat. Nos. 5,733,918, 5,710,162, and 6,028,079 to Okazaki et al. disclose indenoquinolines allegedly useful as antitumor agents.

S. Srivastava et al., Journal of the Indian Chemical Society 66(4):276–81 (1989) discloses a synthesis of indenoisocoumarins and indenoisoquinolones.

G. Jha et al., Indian Journal of Chemistry, Section B 24B(4):440–444 (1985) discloses a synthesis of indenoisocoumarins and indenoisoquinolones.

J. N. Chatterjea et al., J. Indian Chem. Soc. 44(11): 911–919 (1967) discloses a synthesis of dihydroisocoumarins.

There remains, however, a need in the art for compounds useful for treating or preventing an inflammatory disease, a reperfusion disease, an ischemic condition, renal failure, diabetes, a diabetic complication, a vascular disease, or cancer.

Citation of any reference in Section 2 of this application is not an admission that the reference is prior art.

3. SUMMARY OF THE INVENTION

The present invention encompasses compounds having the Formula (I):

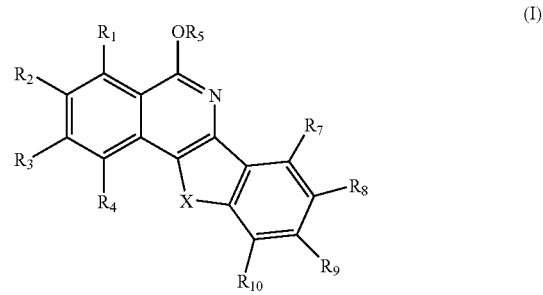

and pharmaceutically acceptable salts and hydrates thereof, wherein:

R$_5$ is —C$_1$–C$_{10}$ alkyl, halo-substituted-(C$_1$–C$_5$ alkyl), HO-substituted-(C$_1$–C$_5$ alkyl), carboxy-substituted-(C$_1$–C$_5$ alkyl), —C(O)—C$_1$–C$_{10}$ alkyl, —C(O)-aryl, —C(O)-(3- to 7-membered mono cyclic heterocycle), —C(O)-(7- to 10-membered bicyclic heterocycle) or -glycoside;

X is —C(O)—, —CH$_2$—, —CH(halo)-, —(C(OH)((CH$_2$)$_n$CH$_3$))—, —(C(OH)(aryl))-, —O—, —NH—, —S—, —CH(NR$_{11}$R$_{12}$)— or —N(SO$_2$Y)—, wherein Y is —OH, —NH$_2$, —C$_1$–C$_5$ alkyl)-(3- to 7-membered monocyclic heterocycle), or —(C$_1$–C$_5$ alkyl)-(7- to 10-membered bicyclic heterocycle) and n is an integer ranging from 0–5;

R$_{11}$ and R$_{12}$ are independently -hydrogen or —C$_1$–C$_9$ alkyl, or N, R$_{11}$ and R$_{12}$ are taken together to form a -(nitrogen-containing 3- to 7-membered monocyclic heterocycle), or a -(nitrogen-containing 7- to 10-membered bicyclic heterocycle);

R$_1$, R$_2$, R$_3$, R$_4$, R$_7$, R$_8$, R$_9$ and R$_{10}$ are independently -hydrogen, -halo, -hydroxy, —O—(C$_1$–C$_5$ alkyl), —C$_1$–C$_{10}$ alkyl, halo-substituted-(C$_1$–C$_5$ alkyl), —C$_2$–C$_{10}$ alkenyl, —C$_3$–C$_8$-cycloalkyl, -aryl, —NH$_2$, amino-substituted-(C$_1$–C$_5$ alkyl), —C(O)OH, —C(O)O(C$_1$–C$_5$ alkyl), —OC(O)(C$_1$–C$_5$ alkyl), NO$_2$ or -A-B;

A is —SO$_2$—, —SO$_2$NH—, —NHCO—, —NH-CONH—, —O—, —CO—, —OC(O)—, —C(O)O—, —CONH—, —CON(C$_1$–C$_4$ alkyl)-, —NH—, —CH$_2$—, —S— or —C(S)—;

B is —C$_1$–C$_{10}$ alkyl, —C$_2$–C$_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —C$_3$–C$_8$ cycloalkyl, -aryl, —NZ$_1$Z$_2$, —(C$_1$–C$_5$ alkylene)-NZ$_1$Z$_2$, amino-substituted-(C$_1$–C$_5$ alkyl), —N(C$_1$–C$_5$ alkyl)(C$_1$–C$_5$ alkyl), —(C$_1$–C$_5$ alkyl)-(3- to 7-membered monocyclic heterocycle), or —(C$_1$–C$_5$ alkyl)-(7- to 10-membered bicyclic heterocycle), —(H$_2$NC(O))-substituted aryl, —(H$_2$NC(O))-substituted pyridyl, —C(O)OH, —C(O)O—(C$_1$–C$_5$ alkyl), —C(O)O-phenyl or —C(NH)NH$_2$, each of which is unsubstituted or substituted with one or more of —O—(C$_1$–C$_5$ alkyl), -halo, halo-substituted-(C$_1$–C$_5$ alkyl), HO-substituted-(C$_1$–C$_5$ alkyl), amino-substituted-(C$_1$–C$_5$ alkyl), -hydroxy, —NO$_2$, —NH$_2$, —CN, —NH(C$_1$–C$_5$ alkyl), —N(C$_1$–C$_5$ alkyl)(C$_1$–C$_5$ alkyl), -(nitrogen-containing 3- to 7-membered monocyclic heterocycle), 7- to 10-membered bicycloheterocyclic amine, —C$_1$–C$_{10}$ alkyl, —C$_2$–C$_{10}$ alkenyl, —C$_2$–C$_{10}$ alkynyl, -aryl, -benzyl, —(C(O)NH$_2$)-substituted(C$_1$–C$_5$ alkyl), carboxy-substituted-(C$_1$–C$_5$ alkyl), —C(O)OH, —C$_1$–C$_5$-alkylene-C(O)O—(C$_1$–C$_5$ alkyl) or —C$_1$–C$_5$ alkylene-OC(O)—(C$_1$–C$_5$ alkyl); and Z$_1$ and Z$_2$ are independently —H or —C$_1$–C$_{10}$ alkyl, which is unsubstituted or substituted with one or more of -halo, —OH or —N(Z$_3$)(Z$_4$), where Z$_3$ and Z$_4$ are independently, —H or —C$_1$–C$_5$ alkyl, which is unsubstituted or substituted with one or more of -halo, -hydroxy or —NH$_2$; or N, Z$_3$ and Z$_4$ are taken together to form a (nitrogen-containing 3- to 7-membered monocyclic heterocycle) or a -(nitrogen-containing 7- to 10-membered bicyclic heterocycle); or N, Z$_1$ and Z$_2$ are taken together to form a -(nitrogen-containing 3- to 7-membered monocyclic heterocycle), or a -(nitrogen-containing 7- to 10-membered bicyclic heterocycle).

The present invention also encompasses compounds of Formula (Ia):

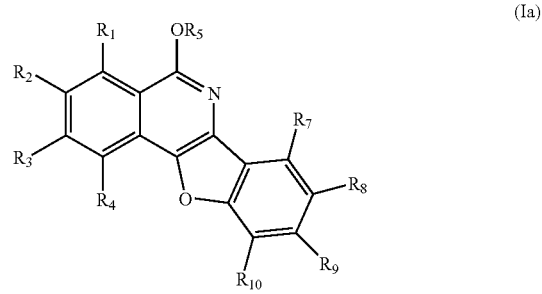

(Ia)

and pharmaceutically acceptable salts and hydrates thereof, wherein:

R$_5$ is —C$_1$–C$_{10}$ alkyl, halo-substituted-(C$_1$–C$_5$ alkyl), HO-substituted-(C$_1$–C$_5$ alkyl), carboxy-substituted-(C$_1$–C$_5$ alkyl), —C(O)—C$_1$–C$_{10}$ alkyl, —C(O)-aryl, —C(O)-(3- to 7-membered monocyclic heterocycle), —C(O)-(7- to 10-membered bicyclic heterocycle) or -glycoside;

R$_1$, R$_2$, R$_3$, R$_4$, R$_7$, R$_8$, R$_9$ and R$_{10}$ are independently -hydrogen, -halo, -hydroxy, —O—(C$_1$–C$_5$ alkyl), —C$_1$–C$_{10}$ alkyl, halo-substituted-(C$_1$–C$_5$ alkyl), —C$_2$–C$_{10}$ alkenyl, —C$_3$–C$_8$-cycloalkyl, -aryl, —NH$_2$, amino-substituted-(C$_1$–C$_5$ alkyl), —C(O)OH, —C(O)O(C$_1$–C$_5$ alkyl), —OC(O)(C$_1$–C$_5$ alkyl), NO$_2$ or -A-B;

A is —SO$_2$—, —SO$_2$NH—, —NHCO—, —NH-CONH—, —O—, —CO—, —OC(O)—, —C(O)O—, —CONH—, —CON(C$_1$–C$_4$ alkyl)-, —NH—, —CH$_2$—, —S— or —C(S)—;

B is —C$_1$–C$_{10}$ alkyl, —C$_2$–C$_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —C$_3$–C$_8$ cycloalkyl, -aryl, —NZ$_1$Z$_2$, —(C$_1$–C$_5$ alkylene)-NZ$_1$Z$_2$, amino-substituted-(C$_1$–C$_5$ alkyl), —N(C$_1$–C$_5$ alkyl)(C$_1$–C$_5$ alkyl), —(C$_1$–C$_5$ alkyl)-(3- to 7-membered monocyclic heterocycle), or —(C$_1$–C$_5$ alkyl)-(7- to 10-membered bicyclic heterocycle), —(H$_2$NC(O))-substituted aryl, —(H$_2$NC(O))-substituted pyridyl, —C(O)OH, —C(O)O—(C$_1$–C$_5$ alkyl), —C(O)O-phenyl or —C(NH)NH$_2$, each of which is unsubstituted or substituted with one or more of —O—(C$_1$–C$_5$ alkyl), -halo, halo-substituted-(C$_1$–C$_5$ alkyl), HO-substituted-(C$_1$–C$_5$ alkyl), amino-substituted-(C$_1$–C$_5$ alkyl), -hydroxy, —NO$_2$, —NH$_2$, —CN, —NH(C$_1$–C$_5$ alkyl), —N(C$_1$–C$_5$ alkyl)(C$_1$–C$_5$ alkyl), -(nitrogen-containing 3- to 7-membered monocyclic heterocycle), 7- to 10-membered bicycloheterocyclic amine, —C$_1$–C$_{10}$ alkyl, —C$_2$–C$_{10}$ alkenyl, —C$_2$–C$_{10}$ alkynyl, -aryl, -benzyl, —(H$_2$NC(O))-substituted(C$_1$–C$_5$ alkyl), carboxy-substituted-(C$_1$–C$_5$ alkyl), —C(O)OH, —C$_1$–C$_5$-alkylene-C(O)O—(C$_1$–C$_5$ alkyl) or —C$_1$–C$_5$ alkylene-OC(O)—(C$_1$–C$_5$ alkyl); and Z$_1$ and Z$_2$ are independently —H or —C$_1$–C$_{10}$ alkyl, which is unsubstituted or substituted with one or more of -halo, —OH or —N(Z$_3$)(Z$_4$), where Z$_3$ and Z$_4$ are independently, —H or —C$_1$–C$_5$ alkyl, which is unsubstituted or substituted with one or more of -halo, -hydroxy or —NH$_2$; or N, Z$_3$ and Z$_4$ are taken together to form a -(nitrogen-containing 3- to 7-membered monocyclic heterocycle) or a -nitrogen-containing 7- to 10-membered bicyclic heterocycle); or N, Z$_1$ and Z$_2$ are taken together to form a -(nitrogen-containing 3- to 7-membered monocyclic heterocycle), or a -(nitrogen-containing 7- to 10-membered bicyclic heterocycle).

The present invention also encompasses compounds of Formula (Ib):

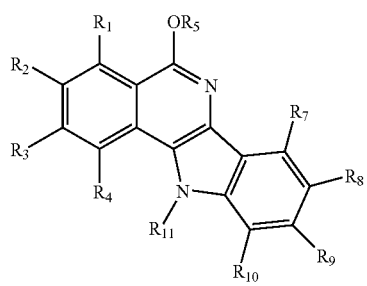

(Ib)

and pharmaceutically acceptable salts and hydrates thereof, wherein:

$R_5$ is —$C_1$–$C_{10}$ alkyl, halo-substituted-($C_1$–$C_5$ alkyl), HO-substituted-($C_1$–$C_5$ alkyl), carboxy-substituted-($C_1$–$C_5$ alkyl), —C(O)-$C_1$–$C_{10}$ alkyl, —C(O)-aryl, —C(O)-(3- to 7-membered monocyclic heterocycle), —C(O)-(7- to 10-membered bicyclic heterocycle) or -glycoside;

$R_{11}$—H, —$C_1$–$C_5$ alkyl, -aryl, —C(O)—$C_1$–$C_5$ alkyl, or —$SO_2Y$, wherein Y is —OH, —$NH_2$ or —($C_1$–$C_5$ alkyl)-(3- to 7-membered monocyclic heterocycle), or —($C_1$–$C_5$ alkyl)-(7- to 10-membered bicyclic heterocycle);

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, halo-substituted-($C_1$–$C_5$ alkyl), —$C_2$–$C_{10}$ alkenyl, —$C_3$–$C_8$-cycloalkyl, -aryl, —$NH_2$, amino-substituted-($C_1$–$C_5$ alkyl), —C(O)OH, —C(O)O($C_1$–$C_5$ alkyl), —OC(O)($C_1$–$C_5$ alkyl), $NO_2$ or -A-B;

A is —$SO_2$—, —$SO_2NH$—, —NHCO—, —NHCONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —$C_3$–$C_8$ cycloalkyl, -aryl, —$NZ_1Z_2$, —($C_1$–$C_5$ alkylene)-$NZ_1Z_2$, amino-substituted-($C_1$–$C_5$ alkyl), —N($C_1$–$C_5$ alkyl)($C_1$–$C_5$ alkyl), —($C_1$–$C_5$ alkyl)-(3- to 7-membered monocyclic heterocycle), or —($C_1$–$C_5$ alkyl)-(7- to 10-membered bicyclic heterocycle), —($H_2NC(O)$)-substituted aryl, —($H_2NC(O)$)-substituted pyridyl, —C(O)OH, —C(O)O—($C_1$–$C_5$ alkyl), —C(O)O-phenyl or —C(NH)$NH_2$, each of which is unsubstituted or substituted with one or more of —O—($C_1$–$C_5$ alkyl), -halo, halo-substituted-($C_1$–$C_5$ alkyl), HO-substituted-($C_1$–$C_5$ alkyl), amino-substituted-($C_1$–$C_5$ alkyl), -hydroxy, —$NO_2$, —$NH_2$, —CN, —NH($C_1$–$C_5$ alkyl), —N($C_1$–$C_5$ alkyl)($C_1$–$C_5$ alkyl), -(-(nitrogen-containing 3- to 7-membered monocyclic heterocycle)), 7- to 10-membered bicycloheterocyclic amine, —$C_1$–$C_{10}$ alkyl, —$C_2$–$C_{10}$ alkenyl, —$C_2$–$C_{10}$ alkynyl, -aryl, -benzyl, —($H_2NC(O)$)-substituted($C_1$–$C_5$ alkyl), carboxy-substituted-($C_1$–$C_5$ alkyl), —C(O)OH, —$C_1$–$C_5$-alkylene-C(O)O—($C_1$–$C_5$ alkyl) or —$C_1$–$C_5$ alkylene-OC(O)—($C_1$–$C_5$ alkyl); and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form a -(nitrogen-containing 3- to 7-membered monocyclic heterocycle) or a -(nitrogen-containing 7- to 10-membered bicyclic heterocycle); or N, $Z_1$ and $Z_2$ are taken together to form a -(nitrogen-containing 3- to 7-membered monocyclic heterocycle), or a -nitrogen-containing 7- to 10-membered bicyclic heterocycle).

The invention also relates to compounds of Formula (II):

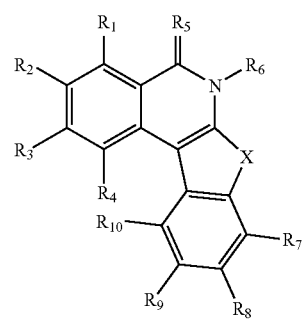

(II)

and pharmaceutically acceptable salts and hydrates thereof, wherein:

$R_5$ is O, NH or S;

$R_6$ is —H or $C_1$–$C_4$ alkyl;

X is —C(O)—, —$CH_2$—, —CH(halo)-, —(C(OH)(($CH_2$)$_n$$CH_3$))-, —(C(OH)(aryl))-, —O—, —NH—, —S—, —CH(N$R_{11}$$R_{12}$)— or —N($SO_2Y$)—, wherein Y is —OH, —$NH_2$, —($C_1$–$C_5$ alkyl)-(3- to 7-membered monocyclic heterocycle), or —($C_1$–$C_5$ alkyl)-(7- to 10-membered bicyclic heterocycle) and n is an integer ranging from 0–5;

$R_{11}$ and $R_{12}$ are independently -hydrogen or —$C_1$–$C_9$ alkyl, or N, $R_{11}$ and $R_{12}$ are taken together to form a -(nitrogen-containing 3- to 7-membered monocyclic heterocycle), or a -(nitrogen-containing 7- to 10-membered bicyclic heterocycle);

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, halo-substituted-($C_1$–$C_5$ alkyl), —$C_2$–$C_{10}$ alkenyl, —$C_3$–$C_8$-cycloalkyl, -aryl, —$NH_2$, amino-substituted-($C_1$–$C_5$ alkyl), —C(O)OH, —C(O)O($C_1$–$C_5$ alkyl), —OC(O)($C_1$–$C_5$ alkyl), $NO_2$ or -A-B;

A is —$SO_2$—, —$SO_2NH$—, —NHCO—, —NHCONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —$C_3$–$C_8$ cycloalkyl, -aryl, —$NZ_1Z_2$, —($C_1$–$C_5$ alkylene)-$NZ_1Z_2$, amino-substituted-($C_1$–$C_5$ alkyl), —N($C_1$–$C_5$ alkyl)($C_1$–$C_5$ alkyl), —($C_1$–$C_5$ alkyl)-(3- to 7-membered monocyclic heterocycle), or —$C_1$–$C_5$ alkyl)-(7- to 10-membered bicyclic heterocycle), —($H_2NC(O)$)-substituted aryl, —($H_2NC(O)$)-substituted pyridyl, —C(O)OH, —C(O)O—($C_1$–$C_5$ alkyl), —C(O)O-phenyl or —C(NH)$NH_2$, each of which is unsubstituted or substituted with one or more of —O—($C_1$–$C_5$ alkyl), -halo, halo-substituted-($C_1$–$C_5$ alkyl), HO-substituted-($C_1$–$C_5$ alkyl), amino-substituted-($C_1$–$C_5$ alkyl), -hydroxy, —$NO_2$, —$NH_2$, —CN, —NH($C_1$–$C_5$ alkyl), —N($C_1$–$C_5$ alkyl)($C_1$–$C_5$ alkyl), -(-(nitrogen-containing 3- to 7-membered monocyclic heterocycle)), 7- to 10-membered bicycloheterocyclic amine, —$C_1$–$C_{10}$ alkyl, —$C_2$–$C_{10}$ alkenyl, —$C_2$–$C_{10}$ alkynyl, -aryl, -benzyl, —($H_2$NC(O))-substituted($C_1$–$C_5$ alkyl), carboxy-substituted-($C_1$–$C_5$ alkyl), —C(O)OH, —$C_1$–$C_5$-alkylene-C(O)O—($C_1$–$C_5$ alkyl) or —$C_1$–$C_5$ alkylene-OC(O)—($C_1$–$C_5$ alkyl); and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form a -(nitrogen-containing 3- to 7-membered monocyclic heterocycle) or a -(nitrogen-containing 7- to 10-membered bicyclic heterocycle); or N, $Z_1$ and $Z_2$ are taken together to form a -(nitrogen-containing 3- to 7-membered monocyclic heterocycle), or a -(nitrogen-containing 7- to 10-membered bicyclic heterocycle).

The invention also relates to compounds of Formula (IIa):

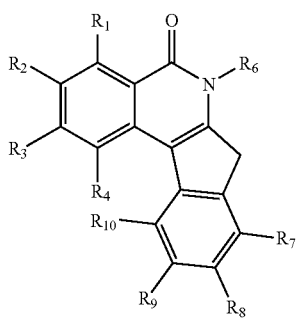

(IIa)

and pharmaceutically acceptable salts and hydrates thereof, wherein:

$R_6$ is —H or $C_1$–$C_4$ alkyl;

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, halo-substituted-($C_1$–$C_5$ alkyl), —$C_2$–$C_{10}$ alkenyl, —$C_3$–$C_8$-cycloalkyl, -aryl, —$NH_2$, amino-substituted-($C_1$–$C_5$ alkyl), —C(O)OH, —C(O)O($C_1$–$C_5$ alkyl), —OC(O)($C_1$–$C_5$ alkyl), $NO_2$ or -A-B;

A is —$SO_2$—, —$SO_2$NH—, —NHCO—, —NHCONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —$C_3$–$C_8$ cycloalkyl, -aryl, —$NZ_1Z_2$, —($C_1$–$C_5$ alkylene)-$NZ_1Z_2$, amino-substituted-($C_1$–$C_5$ alkyl), —N($C_1$–$C_5$ alkyl)($C_1$–$C_5$ alkyl), —($C_1$–$C_5$ alkyl)-(3- to 7-membered monocyclic heterocycle, or —($C_1$–$C_5$ alkyl)-(7- to 10-membered bicyclic heterocycle), —($H_2$NC(O))-substituted aryl, —($H_2$NC(O))-substituted pyridyl, —C(O)OH, —C(O)O—($C_1$–$C_5$ alkyl), —C(O)O-phenyl or —C(NH)$NH_2$, each of which is unsubstituted or substituted with one or more of —O—($C_1$–$C_5$ alkyl), -halo, halo-substituted-($C_1$–$C_5$ alkyl), HO-substituted-($C_1$–$C_5$ alkyl), amino-substituted-($C_1$–$C_5$ alkyl), -hydroxy, —$NO_2$, —$NH_2$, —CN, —NH($C_1$–$C_5$ alkyl), —N($C_1$–$C_5$ alkyl)($C_1$–$C_5$ alkyl), -(-(nitrogen-containing 3- to 7-membered monocyclic heterocycle)), 7- to 10-membered bicycloheterocyclic amine, —$C_1$–$C_{10}$ alkyl, —$C_2$–$C_{10}$ alkenyl, —$C_2$–$C_{10}$ alkynyl, -aryl, -benzyl, —($H_2$NC(O))-substituted($C_1$–$C_5$ alkyl), carboxy-substituted-($C_1$–$C_5$ alkyl), —C(O)OH, —$C_1$–$C_5$-alkylene-C(O)O—($C_1$–$C_5$ alkyl) or —$C_1$–$C_5$ alkylene-OC(O)—($C_1$–$C_5$ alkyl); and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form a -(nitrogen-containing 3- to 7-membered monocyclic heterocycle) or a -(nitrogen-containing 7- to 10-membered bicyclic heterocycle); or N, $Z_1$ and $Z_2$ are taken together to form a -(nitrogen-containing 3- to 7-membered monocyclic heterocycle), or a -(nitrogen-containing 7- to 10-membered bicyclic heterocycle).

The invention further relates to compounds of Formula (III):

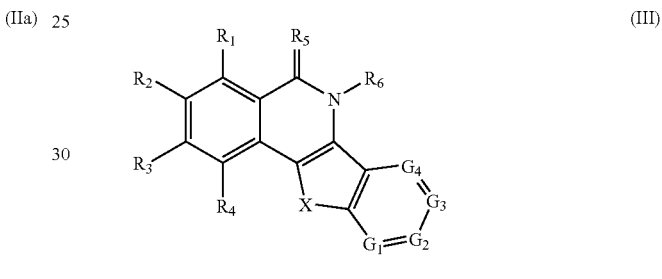

(III)

and pharmaceutically acceptable salts and hydrates thereof, wherein:

$R_5$ is O, NH or S;

$R_6$ is —H or —$C_1$–$C_4$ alkyl;

X is —C(O)—, —$CH_2$—, —CH(halo)-, —C(OH)(($CH_2$)$_n$$CH_3$))—, —C(OH)(aryl))-, —O—, —NH—, —S—, —CH(N$R_{11}$$R_{12}$)— or —N($SO_2$Y)—, wherein Y is —OH, —$NH_2$, —$C_1$–$C_5$ alkyl)-(3- to 7-membered monocyclic heterocycle), or —($C_1$–$C_5$ alkyl)-(7- to 10-membered bicyclic heterocycle) and n is an integer ranging from 0–5;

$R_{11}$ and $R_{12}$ are independently -hydrogen or —$C_1$–$C_9$ alkyl, or N, $R_{11}$ and $R_{12}$ are taken together to form a -(nitrogen-containing 3- to 7-membered monocyclic heterocycle), or a -(nitrogen-containing 7- to 10-membered bicyclic heterocycle);

one of $G_1$–$G_4$ is C—$R_7$ and the remaining $G_1$–$G_4$ are independently N or C—$R_7$;

$R_1$, $R_2$, $R_3$, and $R_4$ are independently -hydrogen, -halo, -hydroxy, —O—($C_1$–$C_5$ alkyl), —$C_1$–$C_{10}$ alkyl, halo-substituted-($C_1$–$C_5$ alkyl), —$C_2$–$C_{10}$ alkenyl, —$C_3$–$C_8$-cycloalkyl, -aryl, —$NH_2$, amino-substituted-($C_1$–$C_5$ alkyl), —C(O)OH, —C(O)O($C_1$–$C_5$ alkyl), —OC(O)($C_1$–$C_5$ alkyl), $NO_2$ or -A-B;

A is —$SO_2$—, —$SO_2$NH—, —NHCO—, —NHCONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —$C_3$–$C_8$ cycloalkyl, -aryl, —$NZ_1Z_2$, —($C_1$–$C_5$ alkylene)-$NZ_1Z_2$, amino-substituted-($C_1$–$C_5$ alkyl), —N($C_1$–$C_5$ alkyl)($C_1$–$C_5$ alkyl), —($C_1$–$C_5$ alkyl)-(3- to 7-membered monocyclic heterocycle), or —$C_1$–$C_5$ alkyl)-(7- to 10-membered bicyclic heterocycle), —($H_2$NC(O))-substituted aryl, —($H_2$NC(O))-substituted pyridyl, —C(O)OH, —C(O)O—($C_1$–$C_5$ alkyl), —C(O)O-phenyl or —C(NH)$NH_2$, each of which is unsubstituted or substituted with one or more of —O—($C_1$–$C_5$ alkyl), -halo, halo-substituted-($C_1$–$C_5$ alkyl), HO-substituted-($C_1$–$C_5$ alkyl), amino-substituted-($C_1$–$C_5$ alkyl), -hydroxy, —$NO_2$, —$NH_2$, —CN, —NH($C_1$–$C_5$ alkyl), —N($C_1$–$C_5$ alkyl)($C_1$–$C_5$ alkyl), -(-(nitrogen-containing 3- to 7-membered monocyclic heterocycle)), 7- to 10-membered bicycloheterocyclic amine, —$C_1$–$C_{10}$ alkyl, —$C_2$–$C_{10}$ alkenyl, —$C_2$–$C_{10}$ alkynyl, -aryl, -benzyl, —($H_2$NC(O))-substituted($C_1$–$C_5$ alkyl), carboxy-substituted-($C_1$–$C_5$ alkyl), —C(O)OH, —$C_1$–$C_5$-alkylene-C(O)O—($C_1$–$C_5$ alkyl) or —$C_1$–$C_5$ alkylene-OC(O)—($C_1$–$C_5$ alkyl); and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form a -(nitrogen-containing 3- to 7-membered monocyclic heterocycle) or a -(nitrogen-containing 7- to 10-membered bicyclic heterocycle); or N, $Z_1$ and $Z_2$ are taken together to form a -(nitrogen-containing 3- to 7-membered monocyclic heterocycle), or a -(nitrogen-containing 7- to 10-membered bicyclic heterocycle);

each $R_7$ is independently —H, —$C_1$–$C_6$ alkyl, —O—($C_1$–$C_6$ alkyl), —S—($C_1$–$C_6$ alkyl), —$SO_2$NH($C_1$–$C_6$ alkyl) or C(O)NH—($C_1$–$C_6$ alkyl).

The invention further relates to compounds of Formula (IV):

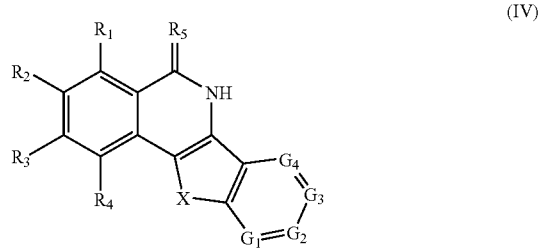

(IV)

and pharmaceutically acceptable salts and hydrates thereof, wherein:

$R_5$ is O, NH or S;

X is —C(O)—, —$CH_2$—, —CH(halo)-, —CH(OH)—, —(C(OH)(($CH_2$)$_m$$CH_3$))—, —(C(OH)(aryl))-, —O—, —N($Z_5$)—, —S—, —CH(N$R_{11}$$R_{12}$)— or —N($SO_2$Y)—, wherein Y is —OH, —$NH_2$, —($C_1$–$C_5$ alkyl)-(3- to 7-membered monocyclic heterocycle), or —($C_1$–$C_5$ alkyl)-(7- to 10-membered bicyclic heterocycle) and m is an integer ranging from 0–5;

$R_{11}$ and $R_{12}$ are independently -hydrogen or —$C_1$–$C_9$ alkyl, or N, $R_{11}$ and $R_{12}$ are taken together to form a -(nitrogen-containing 3- to 7-membered monocyclic heterocycle), or a -(nitrogen-containing 7- to 10-membered bicyclic heterocycle);

one of $G_1$–$G_4$ is C—$R_7$ and the remaining $G_1$–$G_4$ are independently N or C—$R_7$;

$R_1$, $R_2$, $R_3$, and $R_4$ are independently -hydrogen, -halo, -hydroxy, —O—($C_1$–$C_5$ alkyl), —$C_1$–$C_{10}$ alkyl, halo-substituted-($C_1$–$C_5$ alkyl), —$C_2$–$C_{10}$ alkenyl, —$C_3$–$C_8$-cycloalkyl, -aryl, —$NH_2$, amino-substituted-($C_1$–$C_5$ alkyl), —C(O)OH, —C(O)O($C_1$–$C_5$ alkyl), —OC(O)($C_1$–$C_5$ alkyl), $NO_2$ or -A-B;

A is —$SO_2$—, —$SO_2$NH—, —NHCO—, —NH-CONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —$C_3$–$C_8$ cycloalkyl, -aryl, —$NZ_1Z_2$, —($C_1$–$C_5$ alkylene)-$NZ_1Z_2$, amino-substituted-($C_1$–$C_5$ alkyl), —N($C_1$–$C_5$ alkyl)($C_1$–$C_5$ alkyl), —($C_1$–$C_5$ alkyl)-(3- to 7-membered monocyclic heterocycle), or —($C_1$–$C_5$ alkyl)-(7- to 10-membered bicyclic heterocycle), —($H_2$NC(O))-substituted aryl, —($H_2$NC(O))-substituted pyridyl, —C(O)OH, —C(O)O—($C_1$–$C_5$ alkyl), —C(O)O-phenyl or —C(NH)$NH_2$, each of which is unsubstituted or substituted with one or more of —O—($C_1$–$C_5$ alkyl), -halo, halo-substituted-($C_1$–$C_5$ alkyl), HO-substituted-($C_1$–$C_5$ alkyl), amino-substituted-($C_1$–$C_5$ alkyl), -hydroxy, —$NO_2$, —$NH_2$, —CN, —NH($C_1$–$C_5$ alkyl), —N($C_1$–$C_5$ alkyl)($C_1$–$C_5$ alkyl), -(-(nitrogen-containing 3- to 7-membered monocyclic heterocycle)), 7- to 10-membered bicycloheterocyclic amine, —$C_1$–$C_{10}$ alkyl, —$C_2$–$C_{10}$ alkenyl, —$C_2$–$C_{10}$ alkynyl, -aryl, -benzyl, —($H_x$NC(O))-substituted($C_1$–$C_5$ alkyl), carboxy-substituted-($C_1$–$C_5$ alkyl), —C(O)OH, —$C_1$–$C_5$-alkylene-C(O)O—($C_1$–$C_5$ alkyl) or —$C_1$–$C_5$ alkylene-OC(O)—($C_1$–$C_5$ alkyl);

$Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form a (nitrogen-containing 3- to 7-membered monocyclic hetero cycle) or a -(nitrogen-containing 7- to 10-membered bicyclic heterocycle); or N, $Z_1$ and $Z_2$ are taken together to form a -(nitrogen-containing 3- to 7-membered monocyclic heterocycle), or a -(nitrogen-containing 7- to 10-membered bicyclic heterocycle);

each $R_7$ is independently —H, —$C_1$–$C_6$ alkyl, —O—($C_1$–$C_6$ alkyl), —S—($C_1$–$C_6$ alkyl), —$SO_2$NH($C_1$–$C_6$ alkyl) or C(O)NH—($C_1$–$C_6$ alkyl);

$Z_5$ is —H, —$C_1$–$C_5$ alkyl, —($CH_2$)$_n$—CN, —($CH_2$)$_n$-aryl, —($CH_2$)$_n$-(3- to 7-membered monocyclic heterocycle), —($CH_2$)$_n$-(7- to 10-membered bicyclic heterocycle), —($CH_2$)$_n$—COO—($C_1$–$C_5$ alkyl), —($CH_2$), —COO-aryl, —($CH_2$)$_n$—COOH, —CONH—($CH_2$)$_n$—COOH, —CONH—($CH_2$)$_n$—COO—($C_1$–$C_5$ alkyl), —CONH—($CH_2$)$_n$-aryl, —CONHNH—($C_1$–$C_5$ alkyl), —CONHNH-aryl, —($CH_2$)$_n$—$CONH_2$, —($CH_2$)$_n$—CONH—($C_1$–$C_5$ alkyl), —($CH_2$)$_n$—CONH-aryl, —($CH_2$)$_n$—CONH—($CH_2$)$_q$-aryl, —($CH_2$)$_n$—CONH—($CH_2$)$_q$-(3- to 7-membered monocyclic heterocycle), —($CH_2$)$_n$—CONH—($CH_2$)$_q$-(3- to 7-membered monocyclic heterocycle), —($CH_2$)$_n$—CONH—($CH_2$)$_q$—$CONH_2$—($CH_2$)$_n$—CONH—($CH_2$)$_q$—CONH—($C_1$–$C_5$ alkyl), —($CH_2$)$_n$—CONH—($CH_2$)$_q$—CON($C_1$–$C_5$ alkyl)$_2$, —C(O)($CH_2$)$_n$—($C_1$–$C_5$ alkyl), —C(O)($CH_2$)$_n$-aryl, —C(O)($CH_2$)$_n$—COOH, —C(O)($CH_2$)$_n$—COO—($C_1$–$C_5$alkyl), —C(O)($CH_2$)$_n$—COO-(3- to 7-membered monocyclic heterocycle), —C(O)($CH_2$), —COO-(7- to 10-membered bicyclic heterocycle), —C(O)(CH$_2$)$_n$-phenyl, —C(O)(CH$_2$)$_n$-(3- to 7-membered monocyclic heterocycle), —C(O)(CH$_2$)$_n$-phenyl, —C(O)(CH$_2$)$_n$-(7- to 10-membered bicyclic heterocycle), —C(O)O(CH$_2$)$_n$-phenyl, —C(O)O(CH$_2$)$_n$-(3- to 7-membered monocyclic heterocycle), —C(O)(CH$_2$)$_n$-phenyl, —C(O)(CH$_2$)$_q$-(7- to 10-membered bicyclic heterocycle), —C(O)N((CH$_2$)$_n$-phenyl)$_2$, —C(O)N((CH$_2$)$_n$-phenyl)((CH$_2$)$_{q-3}$- to 7-membered monocyclic heterocycle), —C(O)N((CH$_2$)$_n$-phenyl)((CH$_2$)$_{q-7}$- to 10-membered bicyclic heterocycle), —C(O)N((CH$_2$)$_n$-(3- to 7-membered monocyclic heterocycle)$_2$, —C(O)N((CH$_2$)$_{n-7}$- to 10-membered bicyclic heterocycle)$_2$, or —SO$_2$NH$_2$;

each n is an integer ranging from 0 to 10; and q is an integer ranging from 0 to 10.

The invention also relates to compounds of Formula (V):

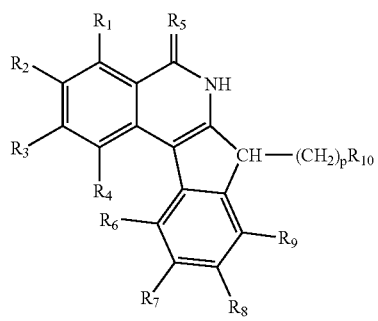

(V)

and pharmaceutically acceptable salts and hydrates thereof, wherein:

R$_5$ is O, S, or NH;

R$_1$, R$_2$, R$_3$, R$_4$, R$_6$, R$_7$, R$_8$, and R$_9$ are independently -hydrogen, -halo, -hydroxy, —NH$_2$ NO$_2$, or -A-B;

A is —SO$_2$—, —SO$_2$NH—, —NHCO—, —NHCONH—, —O—, —CO—, —OC(O)—, —C(O)O—, —CONH—, —CON(C$_1$-C$_4$ alkyl)-, —NH—, —CH$_2$—, —S— or —C(S)—;

B is —C$_1$-C$_{10}$ alkyl, —C$_2$-C$_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —C$_3$-C$_8$ cycloalkyl, -aryl, —NZ$_1$Z$_2$, —(C$_1$-C$_5$ alkylene)-NZ$_1$Z$_2$, amino-substituted-(C$_1$-C$_5$ alkyl), —N(C$_1$-C$_5$ alkyl)(C$_1$-C$_5$ alkyl), —(C$_1$-C$_5$ alkyl)-(3- to 7-membered monocyclic heterocycle), or —(C$_1$-C$_5$ alkyl)-(7- to 10-membered bicyclic heterocycle), —(H$_2$NC(O))-substituted aryl, —(H$_2$NC(O))-substituted pyridyl, —C(O)OH, —C(O)O—(C$_1$-C$_5$ alkyl), —C(O)O-phenyl or —C(NH)NH$_2$, each of which is unsubstituted or substituted with one or more of —O—(C$_1$-C$_5$ alkyl), -halo, halo-substituted-(C$_1$-C$_5$ alkyl), HO-substituted-(C$_1$-C$_5$ alkyl), amino-substituted-(C$_1$-C$_5$ alkyl), -hydroxy, —NO$_2$, —NH$_2$, —CN, —NH(C$_1$-C$_5$ alkyl), —N(C$_1$-C$_5$ alkyl)(C$_1$-C$_5$ alkyl), -(-(nitrogen-containing 3- to 7-membered monocyclic heterocycle)), 7- to 10-membered bicycloheterocyclic amine, —C$_1$-C$_{10}$ alkyl, —C$_2$-C$_{10}$ alkenyl, —C$_2$-C$_{10}$ alkynyl, -aryl, -benzyl, —(H$_2$NC(O))-substituted(C$_1$-C$_5$ alkyl), carboxy-substituted-(C$_1$-C$_5$ alkyl), —C(O)OH, —C$_1$-C$_5$-alkylene-C(O)O—(C$_1$-C$_5$ alkyl) or —C$_1$-C$_5$ alkylene-OC(O)—(C$_1$-C$_5$ alkyl); and Z$_1$ and Z$_2$ are independently —H or —C$_1$-C$_{10}$ alkyl, which is unsubstituted or substituted with one or more of -halo, —OH or —N(Z$_3$)(Z$_4$), where Z$_3$ and Z$_4$ are independently, —H or —C$_1$-C$_5$ alkyl, which is unsubstituted or substituted with one or more of -halo, -hydroxy or —NH$_2$; or N, Z$_3$ and Z$_4$ are taken together to form a -(nitrogen-containing 3- to 7-membered monocyclic heterocycle) or a -(nitrogen-containing 7- to 10-membered bicyclic heterocycle); or N, Z$_1$ and Z$_2$ are taken together to form a -(nitrogen-containing 3- to 7-membered monocyclic heterocycle), or a -(nitrogen-containing 7- to 10-membered bicyclic heterocycle);

R$_{10}$ is —H, —C$_1$-C$_5$ alkyl, —(CH$_2$)$_n$—CN, —(CH$_2$)$_n$-aryl, —(CH$_2$)$_n$-(3- to 7-membered monocyclic heterocycle), —(CH$_2$)$_{n-7}$- to 10-membered bicyclic heterocycle), —(CH$_2$)$_n$—COO—(C$_1$-C$_5$ alkyl), —(CH$_2$), —COO-aryl, —(CH$_2$)$_n$—COOH, —CONH—(CH$_2$)$_n$—COOH, —CONH—(CH$_2$)$_n$—COO—(C$_1$-C$_5$ alkyl), —CONH—(CH$_2$)$_n$-aryl, —CONHNH—(C$_1$-C$_5$ alkyl), —CONHNH-aryl, —(CH$_2$)$_n$—CONH$_2$, —(CH$_2$)$_n$—CONH—(C$_1$-C$_5$ alkyl), —(CH$_2$)$_n$—CONH-aryl, —(CH$_2$)$_n$—CONH—(CH$_2$)$_q$-aryl, —(CH$_2$)$_n$—CONH—(CH$_2$)$_q$-(3- to 7-membered monocyclic heterocycle), —(CH$_2$)$_n$—CONH—(CH$_2$)$_q$-(3- to 7-membered monocyclic heterocycle), —(CH$_2$)$_n$—CONH—(CH$_2$)$_q$—CONH$_2$—(CH$_2$)$_n$—CONH—(CH$_2$)$_q$—CONH—(C$_1$-C$_5$ alkyl), —(CH$_2$)$_n$—CONH—(CH$_2$)$_q$—CON(C$_1$-C$_5$ alkyl)$_2$, —C(O)(CH$_2$)$_n$—(C$_1$-C$_5$ alkyl), —C(O)(CH$_2$)$_n$-aryl, —C(O)(CH$_2$)$_n$—COOH, —C(O)(CH$_2$)$_n$—COO—(C$_1$-C$_5$alkyl), —C(O)(CH$_2$)$_n$—COO-(3- to 7-membered monocyclic heterocycle), —C(O)(CH$_2$)$_n$—COO-(7- to 10-membered bicyclic heterocycle), —C(O)(CH$_2$)$_n$-phenyl, —C(O)(CH$_2$)$_n$-(3- to 7-membered monocyclic heterocycle), —C(O)(CH$_2$)$_n$-phenyl, —C(O)(CH$_2$)$_n$-(7- to 10-membered bicyclic heterocycle), —C(O)O(CH$_2$)$_n$-phenyl, —C(O)O(CH$_2$)$_n$-(3- to 7-membered monocyclic heterocycle), —C(O)(CH$_2$)$_n$-phenyl, —C(O)(CH$_2$)$_n$-(7- to 10-membered bicyclic heterocycle), —C(O)N((CH$_2$)$_n$-phenyl)$_2$, —C(O)N((CH$_2$)$_n$-phenyl)((CH$_2$)$_{q-3}$- to 7-membered monocyclic heterocycle), —C(O)N((CH$_2$)$_n$-phenyl)((CH$_2$)$_{n-7}$- to 10-membered bicyclic heterocycle), —C(O)N((CH$_2$)$_n$-(3- to 7-membered monocyclic heterocycle)$_2$, —C(O)N((CH$_2$)$_{n-7}$- to 10-membered bicyclic heterocycle)$_2$, or —SO$_2$NH$_2$;

each n is an integer ranging from 0 to 10;

p is an integer ranging from 0 to 5, with p being other than 0 when R$_{10}$ is —H; and q is an integer ranging from 0 to 10.

The invention also relates to compounds of Formula (VI):

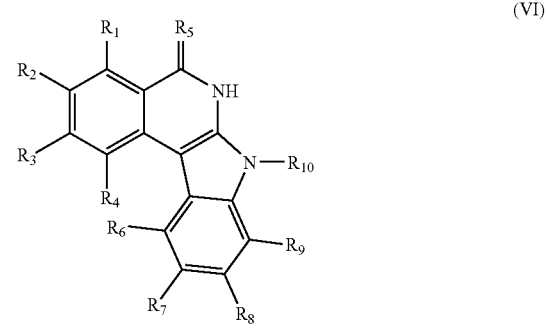

(VI)

and pharmaceutically acceptable salts and hydrates thereof, wherein:

R$_5$ is O, S, or NH;

$R_1$, $R_2$, $R_3$, $R_4$, $R_6$, $R_7$, $R_8$, and $R_9$ are independently -hydrogen, -halo, -hydroxy, —$NH_2$ $NO_2$, or -A-B;

A is —$SO_2$—, —$SO_2NH$—, —NHCO—, —NH-CONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —$C_3$–$C_8$ cycloalkyl, -aryl, —$NZ_1Z_2$, —($C_1$–$C_5$ alkylene)-$NZ_1Z_2$, amino-substituted-($C_1$–$C_5$ alkyl), —N($C_1$–$C_5$ alkyl)($C_1$–$C_5$ alkyl), —($C_1$–$C_5$ alkyl)-(3- to 7-membered monocyclic heterocycle), or —($C_1$–$C_5$ alkyl)-(7- to 10-membered bicyclic heterocycle), —($H_2NC(O)$)-substituted aryl, —($H_2NC(O)$)-substituted pyridyl, —C(O)OH, —C(O)O—($C_1$–$C_5$ alkyl), —C(O)O-phenyl or —C(NH)$NH_2$, each of which is unsubstituted or substituted with one or more of —O—($C_1$–$C_5$ alkyl), -halo, halo-substituted-($C_1$–$C_5$ alkyl), HO-substituted-($C_1$–$C_5$ alkyl), amino-substituted-($C_{11}$–$C_5$ alkyl), -hydroxy, —$NO_2$, —$NH_2$, —CN, —NH($C_1$s-$C_5$ alkyl), —N($C_1$–$C_5$ alkyl)($C_1$–$C_5$ alkyl), -(nitrogen-containing 3- to 7-membered monocyclic heterocycle), 7- to 10-membered bicycloheterocyclic amine, —$C_1$–$C_{10}$ alkyl, —$C_2$–$C_{10}$ alkenyl, —$C_2$–$C_{10}$ alkynyl, -aryl, -benzyl, —($H_2NC(O)$)-substituted($C_1$–$C_5$ alkyl), carboxy-substituted-($C_1$–$C_5$ alkyl), —C(O)OH, —$C_1$–$C_5$-alkylene-C(O)O—($C_1$–$C_5$ alkyl) or —$C_1$–$C_5$ alkylene-OC(O)—($C_1$–$C_5$ alkyl);

$Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form a (nitrogen-containing 3- to 7-membered monocyclic heterocycle) or a -(nitrogen-containing 7- to 10-membered bicyclic heterocycle); or N, $Z_1$ and $Z_2$ are taken together to form a -(nitrogen-containing 3- to 7-membered monocyclic heterocycle), or a -(nitrogen-containing 7- to 10-membered bicyclic heterocycle);

$R_{10}$ is —H, —$C_1$–$C_5$ alkyl, —$(CH_2)_n$—CN, —$(CH_2)_n$-aryl, —$(CH_2)_n$-(3- to 7-membered monocyclic heterocycle), —$(CH_2)_n$-(7- to 10-membered bicyclic heterocycle), —$(CH_2)_n$—COO—($C_1$–$C_5$ alkyl), —$(CH_2)_n$—COO-aryl, —$(CH_2)_n$—COOH, —CONH—$(CH_2)_n$—COOH, —CONH—$(CH_2)_n$—COO—($C_1$–$C_5$ alkyl), —CONH—$(CH_2)_n$-aryl, —CONHNH—($C_1$–$C_5$ alkyl), —CONHNH-aryl, —$(CH_2)_n$—$CONH_2$, —$(CH_2)_n$—CONH—($C_1$–$C_5$ alkyl), —$(CH_2)$, —CONH-aryl, —$(CH_2)_n$—CONH—$(CH_2)_q$-aryl, —$(CH_2)_n$—CONH—$(CH_2)_q$-(3- to 7-membered monocyclic heterocycle), —$(CH_2)_{11}$—CONH—$(CH_2)_q$-(3- to 7-membered monocyclic heterocycle), —$(CH_2)_n$—CONH—$(CH_2)_q$—$CONH_2$—$(CH_2)_n$—CONH—$(CH_2)_q$—CONH—($C_1$–$C_5$ alkyl), —$(CH_2)_n$—CONH—$(CH_2)_q$—CON($C_1$–$C_5$ alkyl)$_2$, —$C(O)(CH_2)_n$—($C_1$–$C_5$ alkyl), —$C(O)(CH_2)_n$-aryl, —$C(O)(CH_2)_n$—COOH, —$C(O)(CH_2)_n$—COO—($C_1$–$C_5$alkyl), —$C(O)(CH_2)_n$—COO-(3- to 7-membered monocyclic heterocycle), —$C(O)(CH_2)_n$—COO-(7- to 10-membered bicyclic heterocycle), —$C(O)(CH_2)_n$-phenyl, —$C(O)(CH_2)_n$-(3- to 7-membered monocyclic heterocycle), —$C(O)(CH_2)_n$-phenyl, —$C(O)(CH_2)_n$-(7- to 10-membered bicyclic heterocycle), —$C(O)O(CH_2)_n$-phenyl, —$C(O)O(CH_2)_n$-(3- to 7-membered monocyclic heterocycle), —$C(O)(CH_2)_n$-phenyl, —$C(O)(CH_2)_n$-(7- to 10-membered bicyclic heterocycle), —$C(O)N((CH_2)_n$-phenyl)$_2$, —$C(O)N((CH_2)_n$-phenyl)($(CH_2)_q$-3- to 7-membered monocyclic heterocycle), —$C(O)N((CH_2)_n$-phenyl) $((CH_2)_q$7- to 10-membered bicyclic heterocycle), —C(O)N $((CH_2)_n$-(3- to 7-membered monocyclic heterocycle)$_2$, —$C(O)N((CH_2)_n$-7- to 10-membered bicyclic heterocycle)$_2$, or —$SO_2NH_2$;

each n is an integer ranging from 0 to 10; and q is an integer ranging from 0 to 10.

The invention also relates to compounds of Formula (VII):

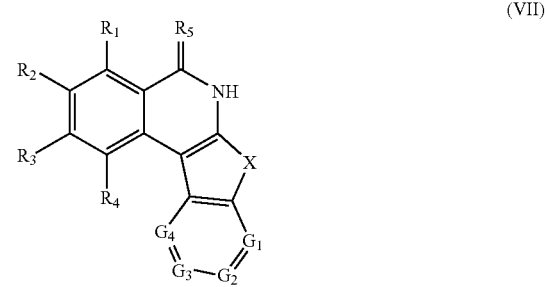

(VII)

and pharmaceutically acceptable salts and hydrates thereof, wherein $R_5$ is O, NH or S;

X is —C(O)—, —$CH_2$—, —CH(halo)-, —CH(OH)—, —$(C(OH)((CH_2)_nCH_3))$—, —(C(OH)(aryl))-, —O—, —N($Z_5$)—, —S—, —CH($NR_{11}R_{12}$)— or —N($SO_2$Y)—, wherein Y is —OH, —$NH_2$, —$C_1$–$C_5$ alkyl)-(3- to 7-membered monocyclic heterocycle), or —($C_1$–$C_5$ alkyl)-(7- to 10-membered bicyclic heterocycle) and m is an integer ranging from 0–5;

$R_{11}$ and $R_{12}$ are independently -hydrogen or —$C_1$–$C_9$ alkyl, or N, $R_{11}$ and $R_{12}$ are taken together to form a -(nitrogen-containing 3- to 7-membered monocyclic heterocycle), or a -(nitrogen-containing 7- to 10-membered bicyclic heterocycle);

one of $G_1$–$G_4$ is C—$R_7$ and the remaining $G_1$–$G_4$ are independently N or C—$R_7$;

$R_1$, $R_2$, $R_3$, and $R_4$ are independently -hydrogen, -halo, -hydroxy, —O—($C_1$–$C_5$ alkyl), —$C_1$–$C_{10}$ alkyl, halo-substituted-($C_1$–$C_5$ alkyl), —$C_2$–$C_{10}$ alkenyl, —$C_3$–$C_8$-cycloalkyl, -aryl, —$NH_2$, amino-substituted-($C_1$–$C_5$ alkyl), —C(O)OH, —C(O)O($C_1$–$C_5$ alkyl), —OC(O)($C_1$–$C_5$ alkyl), $NO_2$ or -A-B;

A is —$SO_2$—, —$SO_2NH$—, —NHCO—, —NH-CONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —$C_3$–$C_8$ cycloalkyl, -aryl, —$NZ_1Z_2$, —($C_1$–$C_5$ alkylene)-$NZ_1Z_2$, amino-substituted-($C_1$–$C_5$ alkyl), —N($C_1$–$C_5$ alkyl)($C_1$–$C_5$ alkyl), —($C_1$–$C_5$ alkyl)-(3- to 7-membered monocyclic heterocycle), or —(C$_1$–C$_5$ alkyl)-(7- to 10-membered bicyclic heterocycle), —(H$_2$NC(O))-substituted aryl, —(H$_2$NC(O))-substituted pyridyl, —C(O)OH, —C(O)O—(C$_1$–C$_5$ alkyl), —C(O)O-phenyl or —C(NH)NH$_2$, each of which is unsubstituted or substituted with one or more of —O—(C$_1$–C$_5$ alkyl), -halo, halo-substituted-(C$_1$–C$_5$ alkyl), HO-substituted-(C$_1$–C$_5$ alkyl), amino-substituted-(C$_1$–C$_5$ alkyl), -hydroxy, —NO$_2$, —NH$_2$, —CN, —NH(C$_1$–C$_5$ alkyl), —N(C$_1$–C$_5$ alkyl)(C$_1$–C$_5$ alkyl), -(nitrogen-containing 3- to 7-membered monocyclic heterocycle), 7- to 10-membered bicycloheterocyclic amine, —C$_1$–C$_{10}$ alkyl, —C$_2$–C$_{10}$ alkenyl, —C$_2$–C$_{10}$ alkynyl, -aryl, -benzyl, —(H$_2$NC(O))-substituted(C$_1$–C$_5$ alkyl), carboxy-substituted-(C$_1$–C$_5$ alkyl), —C(O)OH, —C$_1$–C$_5$-alkylene-C(O)O—(C$_1$–C$_5$ alkyl) or —C$_1$–C$_5$ alkylene-OC(O)—(C$_1$–C$_5$ alkyl);

Z$_1$ and Z$_2$ are independently —H or —C$_1$–C$_{10}$ alkyl, which is unsubstituted or substituted with one or more of -halo, —OH or —N(Z$_3$)(Z$_4$), where Z$_3$ and Z$_4$ are independently, —H or —C$_1$–C$_5$ alkyl, which is unsubstituted or substituted with one or more of -halo, -hydroxy or —NH$_2$; or N, Z$_3$ and Z$_4$ are taken together to form a -(nitrogen-containing 3- to 7-membered monocyclic heterocycle) or a -(nitrogen-containing 7- to 10-membered bicyclic heterocycle); or N, Z$_1$ and Z$_2$ are taken together to form a -(nitrogen-containing 3- to 7-membered monocyclic heterocycle), or a -(nitrogen-containing 7- to 10-membered bicyclic heterocycle);

each R$_7$ is independently —H, —C$_1$–C$_6$ alkyl, —O—(C$_1$–C$_6$ alkyl), —S—(C$_1$–C$_6$ alkyl), —SO$_2$NH(C$_1$–C$_6$ alkyl) or C(O)NH—(C$_1$–C$_6$ alkyl);

Z$_5$ is —H, —C$_1$–C$_5$ alkyl, —(CH$_2$)$_n$—CN, —(CH$_2$)$_n$-aryl, —(CH$_2$)$_n$-(3- to 7-membered monocyclic heterocycle), —(CH$_2$)$_n$-(7- to 10-membered bicyclic heterocycle), —(CH$_2$)$_n$—COO—(C$_1$–C$_5$ alkyl), —(CH$_2$)$_n$—COO-aryl, —(CH$_2$)$_n$—COOH, —CONH—(CH$_2$)$_n$—COOH, —CONH—(CH$_2$)$_n$—COO—(C$_1$–C$_5$ alkyl), —CONH—(CH$_2$)$_n$-aryl, —CONHNH—(C$_1$–C$_5$ alkyl), —CONHNH-aryl, —(CH$_2$)$_n$—CONH$_2$, —(CH$_2$)$_n$—CONH—(C$_1$–C$_5$ alkyl), —(CH$_2$)$_n$—CONH-aryl, —(CH$_2$)$_n$—CONH—(CH$_2$)$_q$-aryl, —(CH$_2$)$_n$—CONH—(CH$_2$)$_q$-(3- to 7-membered monocyclic heterocycle), —(CH$_2$)$_n$—CONH—(CH$_2$)$_q$-(3- to 7-membered monocyclic heterocycle), —(CH$_2$)$_n$—CONH—(CH$_2$)$_q$—CONH$_2$—(CH$_2$)$_n$—CONH—(CH$_2$)$_q$—CONH—(C$_1$–C$_5$ alkyl), —(CH$_2$)$_n$—CONH—(CH$_2$)$_q$—CON(C$_1$–C$_5$ alkyl)$_2$, —C(O)(CH$_2$)$_n$—(C$_1$–C$_5$ alkyl), —C(O)(CH$_2$)$_n$-aryl, —C(O)(CH$_2$)$_n$—COOH, —C(O)(CH$_2$)$_n$—COO—(C$_1$–C$_5$alkyl), —C(O)(CH$_2$)$_n$—COO-(3- to 7-membered monocyclic heterocycle), —C(O)(CH$_2$)$_n$—COO-(7- to 10-membered bicyclic heterocycle), —C(O)(CH$_2$)$_n$-phenyl, —C(O)(CH$_2$)$_n$-(3- to 7-membered monocyclic heterocycle), —C(O)(CH$_2$)$_n$-phenyl, —C(O)(CH$_2$)$_n$-(7- to 10-membered bicyclic heterocycle), —C(O)O(CH$_2$)$_n$-phenyl, —C(O)O(CH$_2$)$_n$-(3- to 7-membered monocyclic heterocycle), —C(O)(CH$_2$)$_n$-phenyl, —C(O)(CH$_2$)$_n$-(7- to 10-membered bicyclic heterocycle), —C(O)N((CH$_2$)$_n$-phenyl)$_2$, —C(O)N((CH$_2$)$_n$-phenyl)((CH$_2$)$_q$-3- to 7-membered monocyclic heterocycle), —C(O)N((CH$_2$)$_n$-phenyl)((CH$_2$)$_q$ 7- to 10-membered bicyclic heterocycle), —C(O)N((CH$_2$)$_n$-(3- to 7-membered monocyclic heterocycle)$_2$, —C(O)N((CH$_2$)$_{n-7}$- to 10-membered bicyclic heterocycle)$_2$, or —SO$_2$NH$_2$;

each n is an integer ranging from 0 to 10; and q is an integer ranging from 0 to 10.

The invention also relates to compounds of Formula (VIIa):

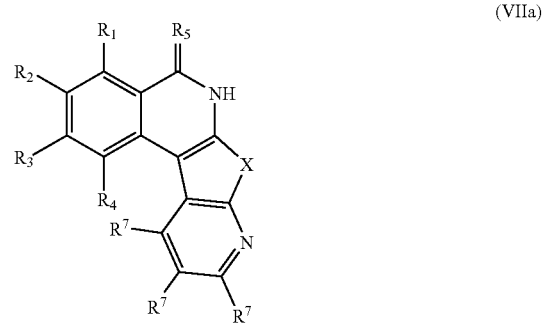

(VIIa)

and pharmaceutically acceptable salts and hydrates thereof, wherein

R$_5$ is O, NH or S;

X is —C(O)—, —CH$_2$—, —CH(halo)-, —CH(OH)—, —(C(OH)((CH$_2$)$_n$CH$_3$))—, —(C(OH)(aryl))-, —O—, —N(Z$_5$)—, —S—, —CH(NR$_{11}$R$_{12}$)— or —N(SO$_2$Y)—, wherein Y is —OH, —NH$_2$, —(C$_1$–C$_5$ alkyl)-(3- to 7-membered monocyclic heterocycle), or —(C$_1$–C$_5$ alkyl)-(7- to 10-membered bicyclic heterocycle) and m is an integer ranging from 0–5;

R$_{11}$ and R$_{12}$ are independently -hydrogen or —C$_1$–C$_9$ alkyl, or N, R$_{11}$ and R$_{12}$ are taken together to form a -(nitrogen-containing 3- to 7-membered monocyclic heterocycle), or a -(nitrogen-containing 7- to 10-membered bicyclic heterocycle);

R$_1$, R$_2$, R$_3$, and R$_4$ are independently -hydrogen, -halo, -hydroxy, —O—(C$_1$–C$_5$ alkyl), —C$_1$–C$_{10}$ alkyl, halo-substituted-(C$_1$–C$_5$ alkyl), —C$_2$–C$_{10}$ alkenyl, —C$_3$–C$_8$-cycloalkyl, -aryl, —NH$_2$, amino-substituted-(C$_1$–C$_5$ alkyl), —C(O)OH, —C(O)O(C$_1$–C$_5$ alkyl), —OC(O)(C$_1$–C$_5$ alkyl), NO$_2$ or -A-B;

A is —SO$_2$—, —SO$_2$NH—, —NHCO—, —NHCONH—, —O—, —CO—, —OC(O)—, —C(O)O—, —CONH—, —CON(C$_1$–C$_4$ alkyl)-, —NH—, —CH$_2$—, —S— or —C(S)—;

B is —C$_1$–C$_{10}$ alkyl, —C$_2$–C$_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —C$_3$–C$_8$ cycloalkyl, -aryl, —NZ$_1$Z$_2$, —(C$_1$–C$_5$ alkylene)-NZ$_1$Z$_2$, amino-substituted-(C$_1$–C$_5$ alkyl), —N(C$_1$–C$_5$ alkyl)(C$_1$–C$_5$ alkyl), —(C$_1$–C$_5$ alkyl)-(3- to 7-membered monocyclic heterocycle), or —(C$_1$–C$_5$ alkyl)-(7- to 10-membered bicyclic heterocycle), —(H$_2$NC(O))-substituted aryl, —(H$_2$NC(O))-substituted pyridyl, —C(O)OH, —C(O)O—(C$_1$–C$_5$ alkyl), —C(O)O-phenyl or —C(NH)NH$_2$, each of which is unsubstituted or substituted with one or more of —O—(C$_1$–C$_5$ alkyl), -halo, halo-substituted-(C$_1$–C$_5$ alkyl), HO-substituted-(C$_1$–C$_5$ alkyl), amino-substituted-(C$_1$–C$_5$ alkyl), -hydroxy, —NO$_2$, —NH$_2$, —CN, —NH(C$_1$–C$_5$ alkyl), —N(C$_1$–C$_5$ alkyl)(C$_1$–C$_5$ alkyl), -(nitrogen-containing 3- to 7-membered monocyclic heterocycle), 7- to 10-membered bicycloheterocyclic amine, —C$_1$–C$_{10}$ alkyl, —C$_2$–C$_{10}$ alkenyl, —C$_2$–C$_{10}$ alkynyl, -aryl, -benzyl, —(H$_2$NC(O))-substituted(C$_1$–C$_5$ alkyl), carboxy-substituted-(C$_1$–C$_5$ alkyl), —C(O)OH, —C$_1$–C$_5$-alkylene-C(O)O—(C$_1$–C$_5$ alkyl) or —C$_1$–C$_5$ alkylene-OC(O)—(C$_1$–C$_5$ alkyl); and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —NH$_2$; or N, $Z_3$ and $Z_4$ are taken together to form a -nitrogen-containing 3- to 7-membered monocyclic heterocycle) or a -(nitrogen-containing 7- to 10-membered bicyclic heterocycle); or N, $Z_1$ and $Z_2$ are taken together to form a -(nitrogen-containing 3- to 7-membered monocyclic heterocycle), or a -(nitrogen-containing 7- to 10-membered bicyclic heterocycle);

each $R_7$ is independently —H, —$C_1$–$C_6$ alkyl, —O—($C_1$–$C_6$ alkyl), —S—($C_1$–$C_6$ alkyl), —SO$_2$NH($C_1$–$C_6$ alkyl) or C(O)NH—($C_1$–$C_6$ alkyl);

$Z_5$ is —H, —$C_1$–$C_5$ alkyl, —(CH$_2$)$_n$—CN, —(CH$_2$)$_n$-aryl, —(CH$_2$)$_n$-(3- to 7-membered monocyclic heterocycle), —(CH$_2$)$_n$-(7- to 10-membered bicyclic heterocycle), —(CH$_2$)$_n$—COO—($C_1$–$C_5$ alkyl), —(CH$_2$)$_n$—COO-aryl, —(CH$_2$)$_n$—COOH, —CONH—(CH$_2$)$_n$—COOH, —CONH—(CH$_2$)$_n$—COO—($C_1$–$C_5$ alkyl), —CONH—(CH$_2$)$_n$-aryl, —CONHNH—($C_1$–$C_5$ alkyl), —CONHNH-aryl, —(CH$_2$)$_n$—CONH$_2$, —(CH$_2$)$_n$—CONH—($C_1$–$C_5$ alkyl), —(CH$_2$)$_n$—CONH-aryl, —(CH$_2$)$_n$—CONH—(CH$_2$)$_q$-aryl, —(CH$_2$)$_n$—CONH—(CH$_2$)$_q$-(3- to 7-membered monocyclic heterocycle), —(CH$_2$)$_n$—CONH—(CH$_2$)$_q$-(3- to 7-membered monocyclic heterocycle), —(CH$_2$)$_n$—CONH—(CH$_2$)$_q$—CONH$_2$—(CH$_2$)$_n$—CONH—(CH$_2$)$_q$—CONH—($C_1$–$C_5$ alkyl), —(CH$_2$)$_n$—CONH—(CH$_2$)$_q$—CON($C_1$–$C_5$ alkyl)$_2$, —C(O)(CH$_2$)$_n$—($C_1$–$C_5$ alkyl), —C(O)(CH$_2$)$_n$-aryl, —C(O)(CH$_2$)$_n$—COOH, —C(O)(CH$_2$)$_n$—COO—($C_1$–$C_5$alkyl), —C(O)(CH$_2$)$_n$—COO-(3- to 7-membered monocyclic heterocycle), —C(O)(CH$_2$)$_n$—COO-(7- to 10-membered bicyclic heterocycle), —C(O)(CH$_2$)$_n$-phenyl, —C(O)(CH$_2$)$_n$-(3- to 7-membered monocyclic heterocycle), —C(O)(CH$_2$)$_n$-phenyl, —C(O)(CH$_2$)$_n$-(7- to 10-membered bicyclic heterocycle), —C(O)O(CH$_2$)$_n$-phenyl, —C(O)O(CH$_2$)$_n$-(3- to 7-membered monocyclic heterocycle), —C(O)(CH$_2$)$_n$-phenyl, —C(O)(CH$_2$)$_n$-(7- to 10-membered bicyclic heterocycle), —C(O)N((CH$_2$)$_n$-phenyl)$_2$, —C(O)N((CH$_2$)$_n$-phenyl)((CH$_2$)$_q$-3- to 7-membered monocyclic heterocycle), —C(O)N((CH$_2$)$_n$-phenyl)((CH$_2$)$_q$ 7- to 10-membered bicyclic heterocycle), —C(O)N((CH$_2$)$_n$-(3 to 7-membered monocyclic heterocycle)$_2$, —C(O)N((CH$_2$)$_n$-7- to 10-membered bicyclic heterocycle)$_2$, or —SO$_2$NH$_2$;

each n is an integer ranging from 0 to 10; and q is an integer ranging from 0 to 10.

The invention also relates to compounds of Formula (VIIb):

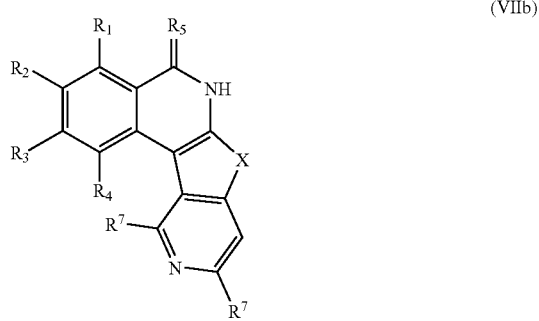

(VIIb)

and pharmaceutically acceptable salts and hydrates thereof, wherein $R_5$ is O, NH or S;

X is —C(O)—, —CH$_2$—, —CH(halo)-, —CH(OH)—, —(C(OH)((CH$_2$)$_m$CH$_3$))—, —(C(OH)(aryl))-, —O—, —N($Z_5$)—, —S—, —CH(NR$_{11}$R$_{12}$)— or —N(SO$_2$Y)—, wherein Y is —OH, —NH$_2$, —($C_1$–$C_5$ alkyl)-(3- to 7-membered monocyclic heterocycle), or —($C_1$–$C_5$ alkyl)-(7- to 10-membered bicyclic heterocycle) and m is an integer ranging from 0–5;

$R_{11}$ and $R_{12}$ are independently -hydrogen or —$C_1$–$C_9$ alkyl, or N, $R_{11}$ and $R_{12}$ are taken together to form a -(nitrogen-containing 3- to 7-membered monocyclic heterocycle), or a -(nitrogen-containing 7- to 10-membered bicyclic heterocycle);

$R_1$, $R_2$, $R_3$, and $R_4$ are independently -hydrogen, -halo, -hydroxy, —O—($C_1$–$C_5$ alkyl), —$C_1$–$C_{10}$ alkyl, halo-substituted-($C_1$–$C_5$ alkyl), —$C_2$–$C_{10}$ alkenyl, —$C_3$–$C_8$-cycloalkyl, -aryl, —NH$_2$, amino-substituted-($C_1$–$C_5$ alkyl), —C(O)OH, —C(O)O($C_1$–$C_5$ alkyl), —OC(O)($C_1$–$C_5$ alkyl), NO$_2$ or -A-B;

A is —SO$_2$—, —SO$_2$NH—, —NHCO—, —NHCONH—, —O—, —CO—, —OC(O)—, —C(O)O—, —CONH—, —CON($C_1$–$C_4$ alkyl)-, —NH—, —CH$_2$—, —S— or —C(S)—;

B is —$C_1$–$C_{10}$ alkyl, —$C_2$–$C_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —$C_3$–$C_8$ cycloalkyl, -aryl, —NZ$_1$Z$_2$, —($C_1$–$C_5$ alkylene)-NZ$_1$Z$_2$, amino-substituted-($C_1$–$C_5$ alkyl), —N($C_1$–$C_5$ alkyl)($C_1$–$C_5$ alkyl), —($C_1$–$C_5$ alkyl)-(3- to 7-membered monocyclic heterocycle), or —($C_1$–$C_5$ alkyl)-(7- to 10-membered bicyclic heterocycle), —(H$_2$NC(O))-substituted aryl, —(H$_2$NC(O))-substituted pyridyl, —C(O)OH, —C(O)O—($C_1$–$C_5$ alkyl), —C(O)O-phenyl or —C(NH)NH$_2$, each of which is unsubstituted or substituted with one or more of —O—($C_1$–$C_5$ alkyl), -halo, halo-substituted-($C_1$–$C_5$ alkyl), HO-substituted-($C_1$–$C_5$ alkyl), amino-substituted-($C_1$–$C_5$ alkyl), -hydroxy, —NO$_2$, —NH$_2$, —CN, —NH($C_1$–$C_5$ alkyl), —N($C_1$–$C_5$ alkyl)($C_1$–$C_5$ alkyl), -(nitrogen-containing 3- to 7-membered monocyclic heterocycle), 7- to 10-membered bicycloheterocyclic amine, —$C_1$–$C_{10}$ alkyl, —$C_2$–$C_{10}$ alkenyl, —$C_2$–$C_{10}$ alkynyl, -aryl, -benzyl, —(H$_2$NC(O))-substituted($C_1$–$C_5$ alkyl), carboxy-substituted-($C_1$–$C_5$ alkyl), —C(O)OH, —$C_1$–$C_5$-alkylene-C(O)O—($C_1$–$C_5$ alkyl) or —$C_1$–$C_5$ alkylene-OC(O)—($C_1$–$C_5$ alkyl); and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —NH$_2$; or N, $Z_3$ and $Z_4$ are taken together to form a (nitrogen-containing 3- to 7-membered monocyclic heterocycle) or a -(nitrogen-containing 7- to 10-membered bicyclic heterocycle); or N, $Z_1$ and $Z_2$ are taken together to form a -(nitrogen-containing 3- to 7-membered monocyclic heterocycle), or a -(nitrogen-containing 7- to 10-membered bicyclic heterocycle);

each $R_7$ is independently —H, —$C_1$–$C_6$ alkyl, —O—($C_1$–$C_6$ alkyl), —S—($C_1$–$C_6$ alkyl), —SO$_2$NH($C_1$–$C_6$ alkyl) or C(O)NH—($C_1$–$C_6$ alkyl);

$Z_5$ is —H, —$C_1$–$C_5$ alkyl, —(CH$_2$)$_n$—CN, —(CH$_2$)$_n$-aryl, —(CH$_2$)$_n$-(3- to 7-membered monocyclic heterocycle), —(CH$_2$)$_n$-(7- to 10-membered bicyclic heterocycle), —(CH$_2$)$_n$—COO—(C$_1$–C$_5$ alkyl), —(CH$_2$)$_n$—COO-aryl, —(CH$_2$)$_n$—COOH, —CONH—(CH$_2$)$_n$—COOH, —CONH—(CH$_2$)$_n$—COO—(C$_1$–C$_5$ alkyl), —CONH—(CH$_2$)$_n$-aryl, —CONHNH—(C$_1$–C$_5$ alkyl), —CONHNH-aryl, —(CH$_2$)$_n$—CONH$_2$, —(CH$_2$)$_n$—CONH—(C$_1$–C$_5$ alkyl), —(CH$_2$)$_n$—CONH-aryl, —(CH$_2$)$_n$—CONH—(CH$_2$)$_q$-aryl, —(CH$_2$)$_n$—CONH—(CH$_2$)$_q$-(3- to 7-membered monocyclic heterocycle), —(CH$_2$)$_n$—CONH—(CH$_2$)$_q$-(3- to 7-membered monocyclic heterocycle), —(CH$_2$)$_n$—CONH—(CH$_2$)$_q$—CONH$_2$—(CH$_2$)$_n$—CONH—(CH$_2$)$_q$—CONH—(C$_1$–C$_5$ alkyl), —(CH$_2$)$_n$—CONH—(CH$_2$)$_q$—CON(C$_1$–C$_5$ alkyl)$_2$, —C(O)(CH$_2$)$_n$—(C$_1$–C$_5$ alkyl), —C(O)(CH$_2$)$_n$-aryl, —C(O)(CH$_2$)$_n$—COOH, —C(O)(CH$_2$)$_n$—COO—(C$_1$–C$_5$alkyl), —C(O)(CH$_2$)$_n$—COO-(3- to 7-membered monocyclic heterocycle), —C(O)(CH$_2$)$_n$—COO-(7- to 10-membered bicyclic heterocycle), —C(O)(CH$_2$)$_n$-phenyl, —C(O)(CH$_2$)$_n$-(3- to 7-membered monocyclic heterocycle), —C(O)(CH$_2$)$_n$-phenyl, —C(O)(CH$_2$)$_n$-(7- to 10-membered bicyclic heterocycle), —C(O)O(CH$_2$)$_n$-phenyl, —C(O)O(CH$_2$)$_n$-(3- to 7-membered monocyclic heterocycle), —C(O)(CH$_2$)$_n$-phenyl, —C(O)(CH$_2$)$_n$-(7- to 10-membered bicyclic heterocycle), —C(O)N((CH$_2$)$_n$-phenyl)$_2$, —C(O)N((CH$_2$)$_n$-phenyl)((CH$_2$)$_q$-3- to 7-membered monocyclic heterocycle), —C(O)N((CH$_2$)$_n$-phenyl)((CH$_2$)$_q$ 7- to 10-membered bicyclic heterocycle), —C(O)N((CH$_2$)$_n$-(3- to 7-membered monocyclic heterocycle)$_2$, —C(O)N((CH$_2$)$_n$- 7- to 10-membered bicyclic heterocycle)$_2$, or —SO$_2$NH$_2$;

each n is an integer ranging from 0 to 10; and q is an integer ranging from 0 to 10.

The invention also relates to compounds of Formula (VIIc):

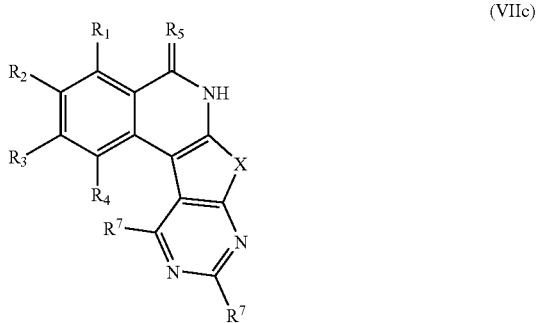

(VIIc)

and pharmaceutically acceptable salts and hydrates thereof, wherein

R$_5$ is O, NH or S;

X is —C(O)—, —CH$_2$—, —CH(halo)-, —CH(OH)—, —(C(OH)((CH$_2$)$_m$CH$_3$))—, —(C(OH)(aryl))-, —O—, —N(Z$_5$)—, —S—, —CH(NR$_{11}$R$_{12}$)— or —N(SO$_2$Y)—, wherein Y is —OH, —NH$_2$, —(C$_1$–C$_5$ alkyl)-(3- to 7-membered monocyclic heterocycle), or —(C$_1$–C$_5$ alkyl)-(7- to 10-membered bicyclic heterocycle) and m is an integer ranging from 0–5;

R$_{11}$ and R$_{12}$ are independently -hydrogen or —C$_1$–C$_9$ alkyl, or N, R$_{11}$ and R$_{12}$ are taken together to form a -(nitrogen-containing 3- to 7-membered monocyclic heterocycle), or a -(nitrogen-containing 7- to 10-membered bicyclic heterocycle);

R$_1$, R$_2$, R$_3$, and R$_4$ are independently -hydrogen, -halo, -hydroxy, —O—(C$_1$–C$_5$ alkyl), —C$_1$–C$_{10}$ alkyl, halo-substituted-(C$_1$–C$_5$ alkyl), —C$_2$–C$_{10}$ alkenyl, —C$_3$–C$_8$-cycloalkyl, -aryl, —NH$_2$, amino-substituted-(C$_1$–C$_5$ alkyl), —C(O)OH, —C(O)O(C$_1$–C$_5$ alkyl), —OC(O)(C$_1$–C$_5$ alkyl), NO$_2$ or -A-B;

A is —SO$_2$—, —SO$_2$NH—, —NHCO—, —NHCONH—, —O—, —CO—, —OC(O)—, —C(O)O—, —CONH—, —CON(C$_1$–C$_4$ alkyl)-, —NH—, —CH$_2$—, —S— or —C(S)—;

B is —C$_1$–C$_{10}$ alkyl, —C$_2$–C$_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —C$_3$–C$_8$ cycloalkyl, -aryl, —NZ$_1$Z$_2$, —(C$_1$–C$_5$ alkylene)-NZ$_1$Z$_2$, amino-substituted-(C$_1$–C$_5$ alkyl), —N(C$_1$–C$_5$ alkyl)(C$_1$–C$_5$ alkyl), —(C$_1$–C$_5$ alkyl)-(3- to 7-membered monocyclic heterocycle), or —C$_1$–C$_5$ alkyl)-(7- to 10-membered bicyclic heterocycle), —(H$_2$NC(O))-substituted aryl, —(H$_2$NC(O))-substituted pyridyl, —C(O)OH, —C(O)O—(C$_1$–C$_5$ alkyl), —C(O)O-phenyl or —C(NH)NH$_2$, each of which is unsubstituted or substituted with one or more of —O—(C$_1$–C$_5$ alkyl), -halo, halo-substituted-(C$_1$–C$_5$ alkyl), HO-substituted-(C$_1$–C$_5$ alkyl), amino-substituted-(C$_1$–C$_5$ alkyl), -hydroxy, —NO$_2$, —NH$_2$, —CN, —NH(C$_1$–C$_5$ alkyl), —N(C$_1$–C$_5$ alkyl)(C$_1$–C$_5$ alkyl), -(nitrogen-containing 3- to 7-membered monocyclic heterocycle), 7- to 10-membered bicycloheterocyclic amine, —C$_1$–C$_{10}$ alkyl, —C$_2$–C$_{10}$ alkenyl, —C$_2$–C$_{10}$ alkynyl, -aryl, -benzyl, —(H$_2$NC(O))-substituted(C$_1$–C$_5$ alkyl), carboxy-substituted-(C$_1$–C$_5$ alkyl), —C(O)OH, —C$_1$–C$_5$-alkylene-C(O)O—(C$_1$–C$_5$ alkyl) or —C$_1$–C$_5$ alkylene-OC(O)—(C$_1$–C$_5$ alkyl); and Z$_1$ and Z$_2$ are independently —H or —C$_1$–C$_{10}$ alkyl, which is unsubstituted or substituted with one or more of -halo, —OH or —N(Z$_3$)(Z$_4$), where Z$_3$ and Z$_4$ are independently, —H or —C$_1$–C$_5$ alkyl, which is unsubstituted or substituted with one or more of -halo, -hydroxy or —NH$_2$; or N, Z$_3$ and Z$_4$ are taken together to form a -(nitrogen-containing 3- to 7-membered monocyclic heterocycle) or a -(nitrogen-containing 7- to 10-membered bicyclic heterocycle); or N, Z$_1$ and Z$_2$ are taken together to form a -(nitrogen-containing 3- to 7-membered monocyclic heterocycle), or a -(nitrogen-containing 7- to 10-membered bicyclic heterocycle);

each R$_7$ is independently —H, —C$_1$–C$_6$ alkyl, —O—(C$_1$–C$_6$ alkyl), —S—(C$_1$–C$_6$ alkyl), —SO$_2$NH(C$_1$–C$_6$ alkyl) or C(O)NH—(C$_1$–C$_6$ alkyl);

Z$_5$ is —H, —C$_1$–C$_5$ alkyl, —(CH$_2$)$_n$—CN, —(CH$_2$)$_n$-aryl, —(CH$_2$)$_n$-(3- to 7-membered monocyclic heterocycle), —(CH$_2$)$_n$-(7- to 10-membered bicyclic heterocycle), —(CH$_2$)$_n$—COO—(C$_1$–C$_5$ alkyl), —(CH$_2$)$_n$—COO-aryl, —(CH$_2$)$_n$—COOH, —CONH—(CH$_2$)$_n$—COOH, —CONH—(CH$_2$)$_n$—COO—(C$_1$–C$_5$ alkyl), —CONH—(CH$_2$)$_n$-aryl, —CONHNH—(C$_1$–C$_5$ alkyl), —CONHNH-aryl, —(CH$_2$)$_n$—CONH$_2$, —(CH$_2$)$_n$—CONH—(C$_1$–C$_5$ alkyl), —(CH$_2$)$_n$—CONH-aryl, —(CH$_2$)$_n$—CONH—(CH$_2$)$_q$-aryl, —(CH$_2$)$_n$—CONH—(CH$_2$)$_q$-(3- to 7-membered monocyclic heterocycle), —(CH$_2$)$_n$—CONH—(CH$_2$)$_q$-(3- to 7-membered monocyclic heterocycle), —(CH$_2$)$_n$—CONH—(CH$_2$)$_q$—CONH$_2$—(CH$_2$)$_n$—CONH—(CH$_2$)$_q$—CONH—(C$_1$–C$_5$ alkyl), —(CH$_2$)$_n$—CONH—(CH$_2$)$_q$—CON(C$_1$–C$_5$ alkyl)$_2$, —C(O)(CH$_2$)$_n$—(C$_1$–C$_5$ alkyl), —C(O)(CH$_2$)$_n$-aryl, —C(O)(CH$_2$)$_n$—COOH, —C(O)(CH$_2$)$_n$—COO—(C$_1$–C$_5$alkyl), —C(O)(CH$_2$)$_n$—COO-(3- to 7-membered monocyclic heterocycle), —C(O)(CH$_2$)$_n$—COO-(7- to 10-membered bicyclic heterocycle), —C(O)(CH$_2$)$_n$-phenyl, —C(O)(CH$_2$)$_n$-(3- to 7-membered monocyclic heterocycle), —C(O)(CH$_2$)$_n$-phenyl, —C(O)(CH$_2$)$_n$-(7- to 10-membered bicyclic heterocycle), —C(O)O(CH$_2$)$_n$-phenyl, —C(O)O(CH$_2$)$_n$-(3- to 7-membered monocyclic heterocycle), —C(O)(CH$_2$)$_n$-phenyl, —C(O)(CH$_2$)$_n$-(7- to 10-membered bicyclic heterocycle), —C(O)N((CH$_2$)$_n$-phenyl)$_2$, —C(O)N((CH$_2$)$_n$-phenyl)((CH$_2$)$_q$-3- to 7-membered monocyclic heterocycle), —C(O)N((CH$_2$)$_n$-phenyl)((CH$_2$)$_q$ 7- to 10-membered bicyclic heterocycle), —C(O)N((CH$_2$)$_n$-(3- to 7-membered monocyclic heterocycle)$_2$, —C(O)N((CH$_2$)$_n$-7- to 10-membered bicyclic heterocycle)$_2$, or —SO$_2$NH$_2$;

each n is an integer ranging from 0 to 10; and
q is an integer ranging from 0 to 10.

A compound of Formula (I), (Ia), (Ib), (II) (IIa), (III), (IV), (V), (VI), (VII), (VIIa), (VIIb) or (VIIc) or a pharmaceutically acceptable salt or hydrate thereof (a "Tetracyclic Benzamide Derivative") is useful for treating or preventing an inflammatory disease, a reperfusion disease, an ischemic condition, renal failure, diabetes, a diabetic complication, a vascular disease, or cancer (each being a "Condition") in an subject.

The invention also relates to compositions comprising an amount of a Tetracyclic Benzamide Derivative that is effective to treat or prevent a Condition, and a pharmaceutically acceptable carrier or vehicle. The compositions are useful for treating or preventing a Condition in a subject.

The invention further relates to methods for treating or preventing a Condition, comprising administering to a subject in need thereof an amount of a Tetracyclic Benzamide Derivative that is effective to treat or prevent the Condition.

The present invention may be understood more fully by reference to the following detailed description and illustrative examples, which are intended to exemplify non-limiting embodiments of the invention.

4. DETAILED DESCRIPTION OF THE INVENTION

4.1 Tetracyclic Benzamide Derivatives of Formula (I)

As stated above, the present invention encompasses compounds of Formula (I)

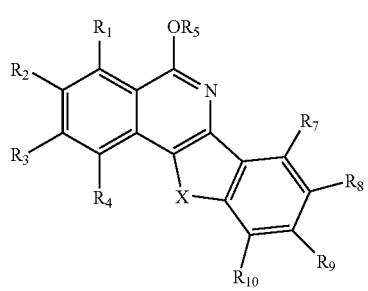

and pharmaceutically acceptable salts and hydrates thereof, where R$_1$, R$_2$, R$_3$, R$_4$, R$_5$, R$_7$, R$_8$, R$_9$, R$_{10}$, and X are defined above for the Tetracyclic Benzamide Derivatives of Formula (I).

In one embodiment X is O.
In one embodiment R$_1$–R$_4$, R$_7$ and R$_{10}$ are hydrogen.
In another embodiment, at least one of R$_1$, R$_2$, R$_3$, R$_4$, R$_7$, R$_8$, R$_9$ and R$_{10}$ is other than hydrogen.
In one embodiment R$_5$ is —C$_2$–C$_{10}$ alkyl.
In another embodiment R$_5$ is —C$_4$–C$_{10}$ alkyl.

In another embodiment R$_5$ is —C$_6$–C$_{10}$ alkyl.
In another embodiment the compounds of Formula (I) have the structure of Formula (I'):

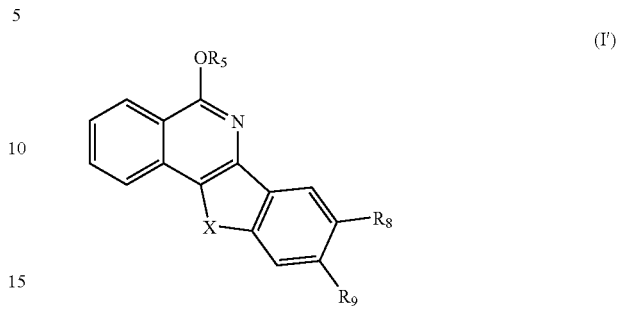

wherein X, R$_5$, R$_8$ and R$_9$ are defined above for the Tetracyclic Benzamide Derivatives of Formula (I).

4.2 Tetracyclic Benzamide Derivatives of Formula (Ia)

As stated above, the invention further encompasses compounds of Formula (Ia):

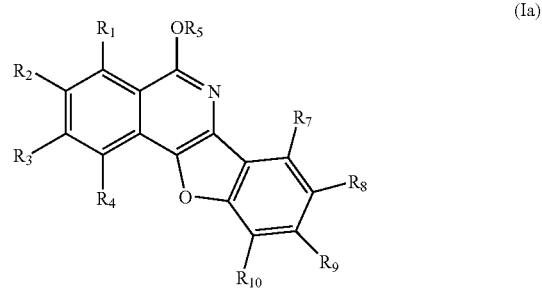

and pharmaceutically acceptable salts and hydrates thereof, where R$_1$, R$_2$, R$_3$, R$_4$, R$_5$, R$_7$, R$_8$, R$_9$, and R$_{10}$, are defined above for the Tetracyclic Benzamide Derivatives of Formula (Ia).

In one embodiment R$_1$–R$_4$, R$_7$ and R$_{10}$ are hydrogen.
In another embodiment, at least one of R$_1$, R$_2$, R$_3$, R$_4$ R$_7$, R$_8$, R$_9$ or R$_{10}$ is other than hydrogen.
In one embodiment R$_5$ is —C$_2$–C$_{10}$ alkyl.
In another embodiment R$_5$ is —C$_4$–C$_{10}$ alkyl.
In another embodiment R$_5$ is —C$_6$–C$_{10}$ alkyl.
In another embodiment compounds of Formula (Ia) have the structure of Formula (Ia'):

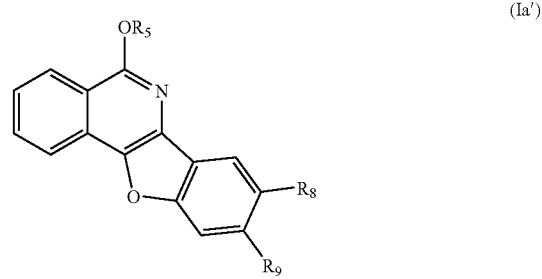

wherein $R_5$, $R_8$, and $R_9$ are defined above for compounds of Formula (Ia).

Illustrative compounds of Formula (Ia') are set forth below:

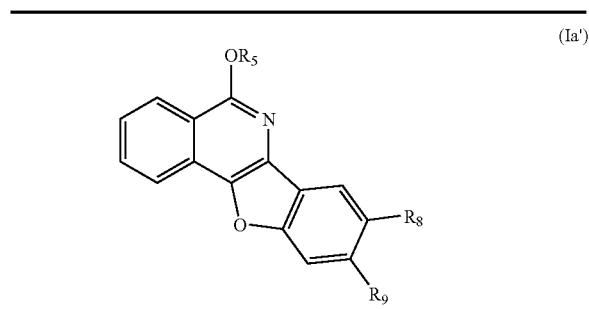

(Ia')

| Compound No. | $R_5$ | $R_8$ | $R_9$ |
|---|---|---|---|
| 16a | —CH$_2$COOH | —OCH$_2$COOH | —H |
| 16b | —(CH$_2$)$_3$OH | —O(CH$_2$)$_3$OH | —H |
| 16c | —(CH$_2$)$_5$OH | —O(CH$_2$)$_5$OH | —H |
| 16d | —(CH$_2$)$_6$OH | —O(CH$_2$)$_6$OH | —H |
| 16e | —(CH$_2$)$_4$COOH | —O(CH$_2$)$_4$COOH | —H |
| 16f | —CH$_3$ | —H | —H |
| 16g | —C(O)CH$_3$ | —H | —H |
| 16h | -glucuronide | —H | —H |
| 16i | —CH$_3$ | —H | —OCH$_3$ |
| 16j | —(CH$_2$)$_3$OH | —H | —O(CH$_2$)$_3$OH |
| 16k | —(CH$_2$)$_6$OH | —H | —O(CH$_2$)$_6$OH | and pharmaceutically acceptable salts and hydrates thereof.

4.3 Tetracyclic Benzamide Derivatives of Formula (Ib)

The invention also relates to compounds of Formula (Ib):

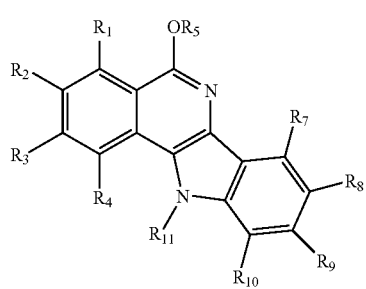

(Ib)

and pharmaceutically acceptable salts and hydrates thereof, where $R_1$, $R_2$, $R_3$, $R_4$, $R_5$, $R_7$, $R_8$, $R_9$, $R_{10}$, and $R_{11}$ are defined above for the Tetracyclic Benzamide Derivatives of Formula (Ib).

In one embodiment, $R_1$–$R_4$, $R_7$ and $R_{10}$ are hydrogen.

In another embodiment, at least one of $R_1$, $R_2$, $R_3$, $R_4$, $R_7$, $R_8$, $R_9$ and $R_{10}$ is other than hydrogen.

In one embodiment $R_5$ is —C$_2$–C$_{10}$ alkyl.

In another embodiment $R_5$ is —C$_4$–C$_{10}$ alkyl.

In another embodiment $R_5$ is —C$_6$–C$_{10}$ alkyl.

In a further embodiment $R_5$ is —C(O)(C$_1$–C$_5$ alkyl).

In yet another embodiment $R_{11}$ is —C(O)(C$_1$–C$_5$ alkyl).

In another embodiment the compounds of Formula (Ib) have the structure of Formula (Ib'):

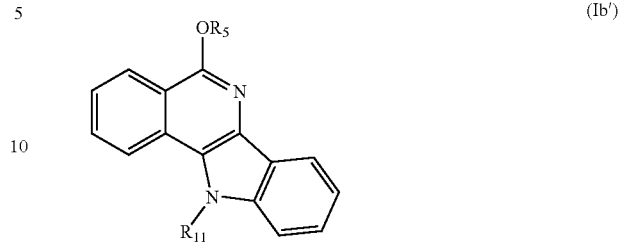

(Ib')

wherein $R_5$ and $R_{11}$ are defined above for Formula (Ib).

An illustrative compound of Formula (Ib') is compound 21a, set forth below:

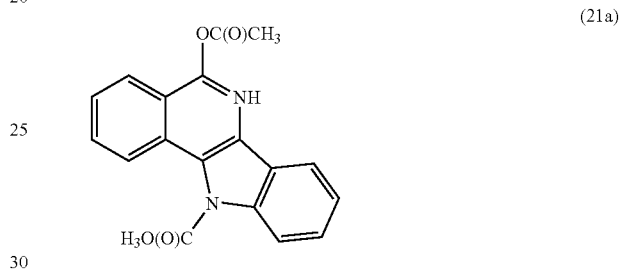

(21a)

and pharmaceutically acceptable salts and hydrates thereof.

4.4 Tetracyclic Benzamide Derivatives of Formula (II)

As stated above, the present invention encompasses compounds of Formula (II):

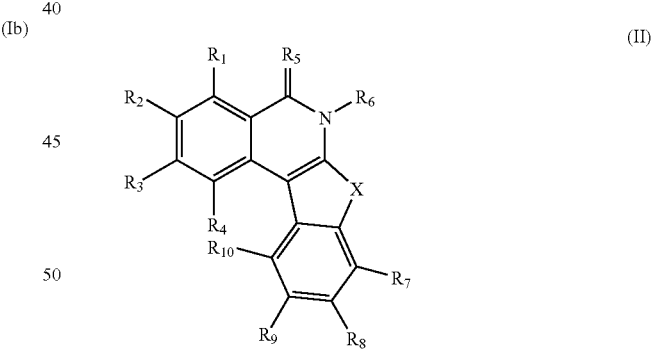

(II)

and pharmaceutically acceptable salts and hydrates thereof, where $R_1$, $R_2$, $R_3$, $R_4$, $R_5$, $R_6$, $R_7$, $R_8$, $R_9$, $R_{10}$, and X are defined above for the Tetracyclic Benzamide Derivatives of Formula (II).

In one embodiment, $R_1$–$R_4$, $R_7$ and $R_{10}$ are hydrogen.

In another embodiment, at least one of $R_1$, $R_2$, $R_3$, $R_4$, $R_7$, $R_8$, $R_9$ and $R_{10}$ is other than hydrogen.

In another embodiment $R_7$–$R_{10}$ are hydrogen.

In still another embodiment, $R_6$ is hydrogen.

In one embodiment $R_1$–$R_4$ and $R_7$–$R_{10}$ is other than —O—(C$_1$–C$_5$ alkyl), and -A-B is other than —O—(C$_1$–C$_{10}$ alkyl).

In another embodiment compounds of Formula (II) have the structure of Formula (II'):

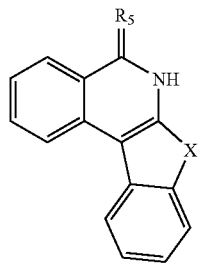

(II')

wherein X and $R_5$ are defined above for Formula (II).

In other illustrative embodiments $R_5$ and X of Formula (II') are as set forth below:

| $R_5$ | X |
|---|---|
| NH | —C(O)— |
| NH | —S— |
| NH | —NH— |
| NH | —CH$_2$— |
| NH | —N(SO$_2$Y)— |
| S | —C(O)— |
| S | —S— |
| S | —NH— |
| S | —CH$_2$— |
| S | —N(SO$_2$Y)— |
| O | —C(O)— |
| O | —S— |
| O | —NH— |
| O | —CH$_2$— |
| O | —N(SO$_2$Y)— | and pharmaceutically acceptable salts and hydrates thereof.

4.5 Tetracyclic Benzamide Derivatives of Formula (IIa)

As stated above, the present invention encompasses compounds of Formula (IIa):

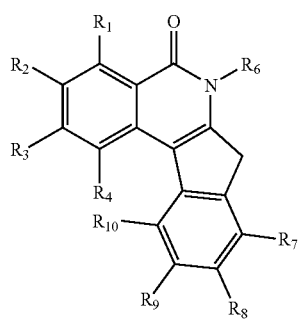

(IIa)

and pharmaceutically acceptable salts and hydrates thereof, where $R_1$, $R_2$, $R_3$, $R_4$, $R_5$, $R_6$, $R_7$, $R_8$, $R_9$, and $R_{10}$ are defined above for the Tetracyclic Benzamide Derivatives of Formula (IIa).

In one embodiment, $R_1$–$R_4$ are hydrogen.

In one embodiment, $R_1$–$R_4$, $R_7$, $R_9$, and $R_{10}$ are hydrogen.

In another embodiment, at least one of $R_1$, $R_2$, $R_3$, $R_4$, $R_7$, $R_8$, $R_9$ and $R_{10}$ is other than hydrogen.

In still another embodiment, $R_6$ is hydrogen.

In one embodiment $R_1$–$R_4$ and $R_7$–$R_{10}$ is other than —O—(C$_1$–C$_5$ alkyl), and -A-B is other than —O—(C$_1$–C$_{10}$ alkyl).

In another embodiment compounds of Formula (IIa) have the structure of Formula (IIa'):

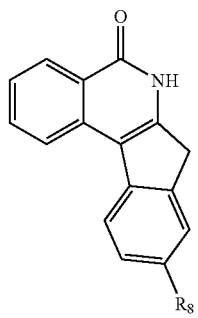

(IIa')

wherein $R_8$ is defined above for Formula (IIa).

In one embodiment $R_8$ is -A-B, where -A- is —SO$_2$— and —B is —NZ$_1$Z$_2$ or —(C$_1$–C$_5$alkylene)-NZ$_1$Z$_2$.

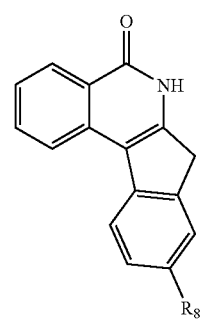

(IIa')

| Compound No. | $R_8$ |
|---|---|
| 9a | —H |
| 11a | —SO$_2$NH(CH$_2$)$_3$-(N-morpholinyl) |

4.6 Tetracyclic Benzamide Derivatives of Formula (III)

As stated above, the present invention encompasses compounds of Formula (III):

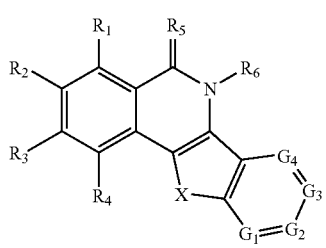

(III)

and pharmaceutically acceptable salts and hydrates thereof, where $R_1$, $R_2$, $R_3$, $R_4$, $R_5$, $R_6$, $G_1$, $G_2$, $G_3$, $G_4$, and X are defined above for the Tetracyclic Benzamide Derivatives of Formula (III).

In one embodiment $R_1$–$R_4$ are hydrogen.

In another embodiment, at least one of $R_1$, $R_2$, $R_3$, $R_4$ and $R_7$ is other than hydrogen.

In yet another embodiment $R_5$ is oxygen.

In still another embodiment, one of $G_1$–$G_4$ is N.

In another embodiment $G_1$ is N; and $G_2$–$G_4$ are C—$R_7$.

In another embodiment $G_2$ is N; and $G_1$, $G_3$ and $G_4$ are C—$R_7$.

In another embodiment $G_3$ is N; and $G_1$, $G_2$ and $G_4$ are C—$R_7$.

In another embodiment $G_4$ is N; and $G_1$, $G_2$, and $G_3$ are C—$R_7$.

In another embodiment $G_1$ and $G_2$ are N and $G_3$ and $G_4$ are C—$R_7$.

In another embodiment $G_1$ and $G_3$ are N and $G_2$ and $G_4$ are C—$R_7$.

In another embodiment $G_1$ and $G_4$ are N and $G_2$ and $G_3$ are C—$R_7$.

In another embodiment $G_2$ and $G_3$ are N and $G_1$ and $G_4$ are C—$R_7$.

In another embodiment $G_2$ and $G_4$ are N and $G_1$ and $G_3$ are C—$R_7$.

In another embodiment $G_3$ and $G_4$ are N and $G_1$ and $G_2$ are C—$R_7$.

In another embodiment compounds of Formula (III) have the structure of Formula (III'):

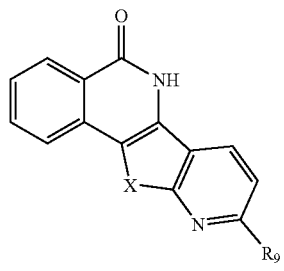

(III')

wherein X, and $R_9$ are defined above for Formula (III).

An illustrative example of a compound of Formula (III') is set forth below:

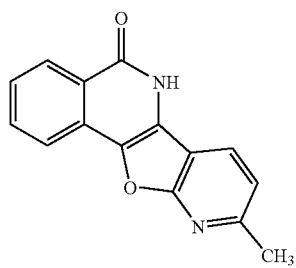

(26a)

and pharmaceutically acceptable salts and hydrates thereof 4.7 Tetracyclic Benzamide Derivatives of Formula (IV)

As stated above, the present invention encompasses compounds of Formula (IV):

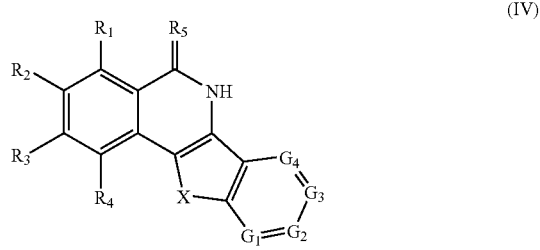

(IV)

and pharmaceutically acceptable salts and hydrates thereof, where $R_1$, $R_2$, $R_3$, $R_4$, $R_5$, $G_1$, $G_2$, $G_3$, $G_4$, and X are defined above for the Tetracyclic Benzamide Derivatives of Formula (IV).

In one embodiment $R_1$–$R_4$ are hydrogen.

In another embodiment, at least one of $R_1$, $R_2$, $R_3$, $R_4$ or $R_7$ is other than hydrogen.

In yet another embodiment $R_5$ is oxygen.

In still another embodiment, $R_6$ is hydrogen.

In still another embodiment, one of $G_1$–$G_4$ is N.

In another embodiment $G_1$ is N; and $G_2$–$G_4$ are C—$R_7$.

In another embodiment $G_2$ is N, $G_1$, $G_3$, $G_4$ are C—$R_7$.

In another embodiment $G_3$ is N, $G_1$, $G_2$, $G_4$ are C—$R_7$.

In another embodiment $G_4$ is N, $G_1$, $G_2$, and $G_3$ are C—$R_7$.

In another embodiment $G_1$ and $G_2$ are N and $G_3$ and $G_4$ are C—$R_7$.

In another embodiment $G_1$ and $G_3$ are N and $G_2$ and $G_4$ are C—$R_7$.

In another embodiment $G_1$ and $G_4$ are N and $G_2$ and $G_3$ are C—$R_7$.

In another embodiment $G_2$ and $G_3$ are N and $G_1$ and $G_4$ are C—$R_7$.

In another embodiment $G_2$ and $G_4$ are N and $G_1$ and $G_3$ are C—$R_7$.

In another embodiment $G_3$ and $G_4$ are N and $G_1$ and $G_2$ are C—$R_7$.

In another embodiment compounds of Formula (IV) have the structure of Formula (IV'):

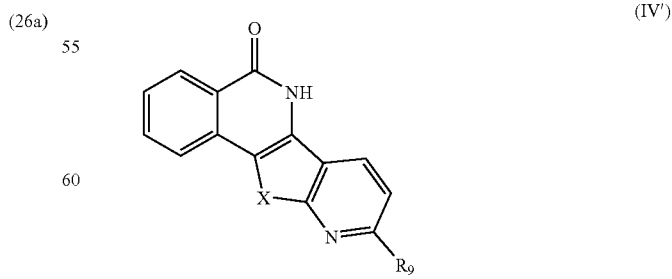

(IV')

wherein X, $R_9$ and $R_{10}$ are defined above for Formula (IV).

4.8 Tetracyclic Benzamide Derivatives of Formula (V)

As stated above, the present invention encompasses compounds of Formula (V):

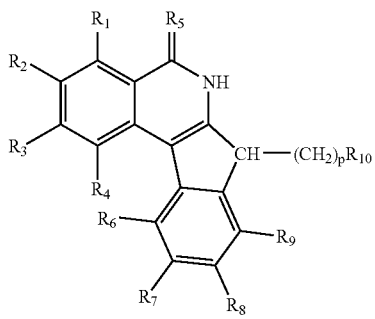

(V)

and pharmaceutically acceptable salts and hydrates thereof, where $R_1$, $R_2$, $R_3$, $R_4$, $R_5$, $R_6$, $R_7$, $R_8$, $R_9$, $R_{10}$ and p are defined above for the Tetracyclic Benzamide Derivatives of Formula (V).

In one embodiment, $R_1$–$R_4$ are hydrogen. In another embodiment, at least one of $R_1$, $R_2$, $R_3$, $R_4$, $R_6$, $R_7$, $R_8$, and $R_9$ is other than hydrogen. In still another embodiment $R_1$–$R_4$ and $R_6$–$R_9$ is other than —O—($C_1$–$C_5$ alkyl), and -A-B is other than —O—($C_1$–$C_{10}$ alkyl). In one embodiment $R_5$ is O. In another embodiment $R_5$ is NH. In a further embodiment $R_5$ is S.

In another embodiment compounds of Formula (V) have the structure of Formula (V'):

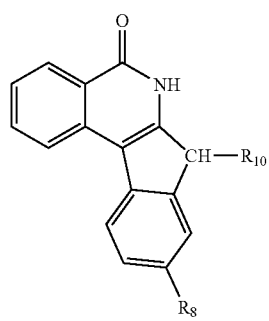

(V')

wherein $R_8$ and $R_{10}$ are defined above for Formula (V).

Illustrative compounds of Formula (V') are set forth below:

(V')

| Compound | $R_8$ | $R_{10}$ |
|---|---|---|
| V'1 | —H | —CH$_3$ |
| V'2 | —H | —CH$_2$CH$_3$ |
| V'3 | —H | —CH$_2$Ph |
| V'4 | —H | —COOCH$_3$ |
| V'5 | —H | —COCH$_2$COOMe |
| V'6 | —H | —COCH$_2$COOH |
| V'7 | —H | —COCH$_3$ |
| V'8 | —H | —CONH(CH$_2$)$_2$N(CH$_3$)$_2$ |
| V'9 | —H | —CONH(CH$_2$)$_2$-(N-morpholinyl) |
| V'10 | —H | —CONH(CH$_2$)$_3$-(N-morpholinyl) |
| V'11 | —H | —CONH(CH$_2$)$_2$COOCH$_2$CH$_3$ |
| V'12 | —H | —CONH(CH$_2$)$_2$COOH |
| V'13 | —H | —CONH(CH$_2$)$_2$CONHCH$_3$ |
| V'14 | —H | —CONH-piperidine-1-yl |
| V'15 | —H | —CONH-(N-morpholinyl) |
| V'16 | —H | —CO(CH$_2$)$_2$-tetrazole-5-yl |
| V'17 | —NHCOCH$_2$N(CH$_3$)$_2$ | —COOCH$_2$CH$_3$ |
| V'18 | —SO$_2$NH(CH$_2$)$_3$-(N-morpholinyl) | —COOCH$_2$CH$_3$ |
| V'19 | —NHCOCH$_2$N(CH$_3$)$_2$ | —COOH |
| V'20 | —SO$_2$NH(CH$_2$)$_3$-(N-morpholinyl) | —COOH |
| V'21 | —NHCOCH$_2$N(CH$_3$)$_2$ | —CONHCH$_3$ |
| V'22 | —SO$_2$NH(CH$_2$)$_3$-(N-morpholinyl) | —CONHCH$_3$ |
| V'23 | —NHCOCH$_2$N(CH$_3$)$_2$ | —CONH(CH$_2$)$_2$-(N-morpholinyl) |
| V'24 | —SO$_2$NH(CH$_2$)$_3$-(N-morpholinyl) | —CONH(CH$_2$)$_2$N(CH$_3$)$_2$ |
| V'25 | —NHCOCH$_2$N(CH$_3$)$_2$ | —CONH(CH$_2$)$_2$-(N-morpholinyl) |
| V'26 | —SO$_2$NH(CH$_2$)$_3$-(N-morpholinyl) | —CONH(CH$_2$)$_2$N(CH$_3$)$_2$ | and pharmaceutically acceptable salts and hydrates thereof.

4.9 Tetracyclic Benzamide Derivatives of Formula (VI)

As stated above, the present invention encompasses compounds of Formula (VI):

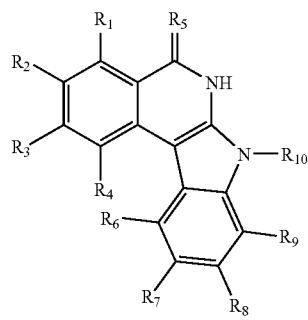

and pharmaceutically acceptable salts and hydrates thereof, where $R_1$, $R_2$, $R_3$, $R_4$, $R_5$, $R_6$, $R_7$, $R_8$, $R_9$, and $R_{10}$ are defined above for the Tetracyclic Benzamide Derivatives of Formula (VI).

In one embodiment, $R_1$–$R_4$ are hydrogen. In another embodiment $R_6$, $R_7$, and $R_9$ are hydrogen. In another embodiment $R_6$–$R_9$ are hydrogen.

In another embodiment, at least one of $R_1$, $R_2$, $R_3$, $R_4$, $R_6$, $R_7$, $R_8$, and $R_9$ is other than hydrogen.

In one embodiment $R_1$–$R_4$ and $R_6$—$R_9$ is other than —O—($C_1$–$C_5$ alkyl), and -A-B is other than —O—($C_1$–$C_{10}$ alkyl).

In another embodiment compounds of Formula (VI) have the structure of Formula (VI'):

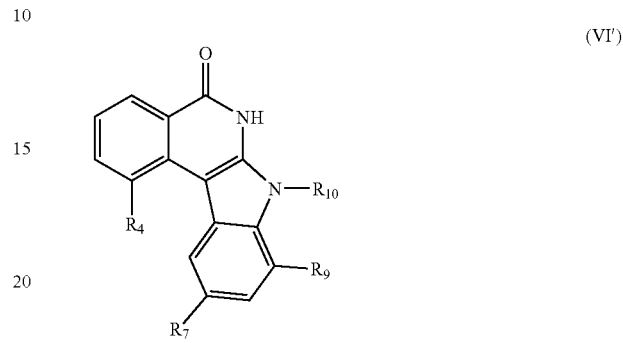

wherein $R_4$, $R_7$, $R_9$, and $R_{10}$ are defined above for Formula (VI).

Illustrative compounds of Formula (VI') are set forth below:

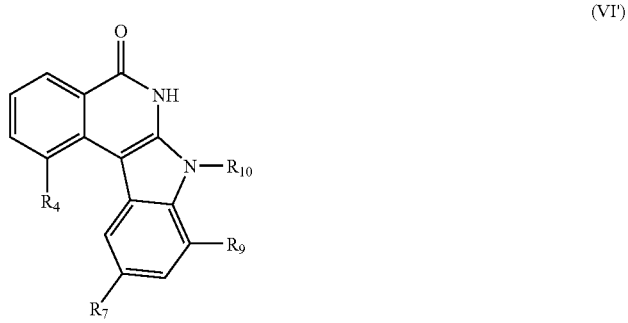

| Compound | $R_4$ | $R_7$ | $R_9$ | $R_{10}$ |
|---|---|---|---|---|
| VI'-1 | —H | —H | —H | —H |
| VI'-2 | —H | —H | —H | —CH$_3$ |
| VI'-3 | —H | —H | —H | —CH$_2$CH$_3$ |
| VI'-4 | —H | —H | —H | —CH$_2$COO CH$_2$CH$_3$ |
| VI'-5 | —H | —H | —H | —CH$_2$COOH |
| VI'-6 | —H | —H | —H | —CH$_2$CONHCH$_3$ |
| VI'-7 | —H | —H | —H | —CH$_2$Ph |
| VI'-8 | —H | —H | —H | —COOCH$_3$ |
| VI'-9 | —H | —H | —H | —SO$_2$NH$_2$ |
| VI'-10 | —H | —H | —H | —COOtBu |
| VI'-11 | —H | —H | —H | —COO CH$_2$CH$_3$ |
| VI'-12 | —H | —H | —H | —COCH$_3$ |
| VI'-13 | —H | —H | —H | —CONHCH$_3$ |
| VI'-14 | —H | —H | —H | —CONH CH$_2$CH$_3$ |
| VI'-15 | —H | —H | —H | —CONH(CH$_2$)$_2$N(CH$_3$)$_2$ |
| VI'-16 | —H | —H | —H | —CONH(CH$_2$)$_2$-(N-morpholinyl) |
| VI'-17 | —H | —H | —H | —CONH(CH$_2$)$_3$-(N-morpholinyl) |
| VI'-18 | —H | —H | —H | —CONH(CH$_2$)$_2$COO CH$_2$CH$_3$ |
| VI'-19 | —H | —H | —H | —CONH(CH$_2$)$_2$COOH |
| VI'-20 | —H | —H | —H | —CONH(CH$_2$)$_2$CONHCH$_3$ |
| VI'-21 | —H | —H | —H | —CONH-piperidine-1-yl |
| VI'-22 | —H | —H | —H | —CONH—(N-morpholinyl) |
| VI'-23 | —H | —H | —H | —CO(CH$_2$)$_2$-tetrazole-5-yl |

-continued

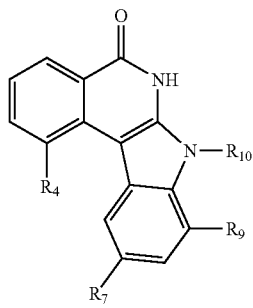
(VI')

| Compound | R₄ | R₇ | R₉ | R₁₀ |
|---|---|---|---|---|
| VI'-24 | —H | —H | —NHCOCH₂N(CH₃)2 | —H |
| VI'-25 | —H | —H | —SO₂NH(CH₂)₃-(N-morpholinyl) | —H |
| VI'-26 | —H | —NHCOCH₂N(CH₃)₂ | —H | —COOCH₃ |
| VI'-27 | —H | —SO₂NH(CH₂)₃-(N-morpholinyl) | —H | —COOCH₃ |
| VI'-28 | —H | —H | —NHCOCH₂NMe₂ | —CONHCH₃ |
| VI'-29 | —H | —H | —SO₂NH(CH₂)₃-(N-morpholinyl) | —CONHCH₃ |
| VI'-30 | —NH₂ | —H | —NHCOCH₂N(CH₃)₂ | —CONHCH₃ |
| VI'-31 | —OH | —SO₂NH(CH₂)₃-(N-morpholinyl) | —H | —CONHCH₃ |
| VI'-32 | —F | —NHCOCH₂N(CH₃)₂ | —H | —CONHCH₃ |
| VI'-33 | —OMe | —H | —SO₂NH(CH₂)₃-(N-morpholinyl) | —CONHCH₃ | and pharmaceutically acceptable salts and hydrates thereof.

4.10 Tetracyclic Benzamide Derivatives of Formula (VII)

As stated above, the present invention encompasses compounds of Formula (VII):

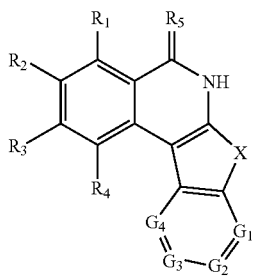
(VII)

and pharmaceutically acceptable salts and hydrates thereof, where $R_1$, $R_2$, $R_3$, $R_4$, $R_5$, $G_1$, $G_2$, $G_3$, $G_4$, and X are defined above for the Tetracyclic Benzamide Derivatives of Formula (VII).

In one embodiment, $R_1$–$R_4$ are hydrogen.

In another embodiment $R_5$ is O.

In another embodiment, at least one of $R_1$, $R_2$, $R_3$, and $R_4$ is other than hydrogen.

In one embodiment $R_1$–$R_4$ is other than —O—($C_1$–$C_5$ alkyl), and -A-B is other than —O—($C_1$–$C_{10}$ alkyl).

In another embodiment X is NH. In still another embodiment X is O.

In a further embodiment X is S. In another embodiment $R_4$ is $NH_2$, $OCH_3$, or $NO_2$.

In still another embodiment, one of $G_1$–$G_4$ is N.

In another embodiment $G_1$ is N; and $G_2$–$G_4$ are C—$R_7$.

In another embodiment $G_2$ is N; and $G_1$, $G_3$ and $G_4$ are C—$R_7$.

In another embodiment $G_3$ is N; and $G_1$, $G_2$ and $G_4$ are C—$R_7$.

In another embodiment $G_4$ is N; and $G_1$, $G_2$, and $G_3$ are C—$R_7$.

In another embodiment $G_1$ and $G_2$ are N and $G_3$ and $G_4$ are C—$R_7$.

In another embodiment $G_1$ and $G_3$ are N and $G_2$ and $G_4$ are C—$R_7$.

In another embodiment $G_1$ and $G_4$ are N and $G_2$ and $G_3$ are C—$R_7$.

In another embodiment $G_2$ and $G_3$ are N and $G_1$ and $G_4$ are C—$R_7$.

In another embodiment $G_2$ and $G_4$ are N and $G_1$ and $G_3$ are C—$R_7$.

In another embodiment $G_3$ and $G_4$ are N and $G_1$ and $G_2$ are C—$R_7$.

In another embodiment compounds of Formula (VII) have the structure of Formula (VII')

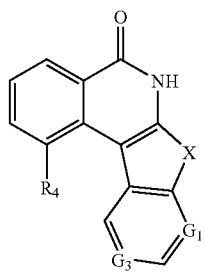
(VII')

wherein X, $G_1$, $G_3$, and $R_4$ are defined above for Formula (VII).

Illustrative compounds of Formula (VII') are set forth below:

(VII')

| Compound | $R_4$ | $G_1$ | $G_3$ | X |
|---|---|---|---|---|
| VII'-1 | —H | —CH | —N | —NH— |
| VII'-2 | —H | —N | —CH | —NH— |
| VII'-3 | —H | —CH | —N | —N(CH$_3$)— |
| VII'-4 | —H | —N | —CH | —N(CH$_3$)— |
| VII'-5 | —H | —CH | —N | —C(H)(CH$_2$COOH)— |
| VII'-6 | —H | —N | —CH | —C(H)(CH$_2$CONHCH$_3$)— |
| VII'-7 | —H | —CH | —N | —O— |
| VII'-8 | —H | —N | —CH | —O— |
| VII'-9 | —H | —CH | —N | —S— |
| VII'-10 | —H | —N | —CH | —S— |
| VII'-11 | —H | —CH | —N | —N(CONHCH$_3$)— |
| VII'-12 | —H | —N | —CH | —N(CONHCH$_2$CH$_3$)— |
| VII'-13 | —H | —CH | —N | —N(CONH(CH$_2$)$_2$N(CH$_3$)$_2$)— |
| VII'-14 | —H | —N | —CH | —N(CONH(CH$_2$)$_2$-(N-morpholinyl))- |
| VII'-15 | —H | —CH | —N | —C(H)(CONH(CH$_2$)$_2$COOCH$_2$CH$_3$)— |
| VII'-16 | —H | —N | —CH | —C(H)CONH(CH$_2$)$_2$COOH)— |
| VII'-17 | —H | —CH | —N | —C(H)(CONH(CH$_2$)$_2$CONHCH$_3$)— |
| VII'-18 | —H | —N | —CH | —C(H)CONH-piperidine-1-yl)- |
| VII'-19 | —H | —CH | —N | —C(H)(CONH-(N-morpholinyl))- |
| VII'-20 | —H | —N | —CH | —C(H)(CO(CH$_2$)$_2$-tetrazole-5-yl)- |
| VII'-21 | —NH$_2$ | —CH | —N | —NH— |
| VII'-22 | —OCH$_3$ | —N | —CH | —NH— | pharmaceutically acceptable salts and hydrates thereof.

4.11 Tetracyclic Benzamide Derivatives of Formula (VIIa)

As stated above, the present invention encompasses compounds of Formula (VIIa):

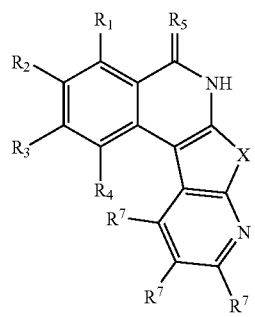

(VIIa)

and pharmaceutically acceptable salts and hydrates thereof, where $R_1$, $R_2$, $R_3$, $R_4$, $R_5$, $R_7$, and X are defined above for the Tetracyclic Benzamide Derivatives of Formula (VIIa).

In one embodiment, $R_1$–$R_4$ are hydrogen. In another embodiment, at least one of $R_1$, $R_2$, $R_3$, $R_4$, $R_6$, and $R_7$, is other than hydrogen. In one embodiment $R_1$–$R_4$ and $R_7$ is other than —O—(C$_1$–C$_5$ alkyl), and -A-B is other than —O—(C$_1$–C$_{10}$ alkyl). In another embodiment X is NH. In still another embodiment X is O. In a further embodiment X is S. In another embodiment $R_4$ is —NH$_2$, —OCH$_3$, or —NO$_2$.

In another embodiment compounds of Formula (VIIa) have the structure of Formula (VIIa'):

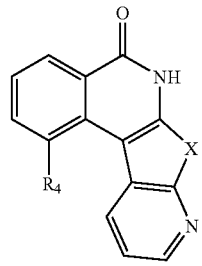

(VIIa')

wherein $R_4$, and X are defined above for Formula (VIIa). Illustrative compounds of Formula (VIIa') are set forth below:

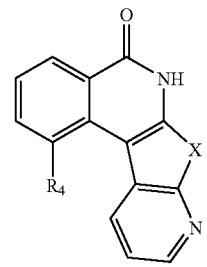

(VIIa')

| Compound | $R_4$ | X |
|---|---|---|
| VIIa'-1 | —H | —NH— |
| VIIa'-2 | —H | —NCH$_3$— |
| VIIa'-3 | —H | —C(H)(CH$_2$COOH)— |
| VIIa'-4 | —H | —O— |
| VIIa'-5 | —H | —S— |

-continued

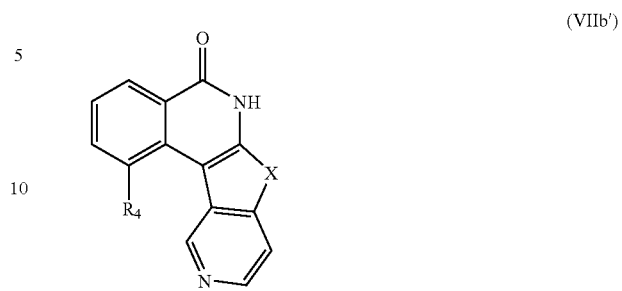

(VIIa')

| Compound | $R_4$ | X |
| --- | --- | --- |
| VIIa'-6 | —H | —N(CONHCH$_3$)— |
| VIIa'-7 | —H | —N(CONH(CH$_2$)$_2$N(CH$_3$)$_2$)— |
| VIIa'-8 | —H | —C(H)(CONH(CH$_2$)$_2$COOCH$_2$CH$_3$)— |
| VIIa'-9 | —H | —C(H)(CONH(CH$_2$)$_2$CONHCH$_3$)— |
| VIIa'-10 | —H | —C(H)(CONH-(N-morpholinyl))- |
| VIIa'-11 | —NH$_2$ | —NH— | and pharmaceutically acceptable salts and hydrates thereof.

4.12 Tetracyclic Benzamide Derivatives of Formula (VIIb)

As stated above, the present invention encompasses compounds of Formula (VIIb):

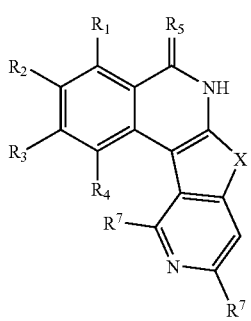

(VIIb)

and pharmaceutically acceptable salts and hydrates thereof, where $R_1$, $R_2$, $R_3$, $R_4$, $R_5$, $R_7$, and X are defined above for the Tetracyclic Benzamide Derivatives of Formula (VIIb).

In one embodiment, $R_1$–$R_4$ are hydrogen.

In another embodiment, at least one of $R_1$, $R_2$, $R_3$, $R_4$, $R_6$, or $R_7$, is other than hydrogen.

In one embodiment $R_1$–$R_4$ and $R_7$ is other than —O—($C_1$–$C_5$ alkyl), and -A-B is other than —O—($C_1$–$C_{10}$ alkyl).

In another embodiment X is NH. In still another embodiment X is O.

In a further embodiment X is S. In another embodiment $R_4$ is NH$_2$, OCH$_3$, or NO$_2$.

In another embodiment compounds of Formula (VIIb) have the structure of Formula (VIIb'):

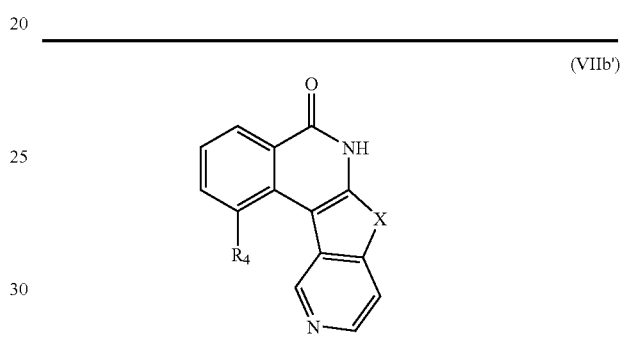

(VIIb')

wherein X and $R_4$ are defined above for Formula (VIIb). Illustrative compounds of Formula (VIIb') are set forth below:

(VIIb')

| Compound | $R_4$ | X |
| --- | --- | --- |
| VIIb'-1 | —H | —NH— |
| VIIb'-2 | —H | —NCH$_3$— |
| VIIb'-3 | —H | —C(H)(CH$_2$CONHCH$_3$)— |
| VIIb'-4 | —H | —O— |
| VIIb'-5 | —H | —S— |
| VIIb'-6 | —H | —N(CONHCH$_2$CH$_3$)— |
| VIIb'-7 | —H | —N(CONH(CH$_2$)$_2$-(N-morpholinyl))- |
| VIIb'-8 | —H | —C(H)(CONH(CH$_2$)$_2$COOH)— |
| VIIb'-9 | —H | —C(H)(CONH-piperidine-1-yl)- |
| VIIb'-10 | —H | —C(H)(CO(CH$_2$)$_2$-tetrazole-5-yl)- |
| VIIb'-11 | —OCH$_3$ | —NH— | pharmaceutically acceptable salts and hydrates thereof.

4.13 Tetracyclic Benzamide Derivatives of Formula (VIIc)

As stated above, the present invention encompasses compounds of Formula (VIIc):

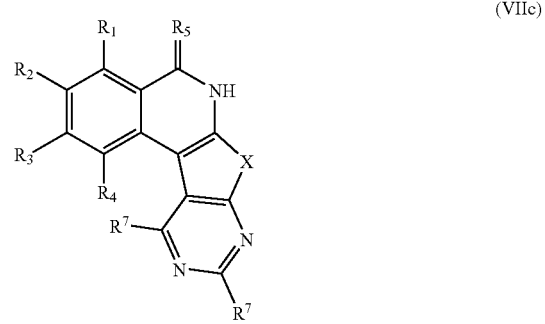

(VIIc)

and pharmaceutically acceptable salts and hydrates thereof, where $R_1$, $R_2$, $R_3$, $R_4$, $R_5$, $R_7$ and X are defined above for the Tetracyclic Benzamide Derivatives of Formula (VIIc).

In one embodiment, $R_1$–$R_4$ are hydrogen. In another embodiment, at least one of $R_1$, $R_2$, $R_3$, $R_4$, $R_6$, or $R_7$ is other than hydrogen. In one embodiment $R_1$–$R_4$ and $R_7$ is other than —O—($C_1$–$C_5$ alkyl), and -A-B is other than —O—($C_1$–$C_{10}$ alkyl). In another embodiment X is NH.

In still another embodiment X is O. In a further embodiment X is S. In another embodiment $R_4$ is —$NH_2$, —$OCH_3$, or —$NO_2$.

In another embodiment compounds of Formula (VIIc) have the structure of Formula (VIIc'):

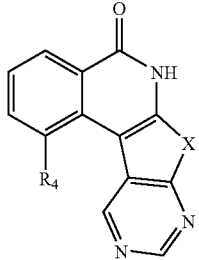

(VIIc')

wherein X and $R_4$ are defined above for Formula (VIIc).

Illustrative compounds of Formula (VIIc) are set forth below:

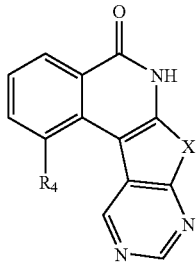

(VIIc')

| Compound | $R_4$ | X |
|---|---|---|
| VIIc'-1 | —H | —NH— |
| VIIc'-2 | —H | —NH— |
| VIIc'-3 | —H | —$NCH_3$— |
| VIIc'-4 | —H | —$NCH_3$— |
| VIIc'-5 | —H | —C(H)($CH_2$COOH) |
| VIIc'-6 | —H | —C(H)($CH_2$CONH$CH_3$)— |
| VIIc'-7 | —H | —O— |
| VIIc'-8 | —H | —O— |
| VIIc'-9 | —H | —S— |
| VIIc'-10 | —H | —S— |
| VIIc'-11 | —H | —N(CONH$CH_3$)— |
| VIIc'-12 | —H | —N(CONH$CH_2CH_3$)— |
| VIIc'-13 | —H | —N(CONH($CH_2$)$_2$N($CH_3$)$_2$)— |
| VIIc'-14 | —H | —N(CONH($CH_2$)$_2$-(N-morpholinyl))— |
| VIIc'-15 | —H | —C(H)(CONH($CH_2$)$_2$COOCH$_2CH_3$)- |
| VIIc'-16 | —H | —C(H)(CONH($CH_2$)$_2$COOH)— |
| VIIc'-17 | —H | —C(H)(CONH($CH_2$)$_2$CONH$CH_3$)— |
| VIIc'-18 | —H | —C(H)(CONH-piperidine-1-yl)- |
| VIIc'-19 | —H | —C(H)(CONH-(N-morpholinyl))- |
| VIIc'-20 | —H | —C(H)(CO($CH_2$)$_2$-tetrazole-5-yl)- |
| VIIc'-22 | —$NH_2$ | —NH— |
| VIIc'-22 | —$OCH_3$ | —NH— | pharmaceutically acceptable salts and hydrates thereof.

4.14 Tetracyclic Benzamide Derivatives Of Formulas (I), (Ia), (Ib), (II), (IIa), (III), (IV), (V), (VI), (VII), (VIIa), (VIIb), and (VIIc)

The Tetracyclic Benzamide Derivatives can exist in a keto or enol tautomeric form. This invention encompasses both the keto and enol forms of the Tetracyclic Benzamide Derivatives. Accordingly, Formulas (I), (Ia) (Ib), (II), (IIa), (III), (IV), (V), (VI), (VII), (VIIa), (VIIb), and (VIIc), although depicting the keto form of the Tetracyclic Benzamide Derivatives, encompass both the keto and enol forms.

The present invention also includes Tetracyclic Benzamide Derivatives, wherein one or more hydrogen, carbon or other atoms are replaced by an isotope thereof. Such compounds are useful as research or diagnostic tools in metabolism pharmacokinetic studies and in binding assays.

4.15 Definitions

The term "—($C_1$–$C_{10}$)alkyl" as used herein, refers to a straight chain or branched non-cyclic hydrocarbon having from 1 to 10 carbon atoms. Representative straight chain —($C_1$–$C_{10}$)alkyls include -methyl, -ethyl, -n-propyl, -n-butyl, -n-pentyl, -n-hexyl, -n-heptyl, -n-octyl, -n-nonly and -n-decyl. Representative branched —($C_1$–$C_{10}$)alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl and 3,3-dimethylbuty, -isopropyl, -sec-butyl, -isobutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

The term "—($C_1$–$C_9$)alkyl" as used herein, refers to a straight chain or branched non-cyclic hydrocarbon having from 1 to 9 carbon atoms. Representative straight chain —($C_1$–$C_9$)alkyls include -methyl, -ethyl, -n-propyl, -n-butyl, -n-pentyl, -n-hexyl, -n-heptyl, -n-octyl, and -n-nonly. Representative branched —($C_1$–$C_9$)alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl and 3,3-dimethylbuty, -isopropyl, -sec-butyl, -isobutyl, 1-methylhexyl, 2-methylhexyl, 3-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

The term "—($C_1$–$C_5$)alkyl" as used herein, refers to a straight chain or branched non-cyclic hydrocarbon having from 1 to 5 carbon atoms. Representative straight chain —($C_1$–$C_5$)alkyls include -methyl, -ethyl, -n-propyl, -n-butyl and -n-pentyl. Representative branched —($C_1$–$C_5$)alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl and 1,2-dimethylpropyl.

The term "—($C_2$–$C_{10}$)alkenyl" as used herein, refers to a straight chain or branched non-cyclic hydrocarbon having from 2 to 10 carbon atoms and including at least one carbon-carbon double bond. Representative straight chain and branched ($C_2$–$C_{10}$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

The term "—($C_3$–$C_8$)cycloalkyl" as used herein, refers to a saturated cyclic hydrocarbon having from 3 to 8 carbon atoms. Representative ($C_3$–$C_8$)cycloalkyls include -cyclopropyl, -cyclobutyl, -cyclopentyl, -cyclohexyl, -cycloheptyl and -cyclooctyl.

The term "—($C_8$–$C_{14}$)bicycloalkyl" as used herein, refers to a bi-cyclic hydrocarbon ring system having from 8 to 14 carbon atoms and at least one saturated cyclic alkyl ring. Representative —($C_8$–$C_4$)bicycloalkyls include -indanyl, -1,2,3,4-tetrahydronaphthyl, -5,6,7,8-tetrahydronaphthyl, -perhydronaphthyl and the like.

A "3- to 7-membered monocyclic heterocycle" refers to a monocyclic 3- to 7-membered aromatic or non-aromatic monocyclic cycloalkyl in which 1–4 of the ring carbon atoms have been independently replaced with a N, O or S atom. The 3- to 7-membered monocyclic heterocycles can be attached via a nitrogen, sulfur, or carbon atom. Representative examples of a 3- to 7-membered monocyclic heterocycle group include, but are not limited to, piperidinyl, piperazinyl, morpholinyl, pyrrolyl, oxazinyl, thiazinyl, diazinyl, triazinyl, tetrazinyl, imidazolyl, tetrazolyl, pyrrolidinyl, isoxazolyl, furanyl, furazanyl, pyridinyl, oxazolyl, thiazolyl, thiophenyl, pyrazolyl, triazolyl, and pyrimidinyl.

A "7- to 10-membered bicyclic heterocycle" refers to a bicyclic 7- to 10-membered aromatic or non-aromatic bicyclic cycloalkyl in which 1–4 of the ring carbon atoms have been independently replaced with a N, O or S atom. The 7- to 10-membered bicyclic heterocycles can be attached via a nitrogen, sulfur, or carbon atom. Representative examples of a 7- to 10-membered bicyclic heterocycle group include, but are not limited to, benzimidazolyl, indolyl, isoquinolinyl, indazolyl, quinolinyl, quinazolinyl, purinyl, benzisoxazolyl, benzoxazolyl, benzthiazolyl, benzodiazolyl, benzotriazolyl, isoindolyl and indazolyl.

A "nitrogen-containing 3- to 7-membered monocyclic heterocycle" refers to a 3- to 7-membered monocyclic heterocycle, defined above, which contains at least one ring nitrogen atom. The nitrogen-containing 3- to 7-membered monocyclic heterocycles can be attached via a nitrogen, sulfur, or carbon atom. Representative examples of nitrogen-containing-3- to 7-membered monocyclic heterocycles include, but are not limited to, piperidinyl, piperazinyl, pyrrolyl, oxazinyl, thiazinyl, diazinyl, triazinyl, tetrazinyl, imidazolyl, tetrazolyl, pyrrolidinyl, isoxazolyl, pyridinyl, oxazolyl, thiazolyl, pyrazolyl, triazolyl, pyrimidinyl, and morpholinyl.

A "nitrogen-containing 7- to 10-membered bicyclic heterocycle" refers to a 7- to 10-membered bicyclic heterocycle, defined above, which contains at least one ring nitrogen atom. The nitrogen-containing 7- to 10-membered bicyclic heterocycles can be attached via a nitrogen, sulfur, or carbon atom. Representative nitrogen-containing 7- to 10-membered bicyclic heterocycles include -quinolinyl, -isoquinolinyl, -chromonyl, -indolyl, -isoindolyl, -indolizinyl, -indazolyl, -purinyl, -4H-quinolizinyl, -isoquinolyl, -quinolyl, -phthalazinyl, -naphthyridinyl -carbazolyl, -β-carbolinyl and the like.

The term "-aryl" as used herein, refers to a phenyl or naphthyl group.

"Halo-substituted-($C_1$–$C_5$ alkyl)" refers to a $C_1$–$C_5$ alkyl group, as defined above, wherein one or more of the $C_1$–$C_5$ alkyl group's hydrogen atoms has been replaced with —F, —Cl, —Br or —I. Representative examples of an alkylhalo group include, but are not limited to, —$CH_2F$, —$CCl_3$, —$CF_3$, —$CH_2Cl$, —$CH_2CH_2Br$, —$CH_2CH_2I$, —$CH_2CH_2CH_2F$, —$CH_2CH_2CH_2Cl$, —$CH_2CH_2CH_2CH_2Br$, —$CH_2CH_2CH_2CH_2I$, —$CH_2CH_2CH_2CH_2CH_2Br$, —$CH_2CH_2CH_2CH_2CH_2I$, —$CH_2CH(Br)CH_3$, —$CH_2CH(Cl)CH_2CH_3$, —$CH(F)CH_2CH_3$ and —$C(CH_3)_2(CH_2Cl)$.

"Amino-substituted-($C_1$–$C_5$ alkyl)" refers to a $C_1$–$C_5$ alkyl group, as defined above, wherein one or more of the $C_1$–$C_5$ alkyl group's hydrogen atoms has been replaced with —$NH_2$. Representative examples of an alkyl amino group include, but are not limited to, —$CH_2NH_2$, —$CH_2CH_2NH_2$, —$CH_2CH_2CH_2NH_2$, —$CH_2CH_2CH_2CH_2NH_2$, —$CH_2CH(NH_2)CH_3$, —$CH_2CH(NH_2)CH_2CH_3$, —$CH(NH_2)CH_2CH_3$, —$C(CH_3)_2(CH_2NH_2)$, —$CH_2CH_2CH_2CH_2NH_2$, —$CH_2CH_2CH(NH_2)CH_3$, —$CH_2CH(NH_2)CH_2CH_3$, —$CH_2CH(NH_2)CH_2CH_3$ and —$CH_2C(CH_3)_2(CH_2NH_2)$.

"—(NH($C_1$–$C_5$ alkyl)" refers to an —NH group, the nitrogen atom of said group being attached to a C—$C_5$ alkyl group, as defined above. Representative examples of an aminoalkyl group include, but are not limited to, —$NHCH_3$, —$NHCH_2CH_3$, —$NHCH_2CH_2CH_3$, —$NHCH_2CH_2CH_2CH_3$, —$NHCH(CH_3)_2$, —$NHCH_2CH(CH_3)_2$, —$NHCH_2(CH_3)CH_2CH_3$, —$NH$—$CH_2CH_2C(CH_3)_3$, —$NHCH_2CH_2CH_2CH_2CH_3$, —$NHCH_2CH(CH_3)_2$, —$NHCH_2CH(CH_3)_2$, —$NHCH_2CH(CH_3)CH_2CH_3$ and —$NH$—$CH_2C(CH_3)_3$.

"—N($C_1$–$C_5$ alkyl)($C_1$–$C_5$ alkyl)" refers to a nitrogen atom which has attached to it two $C_1$–$C_5$ alkyl groups, as defined above. Representative examples of a aminodialkyl group include, but are not limited to, —$N(CH_3)_2$, —$N(CH_2CH_3)(CH_3)$, —$N(CH_2CH_3)_2$, —$N(CH_2CH_2CH_3)_2$, —$N(CH_2CH_2CH_2CH_3)_2$, —$N(CH(CH_3)_2)_2$, —$N(CH(CH_3)_2)(CH_3)$, —$N(CH_2CH(CH_3)_2)_2$, —$NH(CH(CH_3)CH_2CH_3)_2$, —$N(C(CH_3)_3)_2$ and —$N(C(CH_3)_3)(CH_3)$.

"—($H_2NC(O)$)-substituted aryl" refers to an aryl group, as defined above, wherein one of the aryl group's hydrogen atoms has been replaced with one or more —$C(O)NH_2$ groups. Representative examples of an arylamido group include 2-C(O)$NH_2$-phenyl, 3-C(O)$NH_2$-phenyl, 4-C(O)$NH_2$-phenyl.

"—($H_2NC(O)$)-substituted pyridyl" refers to an pyridyl group, wherein one of the pyridyl group's hydrogen atoms has been replaced with one or more —$C(O)NH_2$ groups. Representative examples of an arylamido group include 2–C(O)$NH_2$-pyridyl, 3-C(O)$NH_2$-pyridyl and 4-C(O)$NH_2$-pyridyl.

"—($H_2NC(O)$)-substituted-($C_1$–$C_5$ alkyl)" refers to a $C_1$–$C_5$ alkyl group, as defined above, wherein one of the $C_1$–$C_5$ alkyl group's hydrogen atoms has been replaced with a —$C(O)NH_2$ group. Representative examples of an alkylamido group include, but are not limited to, —$CH_2C(O)NH_2$, —$CH_2CH_2C(O)NH_2$, —$CH_2CH_2CH_2C(O)NH_2$, —$CH_2CH_2CH_2CH_2C(O)NH_2$, —$CH_2CH_2CH_2CH_2CH_2C(O)NH_2$, —$CH_2CH(C(O)NH_2)CH_3$, $CH_2CH(C(O)NH_2)CH_2CH_3$, —$CH(C(O)NH_2)CH_2CH_3$ and —$C(CH_3)_2CH_2C(O)NH_2$.

"HO-substituted-($C_1$–$C_5$ alkyl)" refers to a $C_1$–$C_5$ alkyl group, as defined above, wherein one of the $C_1$–$C_5$ alkyl group's hydrogen atoms has been replaced with a hydroxyl group. Representative examples of an alkanol group include, but are not limited to, —$CH_2OH$, —$CH_2CH_2OH$, —$CH_2CH_2CH_2OH$, —$CH_2CH_2CH_2CH_2OH$, —CH$_2$CH$_2$CH$_2$CH$_2$CH$_2$OH, —CH$_2$CH(OH)CH$_3$, —CH$_2$CH(OH)CH$_2$CH$_3$, —CH(OH)CH$_2$CH$_3$ and —C(CH$_3$)$_2$CH$_2$OH.

"Carboxy-substituted-(C$_1$–C$_5$ alkyl)" refers to a C$_1$–C$_5$ alkyl group, as defined above, wherein one of the C$_1$–C$_5$ alkyl group's hydrogen atoms has been replaced with a —COOH group. Representative examples of an alkylcarboxy group include, but are not limited to, —CH$_2$COOH, —CH$_2$CH$_2$COOH, —CH$_2$CH$_2$CH$_2$COOH, —CH$_2$CH$_2$CH$_2$CH$_2$COOH, —CH$_2$CH(COOH)CH$_3$, —CH$_2$CH$_2$CH$_2$CH$_2$CH$_2$COOH, —CH$_2$CH(COOH)CH$_2$CH$_3$, —CH(COOH)CH$_2$CH$_3$ and —C(CH$_3$)$_2$CH$_2$COOH.

The term "glycoside" as used herein refers to a hexose or a pentose sugar forming an α- or β-glycosidic linkage. Representative examples of glycosides include, but are not limited to ribose, deoxyribose, fructose, galactose, glucuronic acid and glucose.

A "subject" is a mammal, e.g., a human, mouse, rat, guinea pig, dog, cat, horse, cow, pig, or non-human primate, such as a monkey, chimpanzee, or baboon.

The phrase "pharmaceutically acceptable salt," as used herein, is a salt formed from an acid and a basic nitrogen group of one of the Tetracyclic Benzamide Derivatives. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-OH-3-naphthoate)) salts. The term "pharmaceutically acceptable salt" also refers to a salt prepared from a Tetracyclic benzamide Derivative having an acidic functional group, such as a carboxylic acid functional group or a sulfonic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-OHethyl)amine, 2-OH tert-butylamine, or tris-(hydroxymethyl)methylamine, N,N-di-lower alkyl-N-(hydroxy lower alkyl)-amines, such as N,N-dimethyl-N-(2-hydroxyethyl)amine or tri-(2-OHethyl)amine; N-methyl-D-glucamine; and amino acids such as arginine, lysine, and the like.

An "effective amount" when used in connection a Tetracyclic Benzamide Derivative is an amount effective for: (a) treating or preventing a Condition or (b) inhibiting PARP in an in vivo or an in vitro cell.

The following abbreviations are used herein and have the indicated definitions: AcOH is acetic acid, CEP is Cecal Ligation and Puncture, DMEM is Dulbecco's Modified Eagle Medium, DMF is N,N-dimethylformamide, DMSO is dimethylsulfoxide, Et is ethyl, EtOAc is ethyl acetate, EtOH is ethanol, HEPES is 4-(2-hydroxyethyl)-1-piperazineethanesulfonic acid, HPLC is high performance liquid chromatography, LPS is lipopolysaccharide, MeCN is acetonitrile, MeOH is methanol, MS is mass spectrometry, Ms is mesyl (methanesulfonyl), NaBH$_4$ is sodium borohydride, NEt$_3$ is triethylamine, NMR is nuclear magnetic resonance, PBS is phosphate-buffered saline (pH 7.4), PARP is poly (ADP-ribose)polymerase, PPA is polyphosphoric acid, Py is pyridine, SDS is dodecyl sulfate (sodium salt), STZ is streptozotocin, TCA is tricholoroacetic acid, Tf is triflyl (trifluoromethanesulfonyl), TFA is trifluoroacetic acid, THF is tetrahydrofuran; TLC is thin-layer chromatography, TNF is tumor necrosis factor, TRIS is Tris(hydroxymethyl)aminomethane and Ts is tosyl (p-toluenesulfonyl).

4.16 Methods for Making the Tetracyclic Benzamide Derivatives

Examples of synthetic pathways useful for making Tetracyclic Benzamide Derivatives are set forth in the Examples below and generalized in Schemes 1–6.

Scheme 1 illustrates methods useful for making Tetracyclic Benzamide Derivatives of Formula (IIa), where R$_1$–R$_4$ and R$_6$–R$_{10}$ are defined for Formula (IIa).

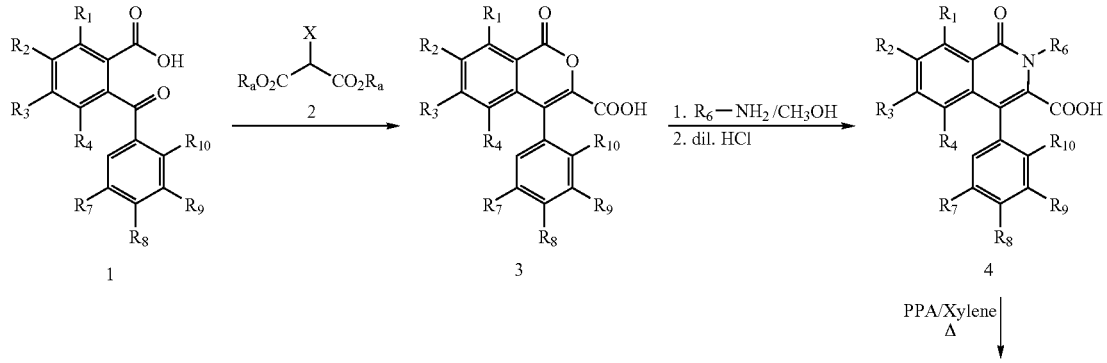

Scheme 1

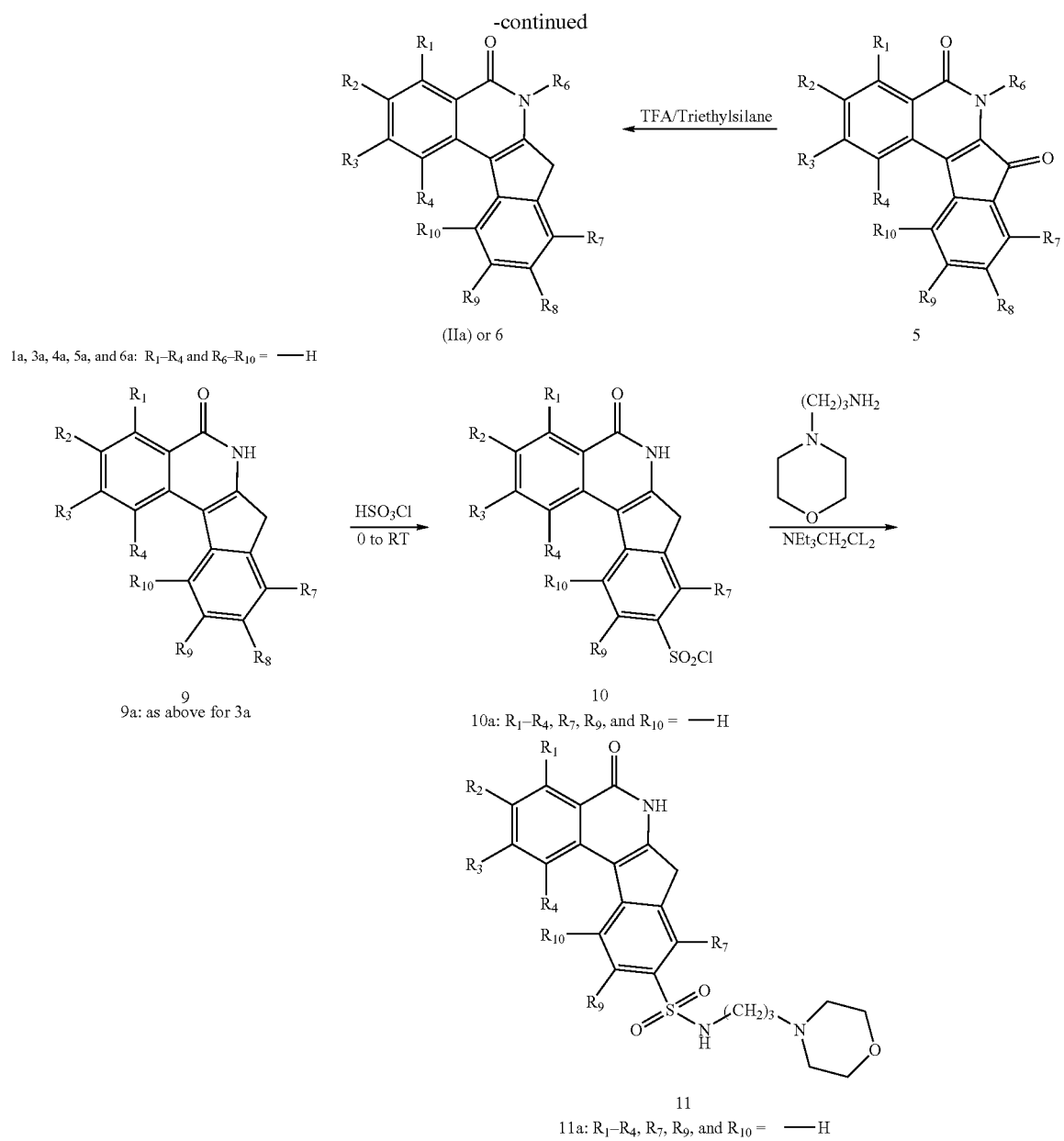

wherein

R$_1$–R$_4$ and R$_6$–R$_{10}$ are as defined above for the compounds of Formula (IIa);

each R$_a$ is independently C$_1$–C$_3$ alkyl; and X is —Cl, —Br, —I, —OTf, —OMs or —OTs.

Tetracyclic Benzamide Derivatives of Formula (II) and Formula (IIa) can be made by a method comprising the steps of Scheme 1 above herein.

A compound of Formula 3 can be made by a method comprising contacting a compound of Formula 1 with a compound of Formula 2 in the presence of a base for a time and at a temperature sufficient to make a compound of Formula 3.

In one embodiment R$_a$ is methyl and X is —Br.

In one embodiment about 0.1 to about 10 equivalents of a compound of Formula 2 are used per about 1 equivalent of a compound of Formula 1.

In another embodiment about 0.5 to about 5 equivalents of a compound of Formula 2 are used per about 1 equivalent of a compound of Formula 1.

In still another embodiment, about 1 to about 2 equivalents of a compound of Formula 2 are used per about 1 equivalent of a compound of Formula 1.

In one embodiment about 1 to about 5 equivalents of base are used per about 1 equivalent of a compound of Formula 1.

In another embodiment about 2 to about 3 equivalents of base are used per about 1 equivalent of a compound of Formula 1.

Suitable bases for use in the method are organic bases such as triethylamine, diisopropylamine, diisopropylethylamine, pyridine, lutidine and imidazole; and inorganic bases such as alkali metal carbonates, including sodium carbonate, potassium carbonate and cesium carbonate.

In another embodiment, the base is potassium carbonate.

The method can be carried out in the presence of a solvent, such as acetonitrile, methylene chloride, chloroform, THF, DMF, DMSO, ethyl acetate, acetone, benzene, diethyl ether, water or mixtures thereof.

In another embodiment, the solvent is DMF.

In still another embodiment, the solvent is substantially anhydrous, i.e., comprises less than about 1% water.

In another embodiment the method is carried out for a time of about 2 hours to about 36 hours.

In still another embodiment the method of Scheme 1 is carried out for a time of about 8 hours to about 24 hours.

In yet another embodiment the method of Scheme 1 is carried out for a time of about 12 hours to about 18 hours.

In a further embodiment, the method of Scheme 1 is carried out at a temperature of about 0° C. to about 100° C.

In another embodiment, the method of Scheme 1 is carried out at a temperature of about 35° C. to about 70° C.

In yet another embodiment, the method of Scheme 1 is carried out at a temperature of about 25° C.

A compound of Formula 4 can be made by a method comprising (a) contacting a compound of Formula 3 with ammonia in methanol; and (b) contacting the product of step (a) with dilute acid for a time and at a temperature sufficient to make a compound of Formula 4.

In one embodiment about 1 to about 1000 equivalents of a solution of ammonia in methanol are used per about 1 equivalent of a compound of Formula 3.

In another embodiment about 5 to about 500 equivalents of ammonia in methanol are used per about 1 equivalent of a compound of Formula 3.

In still another embodiment, about 10 to about 100 equivalents of ammonia in methanol are used per about 1 equivalent of a compound of Formula 3.

In yet another embodiment about 20 to about 50 equivalents of ammonia in methanol are used per about 1 equivalent of a compound of Formula 3.

In one embodiment the ammonia in methanol is from about 1 N to about 10 N.

In another embodiment the ammonia in methanol is from about 3 N to about 7 N.

In one embodiment the dilute acid is from about 0.01 N to about 3 N.

In another embodiment the dilute acid is from about 0.1 N to about 1 N.

In another embodiment, the acid is HCl.

In one embodiment the method is carried out for a time of about 1 hour to about 48 hours.

In still another embodiment the method is carried out for a time of about 8 hours to about 36 hours.

In yet another embodiment the method is carried out for a time of about 12 hours to about 24 hours.

In one embodiment, the method is carried out at a temperature of about 0° C. to about 100° C.

In another embodiment, the method is carried out at a temperature of about 25° C. to about 75° C.

In yet another embodiment, the method is carried out at a temperature of about 40° C. to about 60° C.

A compound of Formula 5 can be made by a method comprising contacting a compound of Formula 4 with a dehydrating agent for a time and at a temperature sufficient to make a compound of Formula 5.

In one embodiment about 0.1 to about 10 equivalents of a dehydrating agent are used per about 1 equivalent of a compound of Formula 4.

In another embodiment about 0.5 to about 5 equivalents of a dehydrating agent are used per about 1 equivalent of a compound of Formula 4.

In still another embodiment, about 1 to about 2 equivalents of a dehydrating agent are used per about 1 equivalent of a compound of Formula 4.

Suitable dehydrating agents include, but are not limited to, PPA, sulfuric acid, chlorosulfonic acid, sulfuryl chloride and thionyl chloride.

In another embodiment, the dehydrating agent is PPA.

The method can be carried out in the presence of a solvent, including, but not limited to, xylenes.

In one embodiment, the solvent is xylenes.

In another embodiment, the solvent is substantially anhydrous, i.e., comprises less than about 1% water.

In one embodiment the method is carried out for a time of about 1 hour to about 24 hours.

In still another embodiment the method is carried out for a time of about 4 hours to about 18 hours.

In yet another embodiment the method is carried out for a time of about 6 hours to about 12 hours.

In one embodiment, the method is carried out at a temperature of about 25° C. to about 200° C.

In another embodiment, the method is carried out at a temperature of about 100° C. to about 160° C.

A compound of Formula (IIa) can be made by a method comprising contacting a compound of Formula 5 with a reducing agent for a time (e.g. Wolff-Kishner reagents) and at a temperature sufficient to make a compound of Formula (IIa).

In one embodiment about 0.1 to about 10 equivalents of a reducing agent are used per about 1 equivalent of a compound of Formula 5.

In another embodiment about 0.5 to about 5 equivalents of a reducing agent are used per about 1 equivalent of a compound of Formula 5.

In still another embodiment, about 1 to about 2 equivalents of a reducing agent are used per about 1 equivalent of a compound of Formula 5.

Suitable reducing agents for this carbonyl reduction include, but are not limited to, sodium borohydride, diisobutylaluminum hydride, alpineborane, and TFA/triethylsilane.

In one embodiment, the reducing agent is a hydride reducing agent.

In another embodiment, the reducing agent is sodium borohydride.

In another embodiment, the reducing agent is TFA/triethylsilane.

The method can be carried out in the presence of a solvent, including, but not limited to, methanol, ethanol, THF and benzene. Alternatively the method can be carried out in the absence of a solvent.

In one embodiment, the solvent is methanol.

In another embodiment, the solvent is substantially anhydrous, i.e., comprises less than about 1% water.

In one embodiment the method is carried out for a time of about 1 minute to about 12 hours.

In still another embodiment the method is carried out for a time of about 5 minutes hours to about 6 hours.

In yet another embodiment the method is carried out for a time of about 15 minutes hours to about 2 hours.

In one embodiment, the method is carried out at a temperature of about −20° C. to about 40° C.

In another embodiment, the method is carried out at a temperature of about 10° C. to about 30° C.

In still another embodiment, the method is carried out at a temperature of about 25° C.

A Tetracyclic Benzamide Derivative of the Formula 9 can be further derivatized using methodology familiar to one skilled in the art of organic synthesis to prepared a variety of analogs of Formula (II) and Formula (IIa) having various substituents at one or more of $R_1$, $R_2$, $R_3$, $R_4$, $R_7$, $R_8$, $R_9$ and $R_{10}$. Useful derivatization methods include, but are not limited to, aromatic nucleophilic substitution reactions and aromatic electrophilic substitution reactions, such as nitration, iodination, bromination, chlorination, sulfonylation, sulfonylchlorination, alkylation and acylation. See M. B. Smith and J. March, *Advanced Organic Chemistry: Reactions, Mechanisms, and Structure* 675–758 and 850–893 (5$^{th}$ ed. 2001).

In one embodiment, the Tetracyclic Benzamide Derivative of Formula 9 is transformed into the chlorosulfonyl compound of Formula 10 using chlorosulfonic acid. The Chlorosulfonyl compound of Formula 10 is then derivatized to the corresponding 3-(N morpholinyl)-propylsulfonamide derivative of Formula 11 by reacting the chlorosulfonyl compound of 10 with 3-(N-morpholinyl)-propylamine in the presence of a triethylamine.

Scheme 2 below illustrates methods useful for making compounds of Formula (I), Formula (Ia) and Formula (Ib), wherein $R_1$–$R_4$ and $R_7$–$R_{11}$ are defined above for the compounds of Formula (I), Formula (Ia) and Formula (Ib); X' is —OH, —NHR$_{11}$, or —SH; X is —O—, —N(H)—, or —S—; each $R_a$ is independently $C_1$-$C_3$ alkyl; and $R_b$ is —Cl, —Br, —I, —OTs, —OMs or —OTf.

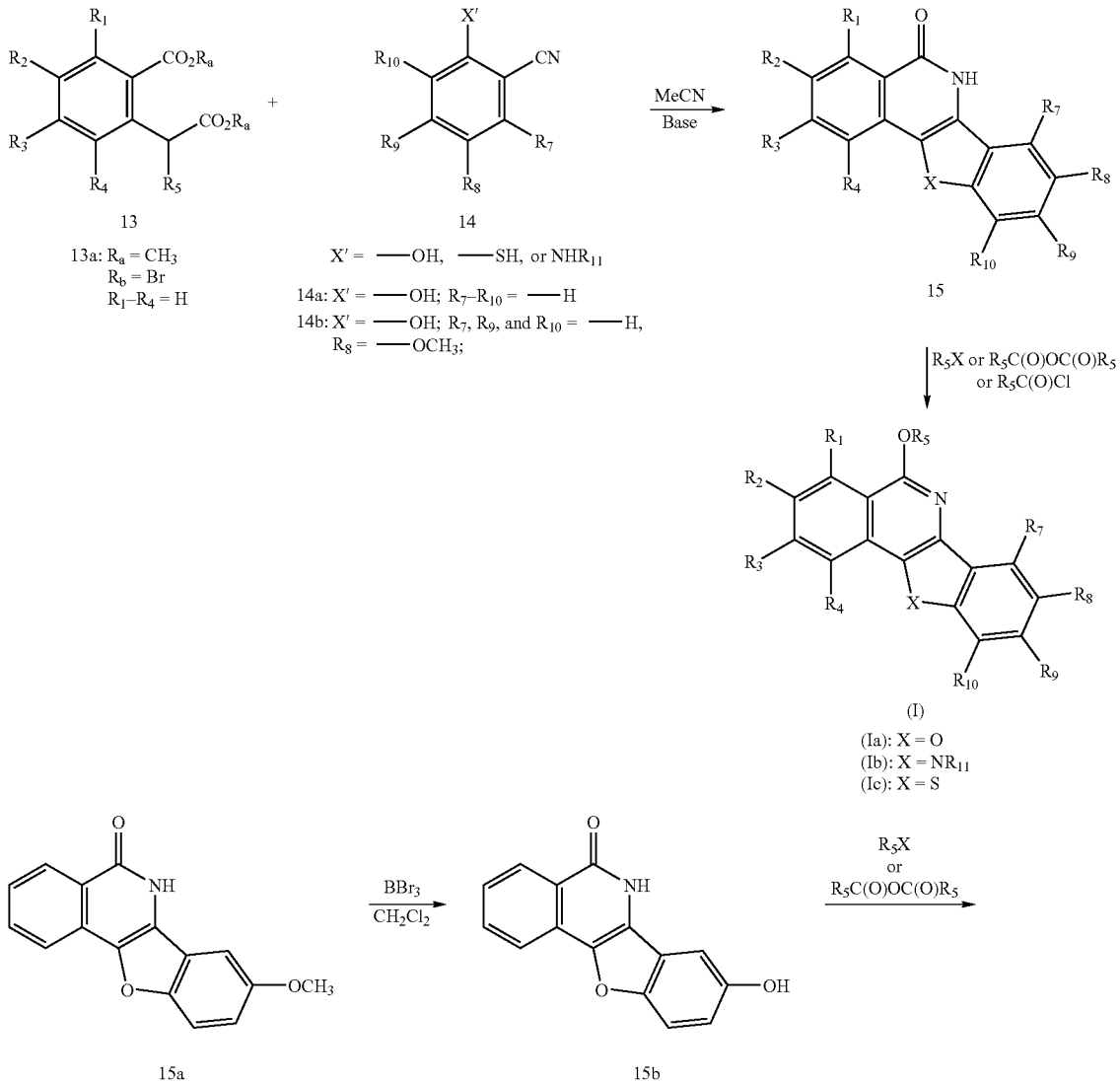

-continued
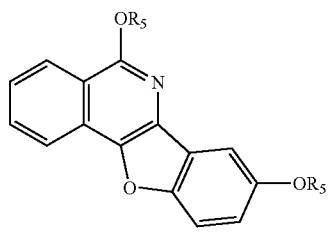
16
16a: R$_5$ = —CH$_2$COOH
16b: R$_5$ = —(CH$_2$)$_3$COOH
16c: R$_5$ = —(CH$_2$)$_5$(OH)
16d: R$_5$ = —(CH$_2$)$_6$(OH)
16e: R$_5$ = —(CH$_2$)$_4$COOH
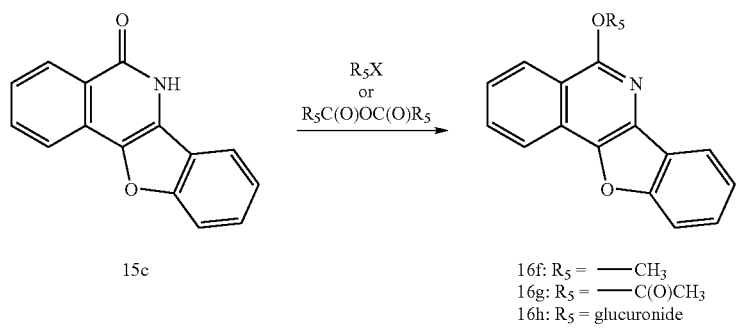
16f: R$_5$ = —CH$_3$
16g: R$_5$ = —C(O)CH$_3$
16h: R$_5$ = glucuronide
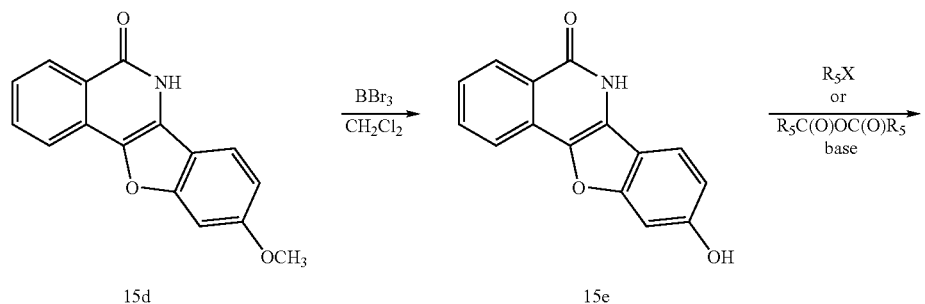
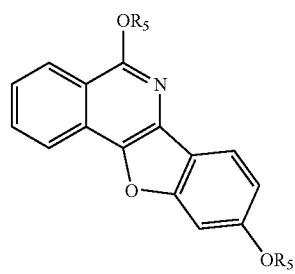
16i: R$_5$ = —CH$_3$
16j: R$_5$ = —(CH$_2$)$_3$OH
16k: R$_5$ = —(CH$_2$)$_3$OH A tetracyclic isoquinoline compound of Formula 15 can be prepared by reacting a homophthalate of Formula 13 with a cyanophenol of Formula 14 in the presence of a base, such as triethylamine, sodium carbonate, or potassium carbonate, in a solvent such as acetonitrile, acetone or dimethylformamide (DMF).

A compound of Formula 15 can be transformed to a Tetracyclic Benzamide Derivative of Formula (I) upon treating 15 with an alkylating agent, an acylating agent or a glucuronidating agent, and further derivatization if necessary.

Suitable alkylating and acylating agents include, but are not limited to, alkylhalides, such as iodomethane, iodoethane, 1-iodopropane and 2-bromopropane, 1-bromopropane, 1-bromobutane, 1-bromopentane and 1-bromohexane, the alkyl group of which can be optionally substituted with —OH or —C(O)OH; acyl halides, such as acetyl chloride and propionyl chloride; and anhydrides, such as acetic anhydride and propionic anhydride.

In one embodiment, the alkylating agent is methyl iodide.

In another embodiment, the allkylating agent is a hydroxy-substituted alkylhalide.

In still another embodiment, the alkylating agent is a carboxy-substituted alkylhalide.

In one embodiment, the acylating agent is acetyl chloride.

In another embodiment, the acylating agent is acetic anhydride.

In yet another embodiment, $R_5$ is glucuronidyl and the glucuronidating agent is acetobromo-α-D-glucuronic acid methyl ester.

Scheme 3 below illustrates methodology useful for making Tetracyclic Benzamide Derivatives of Formula III, wherein $R_1$–$R_4$ and $G_1$–$G_4$ are defined above for the compounds of Formula III; $R_b$ is —Cl, —Br, —I, —OTs, —OMs or —OTf; and $R_c$ is —$C_1$–$C_3$ alkyl.

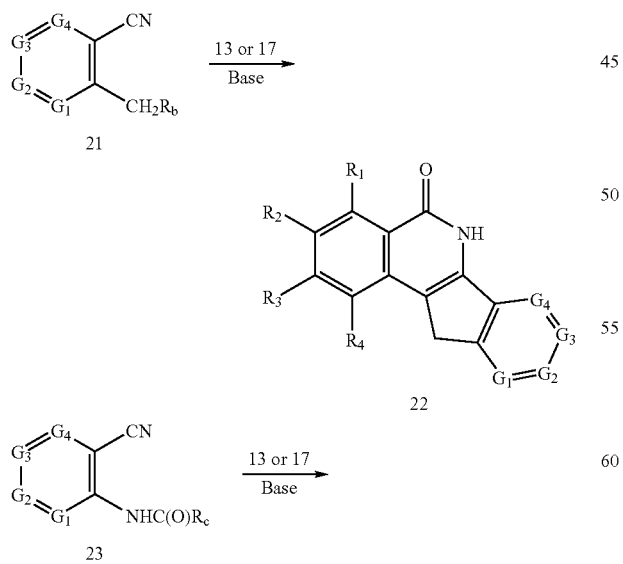

Scheme 3

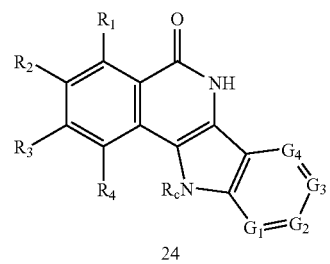

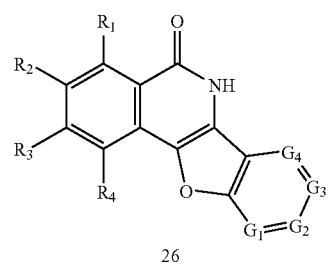

26a: $R_1$–$R_4$ = H; $G_2$–$G_4$ = CH; $G_1$ = N

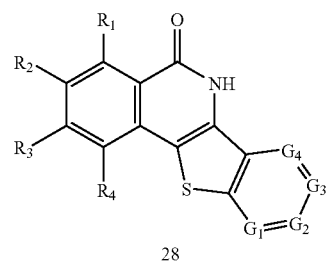

Tetracyclic Benzamide Devivatives Derivatives of Formulas 22, 24, 26 and 28 can be made by reacting a homophthalic anhydride of Formula 17 with a compound of Formula 21, 23, 25 or 27, respectively in the presence of a base.

In an alternate embodiment, Tetracyclic Benzamide Devivatives Derivatives of Formulas 22, 24, 26 and 28 can be made by reacting a homophthalate of Formula 13 with a compound of Formula 21, 23, 25 or 27, respectively in the presence of a base.

Suitable bases for use in the methods of Scheme 5 are organic bases such as triethylamine, diisopropylamine, diisopropylethylamine, pyridine, lutidine sodium butoxide, sodium methoxide, and imidazole; and inorganic bases such as alkali metal carbonates, including sodium hydride, sodium carbonate, potassium carbonate and cesium carbonate.

In one embodiment, the base is triethylamine.

In another embodiment, the base is potassium carbonate.

The method can be carried out in the presence of a solvent, such as acetonitrile, methylene chloride, chloroform, THF, DMF, DMSO, ethyl acetate, acetone, benzene, diethyl ether, water or mixtures thereof.

In one embodiment, the solvent is acetonitrile.

In another embodiment, the solvent is DMF.

Scheme 4 below illustrates methods useful for making compounds of Formula (V) wherein $R_1$–$R_4$ and $R_7$–$R_{10}$ are defined above for the compounds of Formula (V).

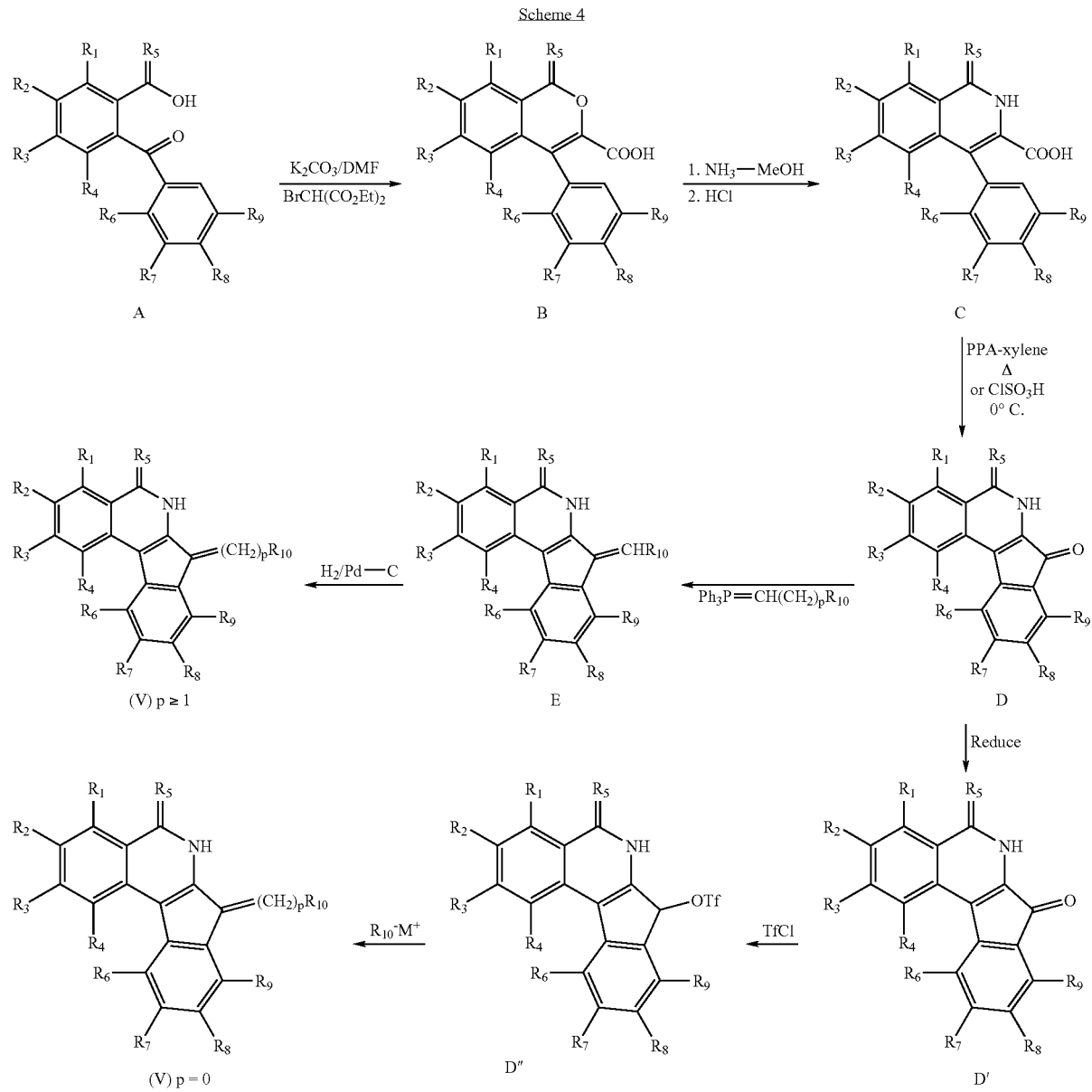

Scheme 4

A ketone of Formula A can be cyclized to the bicyclic intermediates of Formula B using bromo ethyl malonate in the presence of potassium carbonate. The intermediates of Formula B can then be converted to the lactam intermediates of Formula C in the presence of ammonia in methanol. Fridel-Crafts mediated ring closure of C provides the tetracyclic keto intermediates of Formula D which when reacted with a phosponate or phosphorus ylide via a Wittig-Homer procedure provides the Tetracyclic Benzamide Derivatives of Formula E, whose exocyclic double bond can subsequently be reduced using catalytic hydrogenation to provide the compounds of Formula (V) where p is ≧2.

In an alternate embodiment, compounds of Formula (V) where p=0, can be synthesized via intermediates of Formula D. The keto intermediates of Formula D can be reduced to the corresponding alcohol intermediates of Formula D' with subsequent conversion of the alcohol to the triflate intermediates of Formula D" to produce a good leaving group. The triflate intermediate can then be reacted with nucleophiles of the Formula $R_{10}^-M^+$ where $M^+$ is a alkali metal such as $Na^+$, or $K^+$, thereby producing Tetracyclic Benzamide Derivatives of Formula (V) where p=0. The compounds of Formula A can be produced from commercially starting materials using techniques known to one skilled in the art of organic synthesis.

Scheme 5 below illustrates methods useful for making compounds of Formula (II), Formula (VI), Formula (VII), Formula (VIIa), Formula (VIIb), and Formula (VIIc) wherein $R_1$–$R_4$, $R_7$–$R_{10}$, $G_1$–$G_4$, and X are defined above for the compounds of Formula (II), Formula (VI), Formula (VII), Formula (VIIa), Formula (VIIb), and Formula (VIIc):

SCHEME 5

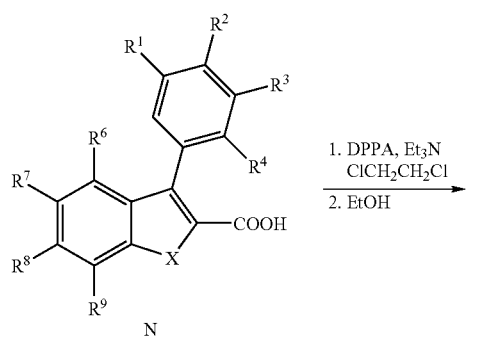

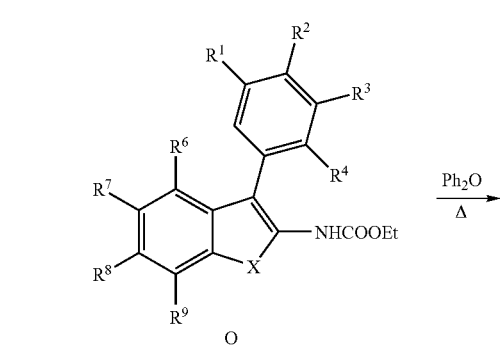

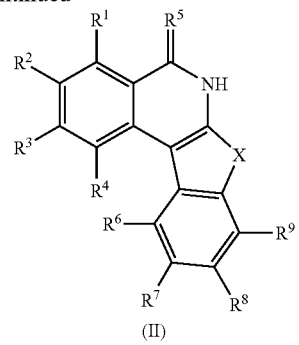
(II)

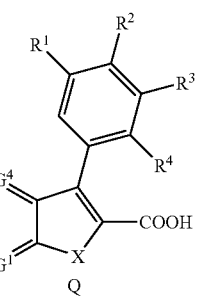

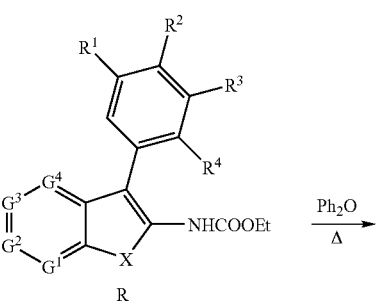

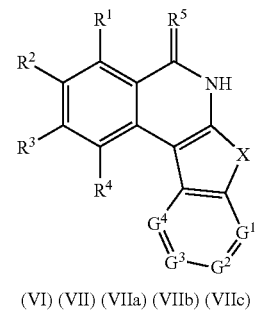
(VI) (VII) (VIIa) (VIIb) (VIIc)

The carboxylic acid group of a compound of Formula N can be coupled with DPPA to provide the corresponding carbamate intermediates of Formula O, which can then be thermally cyclized to provide the Tetracyclic Benzamide derivatives of Formula (II). Using the same synthetic method, the bicyclic carboxylic acids of Formula Q (see Wacker et al., Tet. Lett., 43:5189–5191, 2002; and Bourdais, et al., J. Het. Chem., 12:1111–1115, 1975, for methods useful to make compounds of Formula Q) can be converted to the Tetracyclic Benzamide derivatives of Formula (VI), Formula (VII), Formula (VIIa), Formula (VIIb), and Formula (VIIc) via the intermediacy of the carbamates of Formula R.

Scheme 6 below illustrates methods useful for making compounds of Formula (IV) wherein $R_1$–$R_4$, $R_7$–$R_{10}$, and $G_1$–$G_4$ are defined above for the compounds of Formula (IV):

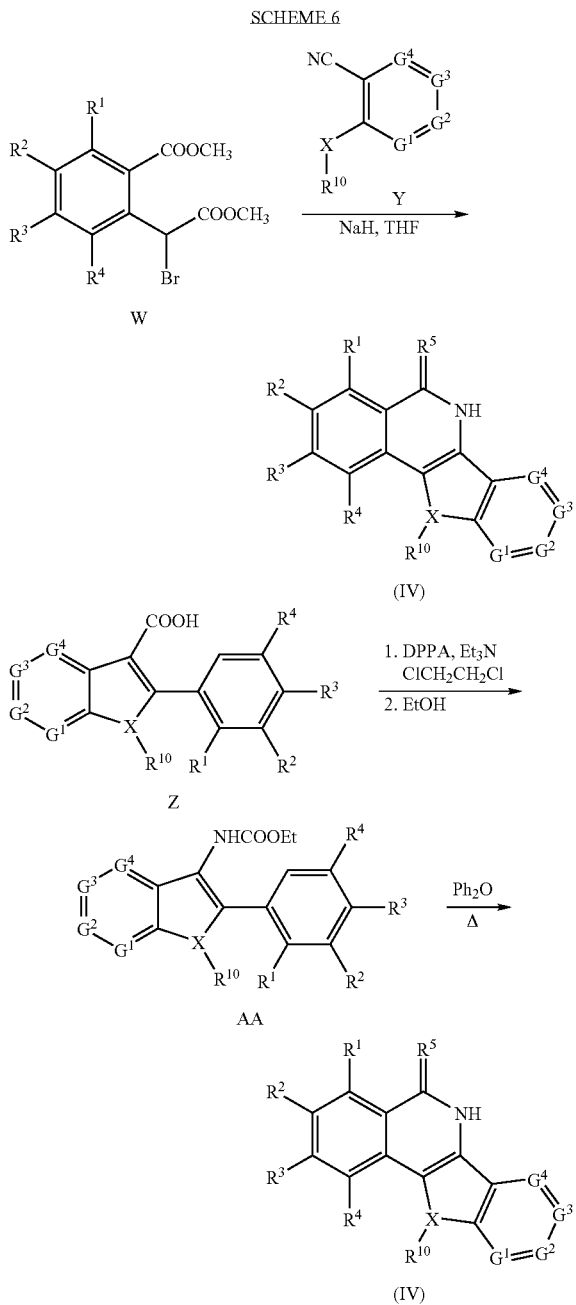

The Tetracyclic Benzamide Derivatives of Formula (IV) can be made using a one pot coupling/cyclization process by reacting an intermediate of Formula W with an aromatic nitrile of Formula Y in the presence of sodium hydride.

Alternatively, the carboxylic acid group of a compound of Formula Z (see Wacker et al., Tet. Lett., 43:5189–5191, 2002; and Bourdais, et al., J. Het. Chem., 12:1111–1115, 1975, for methods useful to make compounds of Formula Z) can be coupled with DPPA to provide the corresponding carbonate intermediates of Formula AA, which can then be thermally cyclized to provide the Tetracyclic Benzamide Derivatives of Formula (IV).

4.17 Therapeutic Uses of the Tetracyclic Benzamide Derivatives

The invention also includes pharmaceutical compositions comprising an effective amount of a Tetracyclic Benzamide Derivative and a pharmaceutically acceptable carrier or vehicle. The invention includes a Tetracyclic Benzamide Derivative when provided as a pharmaceutically acceptable prodrug, hydrated salt, such as a pharmaceutically acceptable salt, or mixtures thereof.

In accordance with the invention, the Tetracyclic Benzamide Derivatives are administered to a subject in need of treatment or prevention of a Condition.

The Tetracyclic Benzamide Derivatives can be used to treat or prevent an inflammatory disease. Inflammatory diseases can arise where there is an inflammation of the body tissue. These include local inflammatory responses and systemic inflammation. Examples of inflammatory diseases treatable or preventable using the Tetracyclic Benzamide Derivatives include, but are not limited to, organ transplant rejection; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, and chronic obstructive airway disease; inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney including uremic complications, glomerulonephritis and nephrosis; inflammatory diseases of the skin including dermatitis, sclerodermatitis, psoriasis and eczema; inflammatory diseases of the central nervous system, including chronic demyelinating diseases of the nervous system, multiple sclerosis, AIDS-related neurodegeneration and Alzheimers disease, infectious meningitis, encephalomyelitis, Parkinson's disease, Huntington's disease, amyotrophic lateral sclerosis and viral or autoimmune encephalitis; immune-complex vasculitis; systemic lupus erythematosus (SLE); inflammatory diseases of the heart such as cardiomyopathy, ischemic heart disease, hypercholesterolemia, and atherosclerosis; as well as various other diseases that can have significant inflammatory components, including preeclampsia, chronic liver failure, and brain and spinal cord trauma. The inflammatory disease can also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

In one embodiment the inflammatory disease is arthritis. In another embodiment the inflammatory disease is colitis.

The Tetracyclic Benzamide Derivatives can be used to treat or prevent a reperfusion disease. Reperfusion refers to the process whereby blood flow in the blood vessels is resumed following ischemia, such as occurs following constriction or obstruction of the vessel. Reperfusion disease can result following a naturally occurring episode, such as a myocardial infarction, stroke, or during a surgical procedure where blood flow in vessels is intentionally or unintentionally blocked. Examples of reperfusion injuries treatable or preventable using the Tetracyclic Benzamide Derivatives include, but are not limited to, intestinal reperfusion disease, myocardial reperfusion disease, and reperfusion disease resulting from cardiopulmonary bypass surgery, thoracoabrominal aneurysm repair surgery, carotid endarerectomy surgery, or hemorrhagic shock.

In one embodiment, the reperfusion disease results from cardiopulmonary bypass surgery, thoracoabrominal aneurysm repair surgery, carotid endarerectomy surgery, or hemorrhagic shock.

In one embodiment, the reperfusion disease is a reoxygenation injury resulting from surgery, particularly that relating to organ transplantation.

The Tetracyclic Benzamide Derivatives can be used to treat or prevent a reoxygenation injury resulting from surgery, particularly that relating to organ transplantation. Examples of reoxygenation injuries treatable or preventable using the Tetracyclic Benzamide Derivatives include, but are not limited to, transplantation of the following organs: heart, lung, liver and kidney.

In one embodiment, a reoxygenation injury resulting from organ transplantation occurs during the organ transplantation.

The Tetracyclic Benzamide Derivatives can be used to treat or prevent an ischemic condition. Examples of ischemic conditions treatable or preventable using the Tetracyclic Benzamide Derivatives include, but are not limited to, stable angina, unstable angina, myocardial ischemia, hepatic ischemia, mesenteric artery ischemia, intestinal ischemia, critical limb ischemia, chronic critical limb ischemia, erebral ischemia, acute cardiac ischemia, and an ischemic disease of the central nervous system, such as stroke or cerebral ischemia.

In one embodiment, the ischemic condition is myocardial ischemia, stable angina, unstable angina, stroke, ischemic heart disease or cerebral ischemia.

The Tetracyclic Benzamide Derivatives can be used to treat or prevent chronic renal failure. In one embodiment the renal failure is chronic renal failure. In another embodiment, the renal failure is acute renal failure.

The Tetracyclic Benzamide Derivatives can be used to treat or prevent a vascular disease. Examples of vascular diseases treatable or preventable using the Tetracyclic Benzamide Derivatives include, but are not limited to, peripheral arterial occlusion, thromboangitis obliterans, Reynaud's disease and phenomenon, acrocyanosis, erythromelalgia, venous thrombosis, varicose veins, arteriovenous fistula, lymphedema, and lipedema.

In one embodiment the vascular disease is a cardiovascular disease. The Tetracyclic Benzamide Derivatives can be used to treat or prevent cardiovascular diseases. Examples of cardiovascular diseases treatable or preventable using the Tetracyclic Benzamide Derivatives include, but are not limited to, cardiovascular diseases that can be treated or prevented by administering an effective amount of a Tetracyclic Benzamide Derivative include, but are not limited to, chronic heart failure, atherosclerosis, congestive heart failure, circulatory shock, cardiomyopathy, cardiac transplant, myocardial infarction, and a cardiac arrhythmia, such as atrial fibrillation, supraventricular tachycardia, atrial flutter, and paroxysmal atrial tachycardia.

In one embodiment, the cardiovascular disease is chronic heart failure.

In another embodiment, the cardiovascular disease is a cardiac arrhyhmia.

In still another embodiment, the cardiac arrhythmia is atrial fibrillation, supraventricular tachycardia, atrial flutter or paroxysmal atrial tachycardia.

The Tetracyclic Benzamide Derivatives can be used to treat or prevent diabetes. Examples of diabetes treatable or preventable or preventable using the Tetracyclic Benzamide Derivatives include, but are not limited to, Type I diabetes (Insulin Dependent Diabetes Mellitus), Type II diabetes (Non-Insulin Dependent Diabetes Mellitus), gestational diabetes, insulinopathies, diabetes due to pancreatic disease, diabetes associated with other endocrine diseases (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by $\beta$-cell toxins.

The Tetracyclic Benzamide Derivatives can be used to treat or prevent a diabetic complication. Examples of diabetic complications treatable or preventable or preventable using the Tetracyclic Benzamide Derivatives include, but are not limited to, diabetic cataract, glaucoma, retinopathy, nephropathy, (such as microaluminuria and progressive diabetic nephropathy), polyneuropathy, gangrene of the feet, atherosclerotic coronary arterial disease, peripheral arterial disease, nonketotic hyperglycemic-hyperosmolar coma, mononeuropathy, autonomic neuropathy, foot ulcer, joint problem, and a skin or mucous membrane complication (such as an infection, a shin spot, a candidal infection or necrobiosis lipoidica diabeticorumobesity), hyperlipidemia, hypertension, syndrome of insulin resistance, coronary artery disease, retinopathy, diabetic neuropathy, polyneuropathy, mononeuropathy, autonomic neuropathy, foot ulcers, joint problems, fungal infections, and bacterial infections.

4.17.1 Treatment or Prevention of Cancer

The Tetracyclic Benzamide Derivatives can be used to treat or prevent cancer. Examples of cancers treatable or preventable using the Tetracyclic Benzamide Derivatives include, but are not limited to, the cancers disclosed below in Table 1 and metastases thereof.

TABLE 1

| Solid tumors, including but not limited to: |
| --- |
| fibrosarcoma |
| myxosarcoma |
| liposarcoma |
| chondrosarcoma |
| osteogenic sarcoma |
| chordoma |
| angiosarcoma |
| endotheliosarcoma |
| lymphangiosarcoma |
| lymphangioendotheliosarcoma |
| synovioma |
| mesothelioma |
| Ewing's tumor |
| leiomyosarcoma |
| rhabdomyosarcoma |
| colon cancer |
| colorectal cancer |
| kidney cancer |
| pancreatic cancer |
| bone cancer |
| breast cancer |
| ovarian cancer |

TABLE 1-continued prostate cancer
esophageal cancer
stomach cancer
oral cancer
nasal cancer
throat cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular cancer
small cell lung carcinoma
bladder carcinoma
lung cancer
epithelial carcinoma
glioma
glioblastoma multiforme
astrocytoma
medulloblastoma
craniopharyngioma
ependymoma
pinealoma
hemangioblastoma
acoustic neuroma
oligodendroglioma
meningioma
skin cancer
melanoma
neuroblastoma
retinoblastoma
blood-borne cancers, including but not limited to:

acute lymphoblastic leukemia ("ALL")
acute lymphoblastic B-cell leukemia
acute lymphoblastic T-cell leukemia
acute myeloblastic leukemia ("AML")
acute promyelocytic leukemia ("APL")
acute monoblastic leukemia
acute erythroleukemic leukemia
acute megakaryoblastic leukemia
acute myelomonocytic leukemia
acute nonlymphocytic leukemia
acute undifferentiated leukemia
chronic myelocytic leukemia ("CML")
chronic lymphocytic leukemia ("CLL")
hairy cell leukemia
multiple myeloma
acute and chronic leukemias:

lymphoblastic
myelogenous
lymphocytic
myelocytic leukemias
Lymphomas:

Hodgkin's disease
non-Hodgkin's Lymphoma
Multiple myeloma
Waldenström's macroglobulinemia
Heavy chain disease
Polycythemia vera In one embodiment, the cancer is pancreatic cancer, colorectal cancer, mesothelioma, a malignant pleural effusion, peritoneal carcinomatosis, peritoneal sarcomatosis, renal cell carcinoma, small cell lung cancer, non-small cell lung cancer, testicular cancer, bladder cancer, breast cancer, head and neck cancer, or ovarian cancer.

In still another embodiment, the subject in need of treatment has previously undergone treatment for cancer. Such previous treatments include, but are not limited to, prior chemotherapy, radiation therapy, surgery or immunotherapy, such as cancer vaccines.

The Tetracyclic Benzamide Derivatives are also useful for the treatment or prevention of a cancer caused by a virus. For example, human papilloma virus can lead to cervical cancer (see, e.g., Hemandez-Avila et al., Archives of Medical Research (1997) 28:265–271), Epstein-Barr virus (EBV) can lead to lymphoma (see, e.g., Herrmann et al., J Pathol (2003) 199(2):140–5), hepatitis B or C virus can lead to liver carcinoma (see, e.g., El-Serag, J Clin Gastroenterol (2002) 35(5 Suppl 2):S72–8), human T cell leukemia virus (HTLV)-I can lead to T-cell leukemia (see e.g., Mortreux et al., Leukemia (2003) 17(1):26–38), human herpesvirus-8 infection can lead to Kaposi's sarcoma (see, e.g., Kadow et al., Curr Opin Investig Drugs (2002) 3(11):1574–9), and Human Immune deficiency Virus (HIV) infection contribute to cancer development as a consequence of immunodeficiency (see, e.g., Dal Maso et al., Lancet Oncol (2003) 4(2):110–9).

4.17.1.1 Prophylactic Methods

The Tetracyclic Benzamide Derivatives of the Invention can also be administered to prevent the progression of a cancer, including but not limited to the cancers listed in Table 1. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68–79). Hyperplasia is a form of controlled cell proliferation involving an increase in cell number in a tissue or organ, without significant alteration in structure or function. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of the composition of the invention. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy can be treated by administration of an amount of a Tetracyclic Benzamide Derivative which is effective to treat or prevent cancer: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W. B. Saunders Co., Philadelphia, pp. 112–113) etc.), and exposure to carcinogens (e.g., smoking, and inhalation of or contacting with certain chemicals).

In another specific embodiment, the Tetracyclic Benzamide Derivatives are administered to a human patient to prevent progression to breast, colon, ovarian, or cervical cancer.

4.17.2 Therapeutic/Prophylactic Administration and Compositions of the Invention Due to their activity, the Tetracyclic Benzamide Derivatives are advantageously useful in veterinary and human medicine. As described above, the Tetracyclic Benzamide Derivatives are useful for treating or preventing a Condition in a subject in need thereof.

When administered to a subject, the Tetracyclic Benzamide Derivatives can be administered as a component of a composition that comprises a pharmaceutically acceptable carrier or vehicle. The present compositions, which comprise a Tetracyclic Benzamide Derivative, can be administered orally. The Tetracyclic Benzamide Derivatives of the invention can also be administered by any other convenient route, for example, by infusion or bolus injection, by absorption through epithelial or mucocutaneous linings (e.g., oral, rectal, and intestinal mucosa, etc.) and can be administered together with another biologically active agent. Administration can be systemic or local. Various delivery systems are known, e.g., encapsulation in liposomes, microparticles, microcapsules, capsules, etc., and can be administered.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration will result in the release of the Tetracyclic Benzamide Derivatives into the bloodstream. The mode of administration is left to the discretion of the practitioner.

In one embodiment, the Tetracyclic Benzamide Derivatives are administered orally.

In other embodiments, it can be desirable to administer the Tetracyclic Benzamide Derivatives locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Tetracyclic Benzamide Derivatives into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler of nebulizer, and Formulation with an aerosolizing agent, or via perfusion in a fluorocarbon oar, synthetic pulmonary surfactant. In certain embodiments, the Tetracyclic Benzamide Derivatives can be Formulated as a suppository, with traditional binders and excipients such as triglycerides.

In another embodiment the Tetracyclic Benzamide Derivatives can be delivered in a vesicle, in particular a liposome (see Langer, Science 249:1527–1533 (1990) and Treat or prevent et al., *Liposomes in the Therapy of Infectious Disease and Cancer* 317–327 and 353–365 (1989)).

In yet another embodiment the Tetracyclic Benzamide Derivatives can be delivered in a controlled-release system or sustained-release system (see, e.g., Goodson, in Medical Applications of Controlled Release, supra, vol. 2, pp. 115–138 (1984)). Other controlled or sustained-release systems discussed in the review by Langer, Science 249: 1527–1533 (1990) can be used. In one embodiment a pump can be used (Langer, Science 249:1527–1533 (1990); Sefton, CRC Crit. Ref Biomed. Eng. 14:201 (1987); Buchwald et al., Surgery 88:507 (1980); and Saudek et al., N. Engl. J Med. 321:574 (1989)). In another embodiment polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, J. Macromol. Sci. Rev. Macromol. Chem. 2:61 (1983); Levy et al., Science 228:190 (1935); During et al., Ann. Neural. 25:351 (1989); and Howard et al., J. Neurosurg. 71:105 (1989)).

In yet another embodiment. a controlled- or sustained-release system can be placed in proximity of a target of the Tetracyclic Benzamide Derivatives, e.g., the spinal column, brain, skin, lung, or gastrointestinal tract, thus requiring only a fraction of the systemic dose.

The present compositions can optionally comprise a suitable amount of a pharmaceutically acceptable excipient so as to provide the form for proper administration to the animal.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia; gelatin, starch paste, talc, keratin, colloidal silica, urea and the like. In addition, auxiliary, stabilizing, thickening, lubricating, and coloring agents can be used. In one embodiment the pharmaceutically acceptable excipients are sterile when administered to a subject. Water is a particularly useful excipient when the Tetracyclic Benzamide Derivative is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills; pellets, capsules, capsules containing liquids, powders, sustained-release Formulations, suppositories, emulsions. aerosols, sprays, suspensions, or any other form suitable for use. In one embodiment the composition is in the form of a capsule (see e.g. U.S. Pat. No. 5,698,155). Other examples of suitable pharmaceutical excipients are described in *Remington's Pharmaceutical Sciences* 1447–1676 (Alfonso R. Gennaro eds., 19th ed. 1995), incorporated herein by reference.

In one embodiment the Tetracyclic Benzamide Derivatives are Formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving a Tetracyclic Benzamide Derivativere also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release Formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In another embodiment the Tetracyclic Benzamide Derivatives can be Formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaien to lessen pain at the site of the injection. Generally, the ingredients are supplied either separately or mixed together in unit dosage form, for example, as a dry lyophilized-powder or water free concentrate in a hermetically sealed container such as an ampule or sachette indicating the quantity of active agent. Where the Tetracyclic Benzamide Derivatives are to be administered by infusion, they can be dispensed, for example, with an infusion bottle containing sterile pharmaceutical grade water or saline. Where the Tetracyclic Benzamide Derivatives are administered by injection, an ampule of sterile water for injection or saline can be provided so that the ingredient can be mixed prior to administration.

The Tetracyclic Benzamide Derivatives can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354;556; and 5,733,556, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release Formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained counterparts. In one embodiment a controlled- or sustained-release composition comprises a minimal amount of a Tetracyclic Benzamide Derivative to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Tetracyclic Benzamide Derivative, and can thus reduce the occurrence of adverse side effects.

Controlled- or sustained-release compositions can initially release an amount of a Tetracyclic Benzamide Derivative that promptly produces the desired therapeutic or prophylactic effect, and gradually and continually release other amounts of the Tetracyclic Benzamide Derivative to maintain this level of therapeutic or prophylactic effect over an extended period of time. To maintain a constant level of the Tetracyclic Benzamide Derivative in the body, the Tetracyclic Benzamide Derivative can be released from the dosage form at a rate that will replace the amount of Tetracyclic Benzamide Derivative being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Tetracyclic Benzamide Derivative that is effective in the treatment or prevention of a Condition can be determined by standard clinical techniques. In addition, in vitro or in vivo assays can optionally be employed to help identify optimal dosage ranges. The precise dose to be employed will also depend on the route of administration, and the seriousness of the condition being treated and should be decided according to the judgment of the practitioner and each patient's circumstances in view of, e.g., published clinical studies. Effective dosage amounts of the present invention, when used for the indicated effects, range from about 0.05 to about 1000 mg of Tetracyclic Benzamide Derivative per day. Compositions for in vivo or in vitro use can contain about 0.5, 1.0, 2.5, 5.0, 10.0, 15.0, 25.0, 50.0, 100.0, 250.0, 500.0 or 1000.0 mg of Tetracyclic Benzamide Derivative. In one embodiment, the compositions are in the form of a tablet that can be scored. Effective plasma levels of the Tetracyclic Benzamide Derivatives can range from about 0.002 mg to about 50 mg per kg of body weight per day.

Tetracyclic Benzamide Derivatives can be administered in a single daily dose, or the total daily dosage can be administered in divided doses of two, three or four times daily. Furthermore, Tetracyclic Benzamide Derivatives can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of Tetracyclic Benzamide Derivative ranges from about 0.1% to about 15%, w/w or w/v.

The Tetracyclic Benzamide Derivatives can be assayed in vitro or in vivo for the desired therapeutic or prophylactic activity prior to use in humans. Animal model systems can be used to demonstrate safety and efficacy.

The present methods for treating or preventing a Condition in a subject in need thereof can further comprise administering another therapeutic agent to the subject being administered a Tetracyclic Benzamide Derivative. In one embodiment the other therapeutic agent is administered in an effective amount.

Effective amounts of the other therapeutic agents are well known to those skilled in the art. However, it is well within the skilled artisan's purview to determine the other therapeutic agent's optimal effective amount range. In one embodiment of the invention, where, another therapeutic agent is administered to a subject, the effective amount of the Tetracyclic Benzamide Derivative is less than its effective amount would be where the other therapeutic agent is not administered. In this case, without being bound by theory, it is believed that the Tetracyclic Benzamide Derivatives and the other therapeutic agent act synergistically to treat or prevent a Condition.

In one embodiment the other therapeutice agent is an anti-inflammatory agent. Anti-inflammatory agents include but are not limited to adrenocorticosteroids, such as cortisol, cortisone, fludrocortisone, prednisone, prednisolone, 6a-methylprednisolone, triamcinolone, betamethasone, and dexamethasone; and non-steroidal anti-inflammatory agents (NSAIDs), such as aspirin, acetaminophen, indomethacin, sulindac, tolmetin, diclofenac, ketorolac, ibuprofen, naproxen, flurbiprofen, ketoprofen, fenoprofen, oxaprozin, mefenamic acid, meclofenamic acid, piroxicam, meloxicam, nabumetone, rofecoxib, celecoxib, etodolac, and nimesulide.

In one embodiment the other therapeutice agent is an anti-renal failure agent. Anti-renal failure agents include but are not limited to ACE (angiotensin-converting enzyme) inhibitors, such as captopril, enalaprilat, lisinopril, benazepril, fosinopril, trandolapril, quinapril, and ramipril; diuretics, such as mannitol, glycerin, furosemide, toresemide, tripamide, chlorothiazide, methyclothiazide, indapamide, amiloride, and spironolactone; and fibric acid agents, such as clofibrate, gemfibrozil, fenofibrate, ciprofibrate, and bezafibrate.

In one embodiment the other therapeutice agent is an anti-diabetic agent. Anti-diabetic agents include but are not limited to glucagons; somatostatin; diazoxide; sulfonylureas, such as tolbutamide, acetohexamide, tolazamide, chloropropamide, glybenclamide, glipizide, gliclazide, and glimepiride; insulin secretagogues, such as repaglinide, and nateglinide; biguanides, such as metformin and phenformin; thiazolidinediones, such as pioglitazone, rosiglitazone, and troglitazone; and α-glucosidase inhibitors, such as acarbose and miglitol.

In one embodiment the other therapeutic agent is an anti-cardiovascular disease agent. Anti-cardiovascular disease agents include but are not limited to camitine; thiamine; and muscarinic receptor antagonists, such as atropine, scopolamine, homatropine, tropicamide, pirenzipine, ipratropium, tiotropium, and tolterodine.

The other therapeutic agent can also be an agent useful for reducing any potential side effects of a Tetracyclic Benzamide Derivatives. For example, the other therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and mixtures thereof.

The present methods for the treatment or prevention of cancer can further comprise administering another anticancer agent. In one embodiment, the methods comprise the sequential administration of a Tetracyclic Benzamide Derivative and another anticancer agent. In another embodiment, the methods comprise the administration of a composition comprising a pharmaceutically acceptable carrier, a Tetracyclic Benzamide Derivative, and another anticancer agent.

The Tetracyclic Benzamide Derivative and the other anticancer agent can act additively or synergistically. A synergistic use of a Tetracyclic Benzamide Derivative and another anticancer agent permits the use of lower dosages of one or more of these agents and/or less frequent administration of said agents to a subject with cancer. The ability to utilize lower dosages of a Tetracyclic Benzamide Derivative and/or additional anticancer agents and/or to administer said agents less frequently can reduce the toxicity associated with the administration of said agents to a subject without reducing the efficacy of said agents in the treatment of cancer. In addition, a synergistic effect can result in the improved efficacy of these agents in the treatment of cancer and/or the reduction of adverse or unwanted side-effects associated with the use of either agent alone.

In one embodiment, the Tetracyclic Benzamide Derivative and the anticancer agent can act synergistically when administered in doses typically employed when such agents are used as monotherapy for the treatment of cancer. In another embodiment, the Tetracyclic Benzamide Derivative and the anticancer agent can act synergistically when administered in doses that are less than doses typically employed when such agents are used as monotherapy for the treatment of cancer.

Suitable additional anticancer agents useful in the methods and compositions of the present invention include, but are not limited to, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, taxanes such as docetaxel and paclitaxel, leucovorin, levamisole, irinotecan, estramustine, etoposide, nitrogen mustards, BCNU, nitrosoureas such as cannustine and lomustine, vinca alkaloids such as vinblastine, vincristine and vinorelbine, platinum complexes such as cisplatin, carboplatin and oxaliplatin, imatinib mesylate, hexamethylmelamine, topotecan, tyrosine kinase inhibitors, tyrphostins herbimycin A, genistein, erbstatin, and lavendustin A.

In one embodiment, the additional anticancer agent can be, but is not limited to, a drug listed in Table 2.

TABLE 2

| Alkylating agents | |
| --- | --- |
| Nitrogen mustards: | Cyclophosphamide |
| | Ifosfamide |
| | Trofosfamide |
| | Chlorambucil |
| Nitrosoureas: | Carmustine (BCNU) |
| | Lomustine (CCNU) |
| Alkylsulphonates: | Busulfan |
| | Treosulfan |
| Triazenes: | Dacarbazine |
| Platinum containing complexes: | Cisplatin |
| | Carboplatin |
| | Aroplatin |
| | Oxaliplatin |
| Plant Alkaloids | |
| Vinca alkaloids: | Vincristine |
| | Vinblastine |
| | Vindesine |
| | Vinorelbine |
| Taxoids: | Paclitaxel |
| | Docetaxel |
| DNA Topoisomerase Inhibitors | |
| Epipodophyllins: | Etoposide |
| | Teniposide |
| | Topotecan |
| | 9-aminocamptothecin |
| | Camptothecin |
| | Crisnatol |
| Mitomycins: | Mitomycin C |
| | Anti-metabolites |
| Anti-folates: | |
| DHFR inhibitors: | Methotrexate |
| | Trimetrexate |
| IMP dehydrogenase Inhibitors: | Mycophenolic acid |
| | Tiazofurin |
| | Ribavirin |
| | EICAR |
| Ribonucleotide reductase Inhibitors: | Hydroxyurea |
| | Deferoxamine |

TABLE 2-continued

| Pyrimidine analogs: | |
| --- | --- |
| Uracil analogs: | 5-Fluorouracil |
| | Fluoxuridine |
| | Doxifluridine |
| | Ralitrexed |
| Cytosine analogs: | Cytarabine (ara C) |
| | Cytosine arabinoside |
| | Fludarabine |
| | Gemcitabine |
| | Capecitabine |
| Purine analogs: | Mercaptopurine |
| | Thioguanine |
| DNA Antimetabolites: | 3-HP |
| | 2'-deoxy-5-fluorouridine |
| | 5-HP |
| | alpha-TGDR |
| | aphidicolin glycinate |
| | ara-C |
| | 5-aza-2'-deoxycytidine |
| | beta-TGDR |
| | cyclocytidine |
| | guanazole |
| | inosine glycodialdehyde |
| | macebecin II |
| | Pyrazoloimidazole |
| Hormonal therapies: | |
| Receptor antagonists: | |
| Anti-estrogen: | Tamoxifen |
| | Raloxifene |
| | Megestrol |
| LHRH agonists: | Goserelin |
| | Leuprolide acetate |
| Anti-androgens: | Flutamide |
| | Bicalutamide |
| Retinoids/Deltoids | |
| | Cis-retinoic acid |
| Vitamin A derivative: | All-trans retinoic acid (ATRA-IV) |
| Vitamin D3 analogs: | EB 1089 |
| | CB 1093 |
| | KH 1060 |
| Photodynamic therapies: | Vertoporfin (BPD-MA) |
| | Phthalocyanine |
| | Photosensitizer Pc4 |
| | Demethoxy-hypocrellin A (2BA-2-DMHA) |
| Cytokines: | Interferon-α |
| | Interferon-β |
| | Interferon-γ |
| | Tumor necrosis factor |
| Angiogenesis Inhibitors: | Angiostatin (plasminogen fragment) |
| | antiangiogenic antithrombin III |
| | Angiozyme |
| | ABT-627 |
| | Bay 12-9566 |
| | Benefin |
| | Bevacizumab |
| | BMS-275291 |
| | cartilage-derived inhibitor (CDI) |
| | CAI |
| | CD59 complement fragment |
| | CEP-7055 |
| | Col 3 |
| | Combretastatin A-4 |
| | Endostatin (collagen XVIII fragment) |
| | Fibronectin fragment |
| | Gro-beta |
| | Halofuginone |
| | Heparinases |
| | Heparin hexasaccharide fragment |
| | HMV833 |
| | Human chorionic gonadotropin (hCG) |
| | IM-862 |
| | Interferon alpha/beta/gamma |

TABLE 2-continued

| | |
|---|---|
| | Interferon inducible protein (IP-10) |
| | Interleukin-12 |
| | Kringle 5 (plasminogen fragment) |
| | Marimastat |
| | Metalloproteinase inhibitors (TIMPs) |
| | 2-Methoxyestradiol |
| | MMI 270 (CGS 27023A) |
| | MoAb IMC-1C11 |
| | Neovastat |
| | NM-3 |
| | Panzem |
| | PI-88 |
| | Placental ribonuclease inhibitor |
| | Plasminogen activator inhibitor |
| | Platelet factor-4 (PF4) |
| | Prinomastat |
| | Prolactin 16 kD fragment |
| | Proliferin-related protein (PRP) |
| | PTK 787/ZK 222594 |
| | Retinoids |
| | Solimastat |
| | Squalamine |
| | SS 3304 |
| | SU 5416 |
| | SU6668 |
| | SU11248 |
| | Tetrahydrocortisol-S |
| | Tetrathiomolybdate |
| | Thalidomide |
| | Thrombospondin-1 (TSP-1) |
| | TNP-470 |
| | Transforming growth factor-beta (TGF-b) |
| | Vasculostatin |
| | Vasostatin (calreticulin fragment) |
| | ZD6126 |
| | ZD 6474 |
| | farnesyl transferase inhibitors (FTI) |
| | Bisphosphonates |
| Antimitotic agents: | Allocolchicine |
| | Halichondrin B |
| | Colchicine |
| | colchicine derivative |
| | dolstatin 10 |
| | Maytansine |
| | Rhizoxin |
| | Thiocolchicine |
| | trityl cysteine |
| Others: | |
| Isoprenylation inhibitors: | |
| Dopaminergic neurotoxins: | 1-methyl-4-phenylpyridinium ion |
| Cell cycle inhibitors: | Staurosporine |
| Actinomycins: | Actinomycin D |
| | Dactinomycin |
| Bleomycins: | Bleomycin A2 |
| | Bleomycin B2 |
| | Peplomycin |
| Anthracyclines: | Daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | Verapamil |
| $Ca^{2+}$ ATPase inhibitors: | Thapsigargin |

Other additional anticancer agents that can be used in the compositions and methods of the present invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin: doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine hydrochloride; hydroxyurea; idarubicin hydrochloride; ifosfamide; ilmofosine; interleukin II (including recombinant interleukin II, or rIL2), interferon alfa-2α; interferon alfa-2β; interferon alfa-n1; interferon alfa-n3; interferon beta-Iα; interferon gamma-Iβ; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Further anticancer drugs that can be used in the methods and compositions of the invention include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amnifostine; aminolevulinic acid; amrubicin; amsacrine; anagrelide; anastrozole; andrapholide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3;

azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-acytidine; dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agents; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; sarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

4.17.1.3 Multi-Modality Therapy for Cancer

The Tetracyclic Benzamide Derivatives can be administered to a subject that has undergone or is currently undergoing one or more additional anticancer treatment modalities including, but not limited to, surgery, radiation therapy, or immunotherapy, such as cancer vaccines.

In one embodiment, the invention provides methods for treating cancer comprising (a) administering to a subject in need thereof an amount of a Tetracyclic Benzamide Derivative effective to treat or prevent cancer; and (b) administering to said subject one or more additional anticancer treatment modalities including, but not limited to, surgery, radiation therapy, or immunotherapy, such as a cancer vaccine.

In one embodiment, the additional anticancer treatment modality is radiation therapy.

In another embodiment, the additional anticancer treatment modality is surgery.

In still another embodiment, the additional anticancer treatment modality is immunotherapy.

In a specific embodiment, the Tetracyclic Benzamide Derivatives are administered concurrently with radiation therapy. In another specific embodiment, the additional anticancer treatment modality is administered prior or subsequent to the Tetracyclic Benzamide Derivative, preferably at least an hour, five hours, 12 hours, a day a week, a month, more preferably several months (e.g., up to three months), prior or subsequent to administration of the Tetracyclic Benzamide Derivatives.

When the additional anticancer treatment modality is radiation therapy, any radiation therapy protocol can be used depending upon the type of cancer to be treated. For example, but not by way of limitation, X-ray radiation can be administered; in particular, high-energy megavoltage (radiation of greater that 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered.

Additionally, the invention provides methods of treatment of cancer using the Tetracyclic Benzamide Derivatives as an alternative to chemotherapy or radiation therapy where the chemotherapy or the radiation therapy results in negative side effects, in the subject being treated. The subject being treated can, optionally, be treated with another anticancer treatment modality such as surgery, radiation therapy, or immunotherapy, depending on which treatment is found to be acceptable or bearable.

The Tetracyclic Benzamide Derivatives can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the patient's remaining bone-marrow cell population is then eradicated via the administration of high doses of the Tetracyclic Benzamide Derivatives and/or high dose radiation therapy, and the stem cell graft is infused back into the animal. Supportive care is then provided while bone marrow function is restored and the subject recovers.

A Tetracyclic Benzamide Derivative and the other therapeutic agent can act additively or, in one embodiment synergistically. In one embodiment a Tetracyclic Benzamide Derivative is administered concurrently with another therapeutic agent. In one embodiment a composition comprising an effective amount of a Tetracyclic Benzamide Derivative and an effective amount of another therapeutic agent can be administered. Alternatively, a composition comprising an effective amount of a Tetracyclic Benzamide Derivative and a different composition comprising an effective amount of another therapeutic agent can be concurrently administered. In another embodiment an, effective amount of a Tetracyclic Benzamide Derivative is administered prior or subsequent to administration of an effective amount of another therapeutic agent. In this embodiment the Tetracyclic Benzamide Derivative is administered while the other therapeutic agent exerts its therapeutic effect, or the other therapeutic agent is administered while the Tetracyclic Benzamide Derivative exerts its preventative or therapeutic effect for treating or preventing a Condition.

A composition of the invention is prepared by a method comprising admixing a Tetracyclic Benzamide Derivative or a pharmaceutically acceptable salt and a pharmaceutically acceptable carrier or vehicle. Admixing can be accomplished using methods well known for admixing a compound (or salt) and a pharmaceutically acceptable carrier or vehicle. In one embodiment the Tetracyclic Benzamide Derivative or the pharmaceutically acceptable salt of the Compound is present in the composition in an effective amount.

4.17.3 Kits

The invention encompasses kits that can simplify the administration of a Tetracyclic Benzamide Derivative to a subject.

A typical kit of the invention comprises a unit dosage form of a Tetracyclic Benzamide Derivative. In one embodiment the unit dosage form is a container, which can be sterile, containing an effective amount of a Tetracyclic Benzamide Derivative and a pharmaceutically acceptable carrier or vehicle. The kit can further comprise a label or printed instructions instructing the use of the Tetracyclic Benzamide Derivative to treat or prevent a Condition. The kit can also further comprise a unit dosage form of another therapeutic agent, for example, a container containing an effective amount of the other therapeutic agent. In one embodiment the kit comprises a container containing an effective amount of a Tetracyclic Benzamide Derivative and an effective amount of another therapeutic agent. Examples of other therapeutic agents include, but are not limited to, those listed above.

Kits of the invention can further comprise a device that is useful for administering the unit dosage forms. Examples of such a device includes, but are not limited to, a syringe, a drip bag, a patch, an inhaler, and an enema bag.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in Formulation or minor changes in experimental design, are to be considered to fall within the scope of the invention incorporated herein.

5. EXAMPLES 5.1.1 Example 1

Preparation of Illustrative Tetracyclic Benzamide Derivatives 5.1.2 General Methods Proton NMR spectra were obtained using a Varian 300 MHz spectrophotometer and chemical shift values ($\delta$) are reported in parts per million (ppm). TLC was performed using TLC plates precoated with silica gel 60 F-254, and preparative TLC was performed using precoated Whatman 60A TLC plates. All intermediates and final compounds were characterized on the basis of $^1$H NMR and MS data.

a) Preparation of 4-Phenyl-3-isocoumarincarboxylic acid (3a):

Following the procedure described in Natsugary et al., *J. Med. Chem.* 38, 3106–3120 (1995), compound 3a (Scheme 1) was synthesized. A suspension of 1a (33.9 g, 0.15 mol) (Scheme 1), potassium carbonate (41.4 g, 0.3 mol) and diethyl bromomalonate (28.17 mL, 0.165 mol) in DMF (250 mL) was stirred at room temperature for 15 h. The reaction mixture was then diluted using cold water and extracted into ethyl acetate. The ethyl acetate layer was dried over sodium sulfate, and concentrated in vacuo to afford a crude residue to which was added glacial acetic acid (1.0 L) and concentrated HCl (800 mL). The resulting solution was heated at reflux for 6 h. The reaction mixture was cooled to room temperature and poured on ice water. The solid precipitate was filtered, washed with water and dried using vacuum to provide compound 3a as a white solid. Yield=32.6 g (84%).

b) Preparation of 4-Phenyl-3-isoquinolinonecarboxylic acid (4a)(Scheme 1):

A stirred suspension of 3a (1.4 g, 0.0052 mol) in ammonia-methanol (7 N, 125 mL) was heated at reflux for 23 h, then cooled to room temperature. The reaction mixture was concentrated in vacuo, and the residue obtained was acidified with 10% aqueous HCl. The resulting solid was filtered, washed with water and dried under vacuum to provide compound 4a. Yield=1.225 g (89%).

c) Preparation of 6H, 7-oxoindeno[2,1-c]isoquinolinone (5a) (Scheme 1):

Using PPA:

To a stirred suspension of compound 4a (0.225 g, 0.85 mmol) in xylenes (20 mL) was added polyphosphoric acid (0.600 g). The resulting reaction mixture was heated at reflux for 6 h. The reaction mixture was cooled to room temperature and concentrated in vacuo to provide a crude residue, which was poured on ice. The resulting solid was filtered, washed with water, and dried under vacuum to provide compound 5a. Yield=155 mg (74%).

Using Chlorosulfonic Acid:

Similarly, compound 4a (500 mg, 0.0019 mol) was suspended up in chlorosulfonic acid (2.5 mL) at 0° C. for 5 min, and the reaction mixture was stirred at room temperature for 5 min. After the reaction mixture became homogeneous, it was slowly poured on ice. The resultant red-colored solid precipitate was filtered, washed with water, and dried to provide compound 5a. Yield=395 mg (85%).

d) Reduction of (5a) to 6H,7H-Hydroxyindeno[2,1-c]isoquinolin-5-one (6a) (Compounds of Formula IIa) (Scheme 1):

To a stirred suspension of 5a (1.0 g, 4.0 mmol) in methanol (25 mL) was slowly added solid sodium borohydride (385 mg) at room temperature. The resulting reaction mixture was stirred for 15 min. The reaction mixture was then poured on an ice-cold 1 N HCl solution, and the resulting solid was filtered, washed with water, and dried under vacuum to provide compound 6a (Formula IIa). Yield=0.940 g (93%).

e) Preparation of 5-Oxo-5,7-dihydro-6H-indeno[2,1-C]isoquinoline-9-sulfonyl chloride (10a) (Scheme 1):

Compound 9a (210 mg, 0.9 mmol) was slowly added to a solution of chlorosulphonic acid (2.0 mL) at 0° C. for 5 min, and at room temperature for 5 min. After the reaction mixture became homogeneous, it was slowly poured on ice. The solid that precipitated was filtered, washed with water, and dried to provide compound 10a (180 mg, 60%).

f) 5-Oxo-5,7-dihydro-6H-indeno[2,1-c]isoquinoline-9-sulfonic acid (3-morpholin-4-yl-propyl)-amide (11a) (Scheme 1):

A suspension of 10a (110 mg, 0.33 mmol) in methylene chloride (10 mL) was treated with 4-(3-morpholino)-1-propylamine (240 mg, 1.66 mmol) and triethylamine (1 eq), and the reaction mixture was stirred at room temperature for 1 h. The resulting mixture was diluted with ethyl acetate, and the solid that precipitated was filtered, washed with ether and dried to provide compound 11a. Yield=65 mg (45%).

g) Preparation of 2-(bromo-methoxycarbonyl-methyl)-benzoic acid methyl ester (α-Bromodimethylhomophthalate) (13a) (Scheme 2):

Dimethylhomophthalate (83.1 g, Aldrich Chemical Co.) was dissolved in dichloromethane (2 L), and N-bromosuccinimide (121 g, 1.7 eq) was added. The resulting suspension was irradiated for 18 h with a 500 wt quartz-halogen lamp, which brought the reaction mixture to reflux. The reaction mixture was then washed sequentially with saturated aqueous sodium bicarbonate (4 L), saturated aqueous sodium bisulfite (2 L), and saturated aqueous sodium chloride (2 L). The organic phase was dried using sodium sulfate with a small amount of silica added to remove polar impurities. The organic phase was filtered and concentrated in vacuo to provide compound 13a (Scheme 2) as a dark orange oil. Yield 120.3 g (100%).

h) Preparation of 8-Methoxy-6H-11-oxa-6-aza-benzo[a]fluoren-5-one (15a) (Scheme 2):

A mixture of α-Bromodimethylhomophthalate (13a) (1.16 g) and 2-hydroxy-5-methoxy-benzonitrile (14b), 0.6 g, 4 mmol, 1.0 eq) was dissolved by wanning in acetonitrile (6 mL). Triethylamine (5.6 mL, 10 eq) was then added. The reaction mixture was heated at reflux for 48 h under inert atmosphere, then cooled to room temperature. The reaction mixture was diluted with saturated sodium bicarbonate (40 mL), and the resulting suspension was allowed to stir for 2 h, and was then filtered. The resulting filtercake was washed sequentially with 1 N HCl (2×50 mL), acetonitrile (2×50 mL) and dichloromethane (50 mL), then dried in a vacuum oven at 50° C. fot three days to provide compound 15a as an white solid. Yield=0.81 mg (76%).

i) Preparation of 8-Hydroxy-6H-11-oxa-6-aza-benzo[a]lfluoren-5-one (15b) (Scheme 2):

8-Methoxy-6H-11-oxa-6-aza-benzo[a]fluoren-5-one (15a) (5.0 g) was cooled using an ice bath, and boron tribromide (1 M in methylene chloride, 95 mL, 95 mmol, 5 eq) was added in a steady stream under nitrogen. The reaction was heated at reflux under inert atmosphere for 2 h, then cooled to room temperature and poured into water (150 mL). The resulting suspension was allowed to stir for 1 h, filtered, and the solids were washed with water (2×200 mL). The solids were then suspended in of 5 N sodium hydroxide (600 mL), then using heating. The resulting solution was cooled to 0° C. using an ice bath and the solution acidified to pH 1 using con c. HCl. The resulting precipitate was vacuum filtered, and the solids were washed sequentially with water (3×300 mL), and diethyl ether (300 mL), then dried overnight using a vacuum oven at 50° C. to provide compound 15b as a gray solid. Yield=4.74 g (100%).

j) Preparation of 6H-11-oxa-6-aza-benzo[a]fluoren-5-one (15c):

Using the method of Example h and substituting 14b with 2-hydroxy-benzonitrile (14a), compound 15c was prepared.

k) Preparation of 9-Methoxy-6H-11-oxa-6-aza-benzo[a]fluoren-5-one (15d):

Using the method of Example h and substituting 14b with 2-hydroxy-4-methoxy-benzonitrile (14c), compound 15d was prepared.

l) Preparation of 9-Hydroxy-6H-11-oxa-6-aza-benzo[a]fluoren-5-one (15e):

Using the method of Example i and substituting compound 15a with compound 15d, compound 15e was prepared.

m) Preparation of Compound 16a (Scheme 2):

To a solution of compound 15b (0.755 mmol) in acetone (4 mL) was added 2-bromoacetic acid (2.1 eq) and potassium carbonate (1.04 g, 10 eq). The resultant mixture was heated at reflux for 15 h under nitrogen atmosphere. The reaction mixture was poured into 20 mL of 1 N aqueous sodium hydroxide, stirred 0.5 h, and filtered. The solids were washed twice with 10 mL volumes of water, then stirred for 1 h in 20 mL of 1 N aqueous hydrochloric acid. The solids were vacuum filtered, washed twice with 10 mL of water, twice with 10 mL of ether, and dried in vacuo to provide compound 16a in 75% yield.

n) Preparation of Compound 16b:

Using the method of Example m and substituting 2-bromoacetic acid with 3-bromo-1-propanol, compound 16b was prepared from compound 15b.

o) Preparation of Compound 16c:

Using the method of Example m and substituting 2-bromoacetic acid with 5-bromo-1-pentanol, compound 16c was prepared from compound 15b.

p) Preparation of Compound 16d:

Using the method of Example m and substituting 2-bromoacetic acid with 6-bromo-1-hexanol, compound 16d was prepared from compound 15b.

q) Preparation of Compound 16e:

Using the method of Example m and substituting 2-bromoacetic acid with 5-bromo-1-pentanoic acid, compound 16e was prepared from compound 15b.

r) Preparation of Compound 16f:

To a solution of compound 15c (0.755 mmol) in acetone (4 mL) was added iodomethane (52 µL, 1.1 eq) and potassium carbonate (1.04 g, 10 eq). The resultant mixture was heated at reflux for 15 h under nitrogen atmosphere. The reaction mixture was poured into 20 mL of 1 N aqueous sodium hydroxide, stirred 0.5 h, and filtered. The resultant solids were washed twice with 10 mL of water, then stirred for 1 h in 20 mL of 1 N aqueous hydrochloric acid. The resultant solids were vacuum filtered, washed twice with 10 mL of water, twice with 10 mL of ether, and dried in vacuo to provide 165 mg (78%) of compound 16f.

s) Preparation of Acetic acid 11-oxa-6-aza-benzo[a]fluoren-5-yl ester (16g):

To a solution of compound 15c (500 mg, 2.13 mmol) in pyridine (10 mL) was added acetic anhydride (4 mL). The resultant mixture was heated at 100° C. for 9 h, then cooled slowly to room temperature overnight. The solvent was removed on the rotary evaporator and the residual oil was extracted into 50 mL ethyl acetate. The organic layer was washed with 50 mL of 1 N aqueous hydrochloric acid, dried (sodium sulfate), and the solvent removed in vacuo to provide 308 mg (52% yield) of compound 16g as a white powder.

t) Preparation of 1-(11-Oxa-6-aza-benzo[a]fluoren-5-yloxy)-β-D-glucuronic acid (16h):

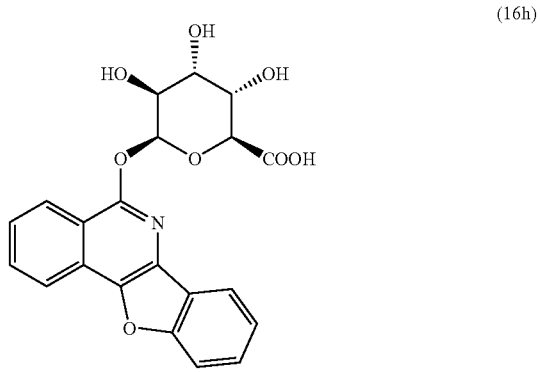

(16h)

Preparation of Methyl Ester Intermediate:

6H-11-Oxa-6-aza benzo[a]fluoren-5-one (15c) (500 mg, 2.13 mmol) (Scheme 2), silver carbonate (2.35 g, 4 eq), 4 angstrom molecular sieves (1.8 g), and 100 mL toluene were combined in a 500 mL 3-neck flask equipped with a dean-stark trap, a condenser, and an addition funnel. The mixture was brought to reflux under nitrogen atmosphere, and 30 mL of distillate were collected over 1 h. The addition funnel was charged with acetobromo-α-D-glucuronic acid methyl ester (930 mg, 1.1 eq) dissolved in 25 mL toluene, and this solution was added dropwise over 0.5 h to the refluxing reaction mixture. The reaction mixture was heated at reflux for another 6 h, then slowly cooled to room temperature overnight. The resulting suspension was vacuum filtered to remove solids, and the filter cake was washed three times with 100 mL of ethyl acetate. The filtrate was concentrated to an oil on the rotary evaporator. The oil was loaded directly on a column of 30 g silica and purified by flash chromatography, eluting with 19:1 dichloromethane: ethyl acetate to provide of the intermediate compound 1-(11-Oxa-6-aza-benzo[a]fluoren-5-yloxy)2,3,4-tri-O-acetyl-β-D-glucuronic acid methyl ester as a white powder.

Ester Hydrolysis to Provide Compound 16h:

1-(11-Oxa-6-aza-benzo[a]fluoren-5-yloxy)-2,3,4-tri-O-acetyl-β-D-glucuronic acid methyl ester (779 mg, 1.81 mmol) was dissolved in 30 mL acetone, and 8 mL of 1 N aqueous sodium hydroxide followed by 12 mL water were added dropwise. The resultant mixture was stirred for 0.5 h, over which time a precipitate formed. The reaction mixture was titrated to pH 5 with 1 N aqueous hydrochloric acid and vacuum filtered. The resultant solids were washed with 30 mL of acetone and dried in vacuo to give 288 mg (50%) of compound 16h as a white powder.

u) 5,9-Dimethoxy-11-oxa-6-aza-benzo[a]fluorine (16i):

9-Methoxy-6H-11-oxa-6-aza-benzo[a]fluorine-5-one (200 mg, 0.755 mmol) was suspended in 4 mL acetone and to the suspension were added. Methyl iodide (52 µL, 1.1 eq) and potassium carbonate (1.04 g, 10 eq). The mixture was allowed to reflux overnight under nitrogen atmosphere. Additional methyl iodide (25 µL, 0.5 eq) and acetone (4 mL) were added and the reaction refluxed overnight under nitrogen. The reaction mixture was poured into 20 mL of 1 N aqueous sodium hydroxide, stirred 0.5 h, and filtered. The resultant solids were washed twice with 10 mL of water, then stirred for 1 h in 20 mL of 1 N aqueous hydrochloric acid. The solids were vacuum filtered, washed twice with 10 mL of water, then twice with 10 mL volumes of ether. The solids were dried in vacuo to give 165 mg (78%) of compound 16i as a white powder.

v) Preparation of Compound 16j:

Using the method of Example m and substituting: 1) 2-bromoacetic acid with 3-bromo-1-propanol, and 2) compound 15b with compound 15c, compound 16j was prepared.

w) Preparation of Compound 16k

Using the method of Example m and substituting: 1) 2-bromoacetic acid with 6-bromo-1-hexanol, and 2) compound 15b with compound 15c, compound 16k was prepared.

x) Preparation of 9-Methyl-6H-11-oxa-6,10-diaza-benzo[a]fluoren-5-one (26a)

To a solution of α-bromodimethylhomophthalate (2.00 g, 6.97 mmol) in DMF (15 mL) was added 3-cyano-2-hydroxy-6-methylpyridine (1.03 g, 1.1 eq) and potassium carbonate (4.82 g, 5 eq). The resulting mixture was allowed to stir at 100° C. for 4 h under inert atmosphere. The reaction was cooled to room temperature and concentrated in vacuo. The resulting solid residue was diluted with 1 N aqueous HCl (60 mL) and stirred for 30 min. The resulting suspension was filtered and the solids were washed with water. The aqueous filtrate was extracted with EtOAc (2×50 mL). The collected solids were added to the combined EtOAc extracts, and the resulting solution was dried over sodium sulfate, filtered and concentrated in vacuo to afford a crude residue. The crude residue was recrystallized from toluene at −20° C. over 18 h, vacuum filtered and dried to provide compound 26a as a yellow solid. Yield=500 mg (29%).

5.1.3 Example 2

Effect of Illustrative Tetracyclic Benzamide Derivatives on PARP Activity in Cultured Macrophages, Using a Whole-Cell Based Assay and a Purified Enzyme Assay Demonstration of illustrative Tetracyclic Benzamide Derivatives' ability to inhibit PARP and prevent peroxynitrite induced cytotoxicity was shown using methods described in Virag et al., *Br. J. Pharmacol.*, 1999, 126(3): 769–77; and *Immunology* 1998, 94(3):345–55. RAW mouse macrophages were cultured in DMEM medium with high glucose and supplemented with 10% fetal bovine serum. Cells were used at 80% confluence in 12-well plates. Cells were pretreated with various concentrations (100 nM-1 μM) of a Tetracyclic Benzamide Derivative for 10 min. Peroxynitrite, a prototypical oxidant which induces DNA single strand breakage, was used to induce PARP activation. Peroxynitrite was diluted in phosphate buffered saline (PBS) (pH 11.0) and added to the cells in a bolus of 50 μl. Cells were then incubated for 20 min. Peroxynitrite was decomposed by incubation for 30 min at pH 7.0, used as a control, and failed to influence the parameter studied. After the 20 min incubation, the cells were spun, the medium was aspirated and the cells were resuspended in 0.5 mL assay buffer (56 mM HEPES pH 7.5, 28 mM KCl, 28 mM NaCl, 2 mM $MgCl_2$, 0.01% w/v digitonin and 0.125 μM $NAD^+$ and 0.5 μCi/ml $^3H$-$NAD^+$). Following an incubation in assay buffer, (10 min at 37° C.), PARP activity was measured as follows: 200 μl ice cold 50% w/v TCA was added and the samples were incubated for 4 h at 4° C. Samples were then spun (10 min @ 10,000 g) and pellets washed twice with ice cold 5% w/v TCA and solubilized overnight in 250 μl 2% w/v SDS/0.1 N NaOH at 37° C. The contents of the tubes were added to 6.5 mL ScintiSafe Plus scintillation liquid (Fisher Scientific) and radioactivity was determined using a liquid scintillation counter (Wallac, Gaithersburg, Md.). The results shown in Table 3 demonstrate that the illustrative Tetracyclic Benzamide Derivatives significantly and dose-dependently inhibit the activation of PARP in the macrophage assay.

TABLE 3

Inhibitory effect of various novel substituted Tetracyclic Benzamide Derivatives on PARP activation in cultured murine macrophages.

| Compound No. | % PARP inhibition at 1 μM | % PARP inhibition at 300 nM | % PARP inhibition at 100 nM |
|---|---|---|---|
| 9a | 70 | 56 | NT |
| 11 | 70 | 9 | NT |
| 16a | 56 | 64 | 47 |
| 16b | 29 | 26 | 25 |
| 16c | 68 | 47 | 39 |
| 16d | NT | 38 | 3 |
| 16e | 57 | 56 | 33 |
| 16f | 56 | 59 | 40 |
| 16g | 67 | 66 | 40 |
| 16h | NT | 56 | 32 |
| 26a | 61 | 54 | 36 |

NT—Not Tested

The potency of inhibition on purified PARP enzyme was subsequently determined for selected Tetracyclic Benzamide Derivatives, and the potency was compared with that of 3-aminobenzamide, a prototypical benchmark PARP inhibitor. The assay was performed in 96 well ELISA plates according to instructions provided with a commercially available PARP inhibition assay kit (Trevigen, Gaithersburg, Md.). Briefly, wells were coated with 1 mg/mL histone (50 μl/well) at 4° C. overnight. Plates were then washed four times with PBS and then blocked by adding 50 μl Strep-Diluent (supplied with the kit). After incubation (1 h, room temperature), the plates were washed four times with PBS. Appropriate dilutions of PARP inhibitors were combined with 2× PARP cocktail (1.95 mM $NAD^+$, 50 μM biotinylated $NAD^+$ in 50 mM TRIS pH 8.0, 25 mM $MgCl_2$) and high specific activity PARP enzyme (both were supplied with the kit) in a volume of 50 μl. The reaction was allowed to proceed for 30 min at room temperature. After 4 washes in PBS, incorporated biotin was detected by peroxidase-conjugated streptavidin (1:500 dilution) and TACS Sapphire substrate. The assay confirmed the results of the macrophage-based PARP assay. For example, the PARP inhibitor 16a exerted 56% inhibition of PARP activity in this assay at 1 μM, and thus was approximately 56,000 times more potent than the reference compound 3-aminobenzamide at this concentration. These results indicate that compounds 9a, 11, 16a–16h and 26a, illustrative Tetracyclic Benzamide Derivatives, are useful for treating or preventing a Condition.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which have been incorporated herein in their entirety.

What is claimed is:

1. A compound of the Formula

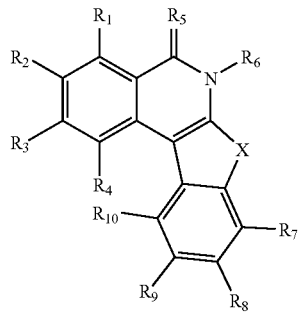

(II)

or a pharmaceutically acceptable salt or hydrate thereof, wherein:

$R_5$ is O, NH or S;

$R_6$ is —H or $C_1$–$C_4$ alkyl;

X is —C(O)—, —$CH_2$—, —CH(halo)-, —(C(OH)(($CH_2$)$_n$$CH_3$))—, —(C(OH)(aryl))- or —CH($NR_{11}R_{12}$)—, wherein n is an integer ranging from 0–5;

$R_{11}$ and $R_{12}$ are independently -hydrogen or —$C_1$–$C_9$ alkyl, or N, $R_{11}$ and $R_{12}$ are taken together to form a -(nitrogen-containing 3- to 7-membered monocyclic heterocycle), or a -(nitrogen-containing 7- to 10-membered bicyclic heterocycle);

$R_1$, $R_2$, $R_3$, $R_4$, $R_7$, $R_8$, $R_9$ and $R_{10}$ are independently -hydrogen, -halo, -hydroxy, —$C_1$–$C_{10}$ alkyl, halo-substituted-($C_1$–$C_5$ alkyl), —$C_2$–$C_{10}$ alkenyl, —$C_3$–$C_8$-cycloalkyl, -aryl, —$NH_2$, amino-substituted-($C_1$–$C_5$ alkyl), —C(O)OH, —C(O)O($C_1$–$C_5$ alkyl), —OC(O)($C_1$–$C_5$ alkyl), $NO_2$ or -A-B, wherein at least one of $R_1$, $R_2$, $R_3$, $R_4$, $R_7$, $R_8$, $R_9$ and $R_{10}$ is other than hydrogen;

A is —$SO_2$—, —$SO_2$NH—, —NHCO—, —NH-CONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -(nitrogen-containing 3- to 7-membered monocyclic heterocycle), -(nitrogen-containing 7- to 10-membered bicyclic heterocycle), -(3- to 7-membered monocyclic heterocycle), -(7- to 10-membered bicyclic heterocycle), —$C_3$–$C_8$ cycloalkyl, -aryl, —$NZ_1Z_2$, —($C_1$–$C_5$alkylene)-$NZ_1Z_2$, amino-substituted-($C_1$–$C_5$ alkyl), —N($C_1$–$C_5$ alkyl)($C_1$–$C_5$ alkyl), —($C_1$–$C_5$ alkyl)-(3- to 7-membered monocyclic heterocycle), or —($C_1$–$C_5$ alkyl)-(7- to 10-membered bicyclic heterocycle), —($H_2$NC(O))-substituted aryl, —($H_2$NC(O))-substituted pyridyl, —C(O)OH, —C(O)O—($C_1$–$C_5$ alkyl), —C(O)O-phenyl or —C(NH)$NH_2$, each of which is unsubstituted or substituted with one or more of —O—($C_1$–$C_5$ alkyl), -halo, halo-substituted-($C_1$–$C_5$ alkyl), HO-substituted-($C_1$–$C_5$ alkyl), amino-substituted-($C_1$–$C_5$ alkyl), -hydroxy, —$NO_2$, —$NH_2$, —CN, —NH($C_1$–$C_5$ alkyl), —N($C_1$–$C_5$ alkyl)($C_1$–$C_5$ alkyl), -(nitrogen-containing 3- to 7-membered monocyclic heterocycle), 7- to 10-membered bicycloheterocyclic amine, —$C_1$–$C_{10}$ alkyl, —$C_2$–$C_{10}$ alkenyl, —$C_2$–$C_{10}$ alkynyl, -aryl, -benzyl, —($H_2$NC(O))-substituted ($C_1$–$C_5$ alkyl), carboxy-substituted-($C_1$–$C_5$ alkyl), —C(O)OH, —$C_1$–$C_5$-alkylene-C(O)O—($C_1$–$C_5$ alkyl) or —$C_1$–$C_5$ alkylene-OC(O)—($C_1$–$C_5$ alkyl), such that -A-B is other than —O—($C_1$–$C_{10}$ alkyl); and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form a -(nitrogen-containing 3- to 7-membered monocyclic heterocycle) or a -(nitrogen-containing 7- to 10-membered bicyclic heterocycle); or N, $Z_1$ and $Z_2$ are taken together to form a -(nitrogen-containing 3- to 7-membered monocyclic heterocycle), or a -(nitrogen-containing 7- to 10-membered bicyclic heterocycle).

2. The compound or the pharmaceutically acceptable salt of the compound of claim 1, wherein X is —$CH_2$— and $R_5$ is —O—.

3. A composition comprising an effective amount of the compound or pharmaceutically acceptable salt or hydrate of the compound of claim 1 and a pharmaceutically acceptable carrier or vehicle.

4. A method for treating Parkinson's disease, comprising administering to a subject in need thereof a compound or a pharmaceutically acceptable salt or hydrate of a compound having the formula:

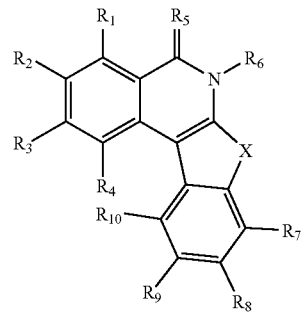

(II)

wherein:

$R_5$ is O, NH or S;

$R_6$ is —H or $C_1$–$C_4$ alkyl;

X is —C(O)—, —$CH_2$—, —CH(halo)-, —(C(OH)(($CH_2$)$_n$$CH_3$))—, —(C(OH)(aryl))-, or —CH($NR_{11}R_{12}$)— wherein n is an integer ranging from 0–5;

$R_{11}$ and $R_{12}$ are independently -hydrogen or —$C_1$–$C_9$ alkyl, or N, $R_{11}$ and $R_{12}$ are taken together to form a -(nitrogen-containing 3- to 7-membered monocyclic heterocycle), or a -(nitrogen-containing 7- to 10-membered bicyclic heterocycle);

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, halo-substituted-($C_1$–$C_5$ alkyl), —$C_2$–$C_{10}$ alkenyl, —$C_3$–$C_8$-cycloalkyl, -aryl, —$NH_2$, amino-substituted-($C_1$–$C_5$ alkyl), —C(O)OH, —C(O)O($C_1$–$C_5$ alkyl), —OC(O)($C_1$–$C_5$ alkyl), $NO_2$ or -A-B;

A is —$SO_2$—, —$SO_2$NH—, —NHCO—, —NH-CONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -(nitrogen-containing 3- to 7-membered monocyclic heterocycle),-(nitrogen-containing 7- to 10-membered bicyclic heterocycle), -(3- to 7-membered monocyclic heterocycle), -(7- to 10-membered bicyclic heterocycle), —$C_3$–$C_8$ cycloalkyl, -aryl, —$NZ_1Z_2$, —($C_1$–$C_5$ alkylene)-$NZ_1Z_2$, amino-substituted-($C_1$–$C_5$ alkyl), —N($C_1$–$C_5$ alkyl)($C_1$–$C_5$ alkyl), —($C_1$–$C_5$ alkyl)-(3- to 7-membered monocyclic heterocycle), or —($C_1$–$C_5$ alkyl)-(7- to 10-membered bicyclic heterocycle), —($H_2$NC(O))-substituted aryl, —($H_2$NC(O))-substituted pyridyl, —C(O)OH, —C(O)O—($C_1$–$C_5$ alkyl), —C(O)O-phenyl or —C(NH)$NH_2$, each of which is unsubstituted or substituted with one or more of —O— ($C_1$–$C_5$ alkyl), -halo, halo-substituted-($C_1$–$C_5$ alkyl), HO-substituted-($C_1$–$C_5$ alkyl), amino-substituted-($C_1$–$C_5$ alkyl), -hydroxy, —$NO_2$, —$NH_2$, —CN, —NH($C_1$–$C_5$ alkyl), —N($C_1$–$C_5$ alkyl)($C_1$–$C_5$ alkyl), -(nitrogen-containing 3- to 7-membered monocyclic heterocycle), 7- to 10-membered bicycloheterocyclic amine, —$C_1$–$C_{10}$ alkyl, —$C_2$–$C_{10}$ alkenyl, —$C_2$–$C_{10}$ alkynyl, -aryl, -benzyl, —($H_2$NC(O))-substituted ($C_1$–$C_5$ alkyl), carboxy-substituted-($C_1$–$C_5$ alkyl), —C(O)OH, —$C_1$–$C_5$-alkylene-C(O)O—($C_1$–$C_5$ alkyl) or —$C_1$–$C_5$ alkylene-OC(O)—($C_1$–$C_5$ alkyl); and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form a (nitrogen-containing 3- to 7-membered monocyclic hetero cycle) or a -(nitrogen-containing 7- to 10-membered bicyclic heterocycle); or N, $Z_1$ and $Z_2$ are taken together to form a -(nitrogen-containing 3- to 7-membered monocyclic heterocycle), or a -(nitrogen-containing 7- to 10-membered bicyclic heterocycle), in an amount effective to treat Parkinson's disease.

5. The compound of claim 1 having the structure:

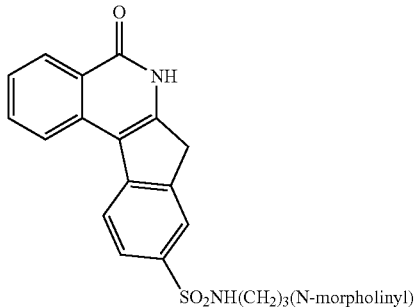

SO$_2$NH(CH$_2$)$_3$(N-morpholinyl)

or a pharmaceutically acceptable salt or hydrate thereof.

6. A composition comprising a pharmaceutically acceptable carrier or vehicle and a compound having the structure:

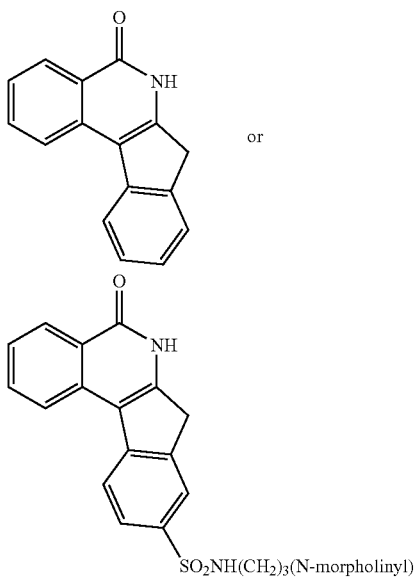

SO$_2$NH(CH$_2$)$_3$(N-morpholinyl)

or a pharmaceutically acceptable salt or hydrate thereof.

7. The method of claim 4, wherein the compound has the structure:

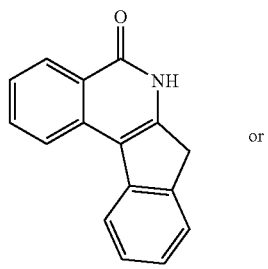

or

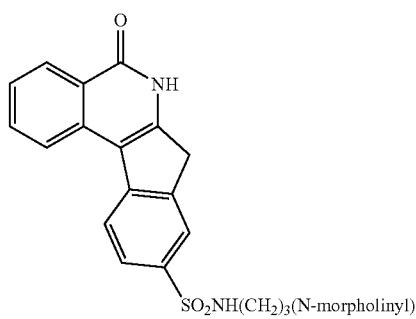

SO$_2$NH(CH$_2$)$_3$(N-morpholinyl)

or a pharmaceutically acceptable salt or hydrate thereof.

8. The compound of claim 1, wherein $R_{1-4}$, $R_7$, and $R_{10}$ are hydrogen.

9. The compound of claim 1, wherein $R_{7-10}$ are hydrogen.

10. The compound of claim 1, wherein $R_6$ is hydrogen.

11. The compound of claim 1, wherein $R_{1-4}$ are hydrogen and $R_5$ is O.

12. The compound of claim 1, wherein $R_{1-4}$, $R_7$, $R_9$, and $R_{10}$ are hydrogen and $R_5$ is O.

13. The compound of claim 1, wherein $R_6$ is hydrogen and $R_5$ is O.

14. The compound of claim 1, having the Formula (IIa')

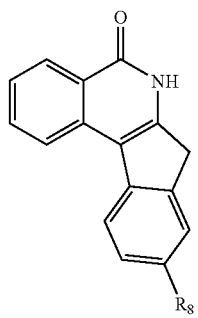

or a pharmaceutically acceptable salt or hydrate thereof.

15. The compound of claim 14, wherein $R_8$ is -A-B, where -A- is —$SO_2$— and —B is —$NZ_1Z_2$ or —($C_1$–$C_5$ alkylene)—$NZ_1Z_2$.

* * * * *

UNITED STATES PATENT AND TRADEMARK OFFICE
CERTIFICATE OF CORRECTION

PATENT NO.        : 7,217,709 B2                                            Page 1 of 1
APPLICATION NO.   : 10/788228
DATED             : May 15, 2007
INVENTOR(S)       : Jagtap et al.

It is certified that error appears in the above-identified patent and that said Letters Patent is hereby corrected as shown below:

Column 26, line 24, should read --Illustrative compounds of Formula (IIa') are set forth below:--. Support for this correction is found in the specification at page 37, line 8.

Column 26, line 44, should read --and pharmaceutically acceptable salts and hydrates thereof.--. Support for this correction is found in the specification at page 37, last line.

Column 35, line 3, should depict the following structure:

--
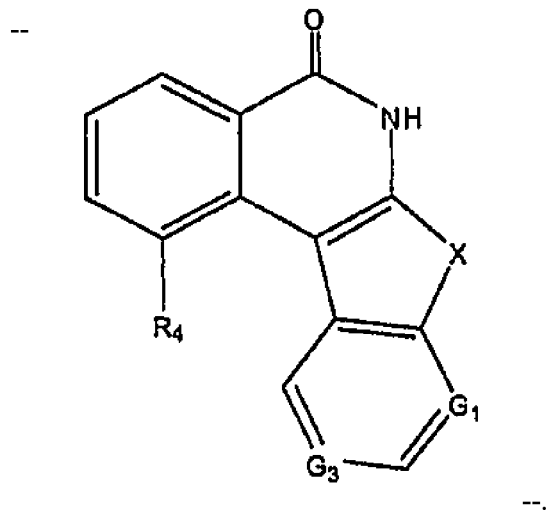
--.

Signed and Sealed this

Seventh Day of August, 2007

JON W. DUDAS
*Director of the United States Patent and Trademark Office*